(12) United States Patent
Connor

(10) Patent No.: US 9,529,385 B2
(45) Date of Patent: Dec. 27, 2016

(54) SMART WATCH AND HUMAN-TO-COMPUTER INTERFACE FOR MONITORING FOOD CONSUMPTION

(71) Applicant: Robert A. Connor, Forest Lake, MN (US)

(72) Inventor: Robert A. Connor, Forest Lake, MN (US)

(73) Assignee: Medibotics LLC, St. Paul, MN (US)

( * ) Notice: Subject to any disclaimer, the term of this patent is extended or adjusted under 35 U.S.C. 154(b) by 275 days.

(21) Appl. No.: 13/901,113

(22) Filed: May 23, 2013

(65) Prior Publication Data

US 2014/0349256 A1    Nov. 27, 2014

(51) Int. Cl.
| | |
|---|---|
| G06F 17/00 | (2006.01) |
| G06F 1/16 | (2006.01) |
| G09B 19/00 | (2006.01) |
| G06F 19/00 | (2011.01) |
| A47G 21/02 | (2006.01) |

(52) U.S. Cl.
CPC ............... *G06F 1/163* (2013.01); *A47G 21/02* (2013.01); *G06F 19/3475* (2013.01); *G09B 19/0092* (2013.01)

(58) Field of Classification Search
CPC ... G06F 19/3475; G06F 1/163; G09B 19/0092
See application file for complete search history.

(56) References Cited

U.S. PATENT DOCUMENTS

| | | |
|---|---|---|
| 3,885,576 A | 5/1975 | Symmes |
| 4,100,401 A | 7/1978 | Tutt et al. |
| 4,192,000 A | 3/1980 | Lipsey |
| 4,207,673 A | 6/1980 | DiGirolamo et al. |
| 4,212,079 A | 7/1980 | Segar et al. |
| 4,218,611 A | 8/1980 | Cannon |

(Continued)

FOREIGN PATENT DOCUMENTS

| | | |
|---|---|---|
| WO | WO 9728738 | 8/1997 |
| WO | WO 03032629 | 4/2003 |

(Continued)

OTHER PUBLICATIONS

U.S. Appl. No. 13/523,739, filed Jun. 14, 2012, Connor.

(Continued)

*Primary Examiner* — Nathan Hillery

(57) ABSTRACT

This invention is a device and system for monitoring a person's food consumption comprising: a wearable sensor that automatically collects data to detect probable eating events; a voluntary human-to-computer interface that is used by the person to enter food consumption data wherein the person is prompted to enter food consumption data when an eating event is detected by the wearable sensor; and a data analysis component that analyzes food consumption data to estimate the types and amounts of ingredients, nutrients, and/or calories that are consumed by the person. In an example, the wearable sensor can be part of a smart watch or smart bracelet. In an example, the voluntary human-to-computer interface can be part of a smart phone. The integrated operation of the wearable sensor and the voluntary human-to-computer interface disclosed in this invention offers accurate measurement of food consumption with low intrusion into the person's privacy.

6 Claims, 6 Drawing Sheets

(56) References Cited

U.S. PATENT DOCUMENTS

| | | |
|---|---|---|
| 4,221,959 A | 9/1980 | Sessler |
| 4,310,316 A | 1/1982 | Thomann |
| 4,321,674 A | 3/1982 | Krames et al. |
| 4,355,645 A | 10/1982 | Mitani et al. |
| 4,509,531 A | 4/1985 | Ward |
| 4,650,218 A | 3/1987 | Hawke |
| 4,686,624 A | 8/1987 | Blum et al. |
| 4,757,453 A | 7/1988 | Nasiff |
| 4,796,182 A | 1/1989 | Duboff |
| 4,819,860 A | 4/1989 | Hargrove et al. |
| 4,823,808 A | 4/1989 | Clegg et al. |
| 4,875,533 A | 10/1989 | Mihara et al. |
| 4,891,756 A | 1/1990 | Williams |
| 4,911,256 A | 3/1990 | Attikiouzel |
| 4,914,819 A | 4/1990 | Ash |
| 4,917,108 A | 4/1990 | Mault |
| 4,951,197 A | 8/1990 | Mellinger |
| 4,965,553 A | 10/1990 | DelBiondo et al. |
| 4,975,682 A | 12/1990 | Kerr et al. |
| 5,033,561 A | 7/1991 | Hettinger |
| 5,038,792 A | 8/1991 | Mault |
| 5,050,612 A | 9/1991 | Matsumura |
| 5,067,488 A | 11/1991 | Fukada et al. |
| 5,148,002 A | 9/1992 | Kuo et al. |
| 5,173,588 A | 12/1992 | Harrah |
| 5,233,520 A | 8/1993 | Kretsch et al. |
| 5,263,491 A | 11/1993 | Thornton |
| 5,285,398 A | 2/1994 | Janik |
| 5,299,356 A | 4/1994 | Maxwell |
| 5,301,679 A | 4/1994 | Taylor |
| 5,388,043 A | 2/1995 | Hettinger |
| 5,398,688 A | 3/1995 | Laniado |
| 5,412,564 A | 5/1995 | Ecer |
| 5,421,089 A | 6/1995 | Dubus et al. |
| 5,424,719 A | 6/1995 | Ravid |
| 5,478,989 A | 12/1995 | Shepley |
| 5,491,651 A | 2/1996 | Janik |
| 5,497,772 A | 3/1996 | Schulman et al. |
| 5,515,858 A | 5/1996 | Myllymaki |
| 5,542,420 A | 8/1996 | Goldman et al. |
| 5,555,490 A | 9/1996 | Carroll |
| 5,563,850 A | 10/1996 | Hanapole |
| 5,581,492 A | 12/1996 | Janik |
| 5,636,146 A | 6/1997 | Flentov et al. |
| 5,673,691 A | 10/1997 | Abrams et al. |
| 5,691,927 A | 11/1997 | Gump |
| 5,704,350 A | 1/1998 | Williams |
| 5,729,479 A | 3/1998 | Golan |
| 5,817,006 A | 10/1998 | Bergh et al. |
| 5,819,735 A | 10/1998 | Mansfield et al. |
| 5,836,312 A | 11/1998 | Moore |
| 5,839,901 A | 11/1998 | Karkanen |
| 5,841,115 A | 11/1998 | Shepley |
| 5,890,128 A | 3/1999 | Diaz et al. |
| 5,908,301 A | 6/1999 | Lutz |
| 5,989,188 A | 11/1999 | Birkhoelzer et al. |
| 6,024,281 A | 2/2000 | Shepley |
| 6,032,676 A | 3/2000 | Moore |
| 6,040,531 A | 3/2000 | Miller-Kovach |
| 6,083,006 A | 7/2000 | Coffman |
| 6,095,949 A | 8/2000 | Arai |
| 6,095,985 A | 8/2000 | Raymond et al. |
| 6,135,950 A | 10/2000 | Adams |
| 6,135,951 A | 10/2000 | Richardson et al. |
| 6,218,358 B1 | 4/2001 | Firestein et al. |
| 6,249,697 B1 | 6/2001 | Asano |
| 6,266,623 B1 | 7/2001 | Vock et al. |
| 6,283,914 B1 | 9/2001 | Mansfield et al. |
| 6,290,646 B1 | 9/2001 | Cosentino et al. |
| 6,336,136 B1 | 1/2002 | Harris |
| 6,341,295 B1 | 1/2002 | Stotler |
| 6,387,329 B1 | 5/2002 | Lewis et al. |
| 6,425,862 B1 | 7/2002 | Brown |
| 6,454,705 B1 | 9/2002 | Cosentino et al. |
| 6,473,368 B1 | 10/2002 | Stanfield |
| 6,478,736 B1 | 11/2002 | Mault |
| 6,498,994 B2 | 12/2002 | Vock et al. |
| 6,506,152 B1 | 1/2003 | Lackey et al. |
| 6,508,762 B2 | 1/2003 | Karnieli |
| 6,513,532 B2 | 2/2003 | Mault et al. |
| 6,527,711 B1 | 3/2003 | Stivoric et al. |
| 6,553,386 B1 | 4/2003 | Alabaster |
| 6,571,200 B1 | 5/2003 | Mault |
| 6,572,542 B1 | 6/2003 | Houben et al. |
| 6,595,929 B2 | 7/2003 | Stivoric et al. |
| 6,605,038 B1 | 8/2003 | Teller et al. |
| 6,610,367 B2 | 8/2003 | Lewis et al. |
| 6,635,015 B2 | 10/2003 | Sagel |
| 6,675,041 B2 | 1/2004 | Dickinson |
| 6,694,182 B1 | 2/2004 | Yamazaki et al. |
| 6,723,045 B2 | 4/2004 | Cosentino et al. |
| 6,745,214 B2 | 6/2004 | Inoue et al. |
| 6,755,783 B2 | 6/2004 | Cosentino et al. |
| 6,765,488 B2 | 7/2004 | Stanfield |
| 6,790,178 B1 | 9/2004 | Mault et al. |
| 6,850,861 B1 | 2/2005 | Faiola et al. |
| 6,856,934 B2 | 2/2005 | Vock et al. |
| 6,856,938 B2 | 2/2005 | Kurtz |
| 6,878,885 B2 | 4/2005 | Miller-Kovach |
| 6,893,406 B2 | 5/2005 | Takeuchi et al. |
| 6,917,897 B2 | 7/2005 | Mork |
| 6,978,221 B1 | 12/2005 | Rudy |
| 7,020,508 B2 | 3/2006 | Stivoric et al. |
| 7,044,739 B2 | 5/2006 | Matson |
| 7,054,784 B2 | 5/2006 | Flentov et al. |
| 7,057,551 B1 | 6/2006 | Vogt |
| 7,096,221 B2 | 8/2006 | Nakano |
| 7,122,152 B2 | 10/2006 | Lewis et al. |
| 7,153,262 B2 | 12/2006 | Stivoric et al. |
| 7,192,136 B2 | 3/2007 | Howell et al. |
| 7,241,880 B2 | 7/2007 | Adler et al. |
| 7,247,023 B2 | 7/2007 | Peplinski et al. |
| 7,255,437 B2 | 8/2007 | Howell et al. |
| 7,261,690 B2 | 8/2007 | Teller et al. |
| 7,285,090 B2 | 10/2007 | Stivoric et al. |
| 7,361,141 B2 | 4/2008 | Nissila et al. |
| 7,373,820 B1 | 5/2008 | James |
| 7,398,151 B1 | 7/2008 | Burrell et al. |
| 7,401,918 B2 | 7/2008 | Howell et al. |
| 7,438,410 B1 | 10/2008 | Howell et al. |
| 7,451,056 B2 | 11/2008 | Flentov et al. |
| 7,454,002 B1 | 11/2008 | Gardner et al. |
| 7,481,531 B2 | 1/2009 | Howell et al. |
| 7,500,937 B2 | 3/2009 | Hercules |
| 7,502,643 B2 | 3/2009 | Farringdon et al. |
| 7,512,515 B2 | 3/2009 | Vock et al. |
| 7,550,683 B2 | 6/2009 | Daughtry |
| 7,577,475 B2 | 8/2009 | Cosentino et al. |
| 7,595,023 B2 | 9/2009 | Lewis et al. |
| 7,640,804 B2 | 1/2010 | Daumer et al. |
| 7,651,868 B2 | 1/2010 | Mcdevitt et al. |
| 7,689,437 B1 | 3/2010 | Teller et al. |
| 7,717,866 B2 | 5/2010 | Damen |
| 7,736,318 B2 | 6/2010 | Cosentino et al. |
| 7,769,635 B2 | 8/2010 | Simons-Nikolova |
| 7,805,196 B2 | 9/2010 | Miesel et al. |
| 7,841,966 B2 | 11/2010 | Aaron et al. |
| 7,855,936 B2 | 12/2010 | Czarnek et al. |
| 7,857,730 B2 | 12/2010 | Dugan |
| 7,878,975 B2 | 2/2011 | Liljeryd et al. |
| 7,882,150 B2 | 2/2011 | Badyal |
| 7,899,709 B2 | 3/2011 | Allard et al. |
| 7,905,815 B2 | 3/2011 | Ellis et al. |
| 7,905,832 B1 | 3/2011 | Lau et al. |
| 7,914,468 B2 | 3/2011 | Shalon et al. |
| 7,931,562 B2 | 4/2011 | Ellis et al. |
| 7,949,506 B1 | 5/2011 | Hill et al. |
| 7,956,997 B2 | 6/2011 | Wang et al. |
| 7,959,567 B2 | 6/2011 | Stivoric et al. |
| 7,980,997 B2 | 7/2011 | Thukral et al. |
| 7,999,674 B2 | 8/2011 | Kamen |
| 8,021,297 B2 | 9/2011 | Aerts |
| 8,033,959 B2 | 10/2011 | Oleson et al. |
| 8,067,185 B2 | 11/2011 | Zoller et al. |

(56) References Cited

U.S. PATENT DOCUMENTS

| | | |
|---|---|---|
| 8,068,858 B2 | 11/2011 | Werner et al. |
| 8,073,707 B2 | 12/2011 | Teller et al. |
| 8,075,451 B2 | 12/2011 | Dugan |
| 8,087,937 B2 | 1/2012 | Peplinski et al. |
| 8,112,281 B2 | 2/2012 | Yeung et al. |
| 8,116,841 B2 | 2/2012 | Bly et al. |
| 8,121,673 B2 | 2/2012 | Tran |
| 8,157,731 B2 | 4/2012 | Teller et al. |
| 8,158,082 B2 | 4/2012 | Imran |
| 8,162,804 B2 | 4/2012 | Tagliabue |
| 8,170,656 B2 | 5/2012 | Tan et al. |
| 8,180,591 B2 | 5/2012 | Yuen et al. |
| 8,180,592 B2 | 5/2012 | Yuen et al. |
| 8,184,070 B1 | 5/2012 | Taubman |
| 8,229,676 B2 | 7/2012 | Hyde et al. |
| 8,236,242 B2 | 8/2012 | Drucker et al. |
| 8,244,278 B2 | 8/2012 | Werner et al. |
| 8,265,907 B2 | 9/2012 | Nanikashvili et al. |
| 8,275,438 B2 | 9/2012 | Simpson et al. |
| 8,275,635 B2 | 9/2012 | Stivoric et al. |
| 8,280,476 B2 | 10/2012 | Jina |
| 8,285,356 B2 | 10/2012 | Bly et al. |
| 8,285,488 B2 | 10/2012 | Hyde et al. |
| 8,287,453 B2 | 10/2012 | Li et al. |
| 8,290,712 B2 | 10/2012 | Hyde et al. |
| 8,294,581 B2 | 10/2012 | Kamen |
| 8,298,142 B2 | 10/2012 | Simpson et al. |
| 8,299,930 B2 | 10/2012 | Schmid-Schonbein et al. |
| 8,310,368 B2 | 11/2012 | Hoover et al. |
| 8,311,769 B2 | 11/2012 | Yuen et al. |
| 8,311,770 B2 | 11/2012 | Yuen et al. |
| 8,314,224 B2 | 11/2012 | Adler et al. |
| 8,321,141 B2 | 11/2012 | Hyde et al. |
| 8,323,188 B2 | 12/2012 | Tran |
| 8,323,189 B2 | 12/2012 | Tran et al. |
| 8,323,218 B2 | 12/2012 | Davis et al. |
| 8,328,718 B2 | 12/2012 | Tran |
| 8,330,057 B2 | 12/2012 | Sharawi et al. |
| 8,334,367 B2 | 12/2012 | Adler |
| 8,337,367 B2 | 12/2012 | Dugan |
| 8,340,754 B2 | 12/2012 | Chamney et al. |
| 8,344,325 B2 | 1/2013 | Merrell et al. |
| 8,344,998 B2 | 1/2013 | Fitzgerald et al. |
| 8,345,414 B2 | 1/2013 | Mooring et al. |
| 8,345,930 B2 | 1/2013 | Tamrakar et al. |
| 8,352,211 B2 | 1/2013 | Vock et al. |
| 8,355,875 B2 | 1/2013 | Hyde et al. |
| 8,363,913 B2 | 1/2013 | Boushey et al. |
| 8,364,250 B2 | 1/2013 | Moon et al. |
| 8,369,919 B2 | 2/2013 | Kamath et al. |
| 8,369,936 B2 | 2/2013 | Farringdon et al. |
| 8,370,176 B2 | 2/2013 | Vespasiani |
| 8,370,549 B2 | 2/2013 | Burton et al. |
| 8,378,811 B2 | 2/2013 | Crump et al. |
| 8,379,488 B1 | 2/2013 | Gossweiler et al. |
| 8,382,482 B2 | 2/2013 | Miller-Kovach et al. |
| 8,382,681 B2 | 2/2013 | Escutia et al. |
| 8,386,008 B2 | 2/2013 | Yuen et al. |
| 8,386,185 B2 | 2/2013 | Hyde et al. |
| 8,392,123 B2 | 3/2013 | Hyde et al. |
| 8,392,124 B2 | 3/2013 | Hyde et al. |
| 8,392,125 B2 | 3/2013 | Hyde et al. |
| 8,396,672 B2 | 3/2013 | Hyde et al. |
| 8,398,546 B2 | 3/2013 | Pacione et al. |
| 8,403,845 B2 | 3/2013 | Stivoric et al. |
| 8,408,436 B2 | 4/2013 | Berry et al. |
| 8,409,118 B2 | 4/2013 | Agrawal et al. |
| 8,416,102 B2 | 4/2013 | Yin |
| 8,417,298 B2 | 4/2013 | Mittleman et al. |
| 8,417,312 B2 | 4/2013 | Kamath et al. |
| 8,419,268 B2 | 4/2013 | Yu |
| 8,421,620 B2 | 4/2013 | Boyd et al. |
| 8,421,634 B2 | 4/2013 | Tan et al. |
| 8,423,113 B2 | 4/2013 | Shariati et al. |
| 8,423,378 B1 | 4/2013 | Goldberg |
| 8,423,380 B1 | 4/2013 | Gelly |
| 8,425,415 B2 | 4/2013 | Tran |
| 8,437,823 B2 | 5/2013 | Ozawa et al. |
| 8,437,980 B2 | 5/2013 | Yuen et al. |
| 8,438,038 B2 | 5/2013 | Cosentino et al. |
| 8,438,163 B1 | 5/2013 | Li et al. |
| 8,439,683 B2 | 5/2013 | Puri et al. |
| 8,446,275 B2 | 5/2013 | Utter |
| 8,447,403 B2 | 5/2013 | Sharma et al. |
| 8,447,404 B2 | 5/2013 | Sharma et al. |
| 8,449,560 B2 | 5/2013 | Roth et al. |
| 8,463,573 B2 | 6/2013 | Flentov et al. |
| 8,463,576 B2 | 6/2013 | Yuen et al. |
| 8,463,577 B2 | 6/2013 | Yuen et al. |
| 8,465,447 B2 | 6/2013 | Krueger et al. |
| 8,467,869 B2 | 6/2013 | Schuler |
| 8,475,367 B1 | 7/2013 | Yuen et al. |
| 8,475,368 B2 | 7/2013 | Tran et al. |
| 8,475,370 B2 | 7/2013 | McCombie et al. |
| 8,478,398 B2 | 7/2013 | Schuler |
| 8,478,606 B2 | 7/2013 | Bodlaender et al. |
| 8,483,830 B2 | 7/2013 | Tweden et al. |
| 8,486,153 B2 | 7/2013 | Levine et al. |
| 8,571,880 B2 | 10/2013 | Goldberg |
| 8,583,402 B2 | 11/2013 | Yuen et al. |
| 8,585,771 B2 | 11/2013 | Binmoeller et al. |
| 8,587,670 B2 | 11/2013 | Wood et al. |
| 8,595,023 B2 | 11/2013 | Kirchhoff et al. |
| 8,600,928 B2 | 12/2013 | Landers |
| 8,603,186 B2 | 12/2013 | Binmoeller |
| 8,605,952 B2 | 12/2013 | Boushey et al. |
| 2001/0049470 A1 | 12/2001 | Mault et al. |
| 2002/0022774 A1 | 2/2002 | Karnieli |
| 2002/0027164 A1 | 3/2002 | Mault et al. |
| 2002/0047867 A1 | 4/2002 | Mault et al. |
| 2002/0049482 A1 | 4/2002 | Fabian et al. |
| 2002/0062069 A1 | 5/2002 | Mault |
| 2002/0109600 A1 | 8/2002 | Mault et al. |
| 2002/0124017 A1 | 9/2002 | Mault |
| 2002/0133378 A1 | 9/2002 | Mault et al. |
| 2002/0156351 A1 | 10/2002 | Sagel |
| 2002/0167863 A1 | 11/2002 | Davis et al. |
| 2003/0065257 A1 | 4/2003 | Mault et al. |
| 2003/0076983 A1 | 4/2003 | Cox |
| 2003/0152607 A1 | 8/2003 | Mault |
| 2003/0163354 A1 | 8/2003 | Shamoun |
| 2003/0165799 A1 | 9/2003 | Bisogno |
| 2003/0208110 A1 | 11/2003 | Mault et al. |
| 2003/0219513 A1 | 11/2003 | Gordon |
| 2004/0034289 A1 | 2/2004 | Teller et al. |
| 2004/0073142 A1 | 4/2004 | Takeuchi et al. |
| 2004/0100376 A1 | 5/2004 | Lye et al. |
| 2004/0133081 A1 | 7/2004 | Teller et al. |
| 2004/0152957 A1 | 8/2004 | Stivoric et al. |
| 2005/0004436 A1 | 1/2005 | Nissila et al. |
| 2005/0008994 A1 | 1/2005 | Bisogno |
| 2005/0011367 A1 | 1/2005 | Crow |
| 2005/0014111 A1 | 1/2005 | Matson |
| 2005/0113649 A1 | 5/2005 | Bergantino |
| 2005/0113650 A1 | 5/2005 | Pacione et al. |
| 2005/0146419 A1 | 7/2005 | Porter |
| 2005/0153052 A1 | 7/2005 | Williams et al. |
| 2005/0184148 A1 | 8/2005 | Perlman |
| 2005/0247213 A1 | 11/2005 | Slilaty |
| 2005/0263160 A1 | 12/2005 | Utley et al. |
| 2005/0266385 A1 | 12/2005 | Bisogno |
| 2005/0283096 A1 | 12/2005 | Chau et al. |
| 2006/0015016 A1 | 1/2006 | Thornton |
| 2006/0031102 A1 | 2/2006 | Teller et al. |
| 2006/0036395 A1 | 2/2006 | Shaya et al. |
| 2006/0064037 A1 | 3/2006 | Shalon et al. |
| 2006/0074716 A1 | 4/2006 | Tilles et al. |
| 2006/0122468 A1 | 6/2006 | Tavor |
| 2006/0122474 A1 | 6/2006 | Teller et al. |
| 2006/0189853 A1 | 8/2006 | Brown |
| 2006/0197670 A1 | 9/2006 | Breibart |
| 2006/0229504 A1 | 10/2006 | Johnson |
| 2006/0263750 A1 | 11/2006 | Gordon |
| 2006/0264730 A1 | 11/2006 | Stivoric et al. |

(56) References Cited

U.S. PATENT DOCUMENTS

| | | |
|---|---|---|
| 2007/0021979 A1 | 1/2007 | Cosentino et al. |
| 2007/0027366 A1 | 2/2007 | Osburn |
| 2007/0028453 A1 | 2/2007 | Crow |
| 2007/0030339 A1 | 2/2007 | Findlay et al. |
| 2007/0050058 A1 | 3/2007 | Zuziak et al. |
| 2007/0059672 A1 | 3/2007 | Shaw |
| 2007/0089335 A1 | 4/2007 | Smith et al. |
| 2007/0098856 A1 | 5/2007 | LePine |
| 2007/0100666 A1 | 5/2007 | Stivoric et al. |
| 2007/0106129 A1 | 5/2007 | Srivathsa et al. |
| 2007/0173703 A1 | 7/2007 | Lee et al. |
| 2007/0179355 A1 | 8/2007 | Rosen |
| 2007/0208593 A1 | 9/2007 | Hercules |
| 2008/0019122 A1 | 1/2008 | Kramer |
| 2008/0036737 A1 | 2/2008 | Hernandez-Rebollar |
| 2008/0060853 A1 | 3/2008 | Davidson et al. |
| 2008/0137486 A1 | 6/2008 | Czarenk et al. |
| 2008/0140444 A1 | 6/2008 | Karkanias et al. |
| 2008/0161654 A1 | 7/2008 | Teller et al. |
| 2008/0161655 A1 | 7/2008 | Teller et al. |
| 2008/0167535 A1 | 7/2008 | Andre et al. |
| 2008/0167536 A1 | 7/2008 | Teller et al. |
| 2008/0167537 A1 | 7/2008 | Teller et al. |
| 2008/0167538 A1 | 7/2008 | Teller et al. |
| 2008/0167539 A1 | 7/2008 | Teller et al. |
| 2008/0171920 A1 | 7/2008 | Teller et al. |
| 2008/0171921 A1 | 7/2008 | Teller et al. |
| 2008/0171922 A1 | 7/2008 | Teller et al. |
| 2008/0255955 A1 | 10/2008 | Simons-Nikolova |
| 2008/0262557 A1 | 10/2008 | Brown |
| 2008/0267444 A1 | 10/2008 | Simons-Nikolova |
| 2008/0270324 A1 | 10/2008 | Allard et al. |
| 2008/0275309 A1 | 11/2008 | Stivoric et al. |
| 2008/0276461 A1 | 11/2008 | Gold |
| 2009/0012433 A1 | 1/2009 | Fernstrom et al. |
| 2009/0112800 A1 | 4/2009 | Athsani |
| 2009/0176526 A1 | 7/2009 | Altman |
| 2009/0177068 A1 | 7/2009 | Stivoric et al. |
| 2009/0191514 A1 | 7/2009 | Barnow |
| 2009/0219159 A1 | 9/2009 | Morgenstern |
| 2009/0253105 A1 | 10/2009 | Lepine |
| 2009/0261987 A1 | 10/2009 | Sun |
| 2010/0000292 A1 | 1/2010 | Karabacak et al. |
| 2010/0003647 A1 | 1/2010 | Brown et al. |
| 2010/0049004 A1 | 2/2010 | Edman et al. |
| 2010/0049010 A1 | 2/2010 | Goldreich |
| 2010/0055271 A1 | 3/2010 | Miller-Kovach et al. |
| 2010/0055652 A1 | 3/2010 | Miller-Kovach et al. |
| 2010/0055653 A1 | 3/2010 | Miller-Kovach et al. |
| 2010/0057564 A1 | 3/2010 | Godsey et al. |
| 2010/0062119 A1 | 3/2010 | Miller-Kovach |
| 2010/0062402 A1 | 3/2010 | Miller-Kovach |
| 2010/0079291 A1 | 4/2010 | Kroll et al. |
| 2010/0080875 A1 | 4/2010 | Miller-Kovach |
| 2010/0109876 A1 | 5/2010 | Schmid-Schonbein et al. |
| 2010/0111383 A1 | 5/2010 | Boushey et al. |
| 2010/0125176 A1 | 5/2010 | Hyde et al. |
| 2010/0125177 A1 | 5/2010 | Hyde et al. |
| 2010/0125178 A1 | 5/2010 | Hyde et al. |
| 2010/0125179 A1 | 5/2010 | Hyde et al. |
| 2010/0125180 A1 | 5/2010 | Hyde et al. |
| 2010/0125181 A1 | 5/2010 | Hyde et al. |
| 2010/0125417 A1 | 5/2010 | Hyde et al. |
| 2010/0125418 A1 | 5/2010 | Hyde et al. |
| 2010/0125419 A1 | 5/2010 | Hyde et al. |
| 2010/0125420 A1 | 5/2010 | Hyde et al. |
| 2010/0173269 A1 | 7/2010 | Puri et al. |
| 2010/0191155 A1 | 7/2010 | Kim et al. |
| 2010/0194573 A1 | 8/2010 | Hoover et al. |
| 2010/0205209 A1 | 8/2010 | Jokinen |
| 2010/0209897 A1 | 8/2010 | Utley et al. |
| 2010/0228160 A1 | 9/2010 | Schweizer |
| 2010/0240962 A1 | 9/2010 | Contant |
| 2010/0291515 A1 | 11/2010 | Pinnisi et al. |
| 2010/0332571 A1 | 12/2010 | Healey et al. |
| 2011/0053128 A1 | 3/2011 | Alman |
| 2011/0077471 A1 | 3/2011 | King |
| 2011/0087137 A1 | 4/2011 | Hanoun |
| 2011/0124978 A1 | 5/2011 | Williams |
| 2011/0125063 A1 | 5/2011 | Shalon et al. |
| 2011/0182477 A1 | 7/2011 | Tamrakar et al. |
| 2011/0184247 A1 | 7/2011 | Contant et al. |
| 2011/0205851 A1 | 8/2011 | Harris |
| 2011/0218407 A1 | 9/2011 | Haberman et al. |
| 2011/0276312 A1 | 11/2011 | Shalon et al. |
| 2011/0281245 A1 | 11/2011 | Mansour |
| 2011/0288379 A1 | 11/2011 | Wu |
| 2011/0318717 A1 | 12/2011 | Adamowicz |
| 2012/0004883 A1 | 1/2012 | Vock et al. |
| 2012/0015432 A1 | 1/2012 | Adler |
| 2012/0021388 A1 | 1/2012 | Arbuckle et al. |
| 2012/0031805 A1 | 2/2012 | Stolarczyk |
| 2012/0053426 A1 | 3/2012 | Webster et al. |
| 2012/0055718 A1 | 3/2012 | Chen |
| 2012/0071731 A1 | 3/2012 | Gottesman |
| 2012/0072233 A1 | 3/2012 | Hanlon et al. |
| 2012/0077154 A1 | 3/2012 | Highet et al. |
| 2012/0078071 A1 | 3/2012 | Bohm et al. |
| 2012/0083669 A1 | 4/2012 | Abujbara |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0096405 A1 | 4/2012 | Seo |
| 2012/0115111 A1 | 5/2012 | Lepine |
| 2012/0126983 A1 | 5/2012 | Breibart |
| 2012/0144912 A1 | 6/2012 | Kates et al. |
| 2012/0149996 A1 | 6/2012 | Stivoric et al. |
| 2012/0150074 A1 | 6/2012 | Yanev et al. |
| 2012/0150327 A1 | 6/2012 | Altman et al. |
| 2012/0170801 A1 | 7/2012 | De Oliveira et al. |
| 2012/0178065 A1 | 7/2012 | Naghavi et al. |
| 2012/0179020 A1 | 7/2012 | Wekell |
| 2012/0179665 A1 | 7/2012 | Baarman et al. |
| 2012/0188158 A1 | 7/2012 | Tan et al. |
| 2012/0191052 A1 | 7/2012 | Rao |
| 2012/0194418 A1 | 8/2012 | Osterhout et al. |
| 2012/0194419 A1 | 8/2012 | Osterhout et al. |
| 2012/0194420 A1 | 8/2012 | Osterhout et al. |
| 2012/0194549 A1 | 8/2012 | Osterhout et al. |
| 2012/0194550 A1 | 8/2012 | Osterhout et al. |
| 2012/0194551 A1 | 8/2012 | Osterhout et al. |
| 2012/0194552 A1 | 8/2012 | Osterhout et al. |
| 2012/0194553 A1 | 8/2012 | Osterhout et al. |
| 2012/0200488 A1 | 8/2012 | Osterhout et al. |
| 2012/0200499 A1 | 8/2012 | Osterhout et al. |
| 2012/0200601 A1 | 8/2012 | Osterhout et al. |
| 2012/0201725 A1 | 8/2012 | Imran |
| 2012/0203081 A1 | 8/2012 | Leboeuf et al. |
| 2012/0206322 A1 | 8/2012 | Osterhout et al. |
| 2012/0206323 A1 | 8/2012 | Osterhout et al. |
| 2012/0206334 A1 | 8/2012 | Osterhout et al. |
| 2012/0206335 A1 | 8/2012 | Osterhout et al. |
| 2012/0206485 A1 | 8/2012 | Osterhout et al. |
| 2012/0212398 A1 | 8/2012 | Border et al. |
| 2012/0212399 A1 | 8/2012 | Border et al. |
| 2012/0212400 A1 | 8/2012 | Border et al. |
| 2012/0212406 A1 | 8/2012 | Osterhout et al. |
| 2012/0212414 A1 | 8/2012 | Osterhout et al. |
| 2012/0214594 A1 | 8/2012 | Kirovski et al. |
| 2012/0218172 A1 | 8/2012 | Border et al. |
| 2012/0218301 A1 | 8/2012 | Miller |
| 2012/0221495 A1 | 8/2012 | Landers |
| 2012/0226471 A1 | 9/2012 | Yuen et al. |
| 2012/0226472 A1 | 9/2012 | Yuen et al. |
| 2012/0231960 A1 | 9/2012 | Osterfeld et al. |
| 2012/0235647 A1 | 9/2012 | Chung et al. |
| 2012/0235883 A1 | 9/2012 | Border et al. |
| 2012/0235885 A1 | 9/2012 | Miller et al. |
| 2012/0235886 A1 | 9/2012 | Border et al. |
| 2012/0235887 A1 | 9/2012 | Border et al. |
| 2012/0235900 A1 | 9/2012 | Border et al. |

(56) References Cited

U.S. PATENT DOCUMENTS

| | | |
|---|---|---|
| 2012/0236030 A1 | 9/2012 | Border et al. |
| 2012/0236031 A1 | 9/2012 | Haddick et al. |
| 2012/0239304 A1 | 9/2012 | Hayter et al. |
| 2012/0242626 A1 | 9/2012 | Hu |
| 2012/0242678 A1 | 9/2012 | Border et al. |
| 2012/0242697 A1 | 9/2012 | Border et al. |
| 2012/0242698 A1 | 9/2012 | Haddick et al. |
| 2012/0245472 A1 | 9/2012 | Rulkov et al. |
| 2012/0245714 A1 | 9/2012 | Mueller et al. |
| 2012/0245716 A1 | 9/2012 | Srinivasan et al. |
| 2012/0249797 A1 | 10/2012 | Haddick et al. |
| 2012/0251079 A1 | 10/2012 | Meschter et al. |
| 2012/0253485 A1 | 10/2012 | Weast et al. |
| 2012/0254749 A1 | 10/2012 | Downs et al. |
| 2012/0258433 A1 | 10/2012 | Hope et al. |
| 2012/0258804 A1 | 10/2012 | Ahmed |
| 2012/0268592 A1 | 10/2012 | Aragones et al. |
| 2012/0274508 A1 | 11/2012 | Brown et al. |
| 2012/0274554 A1 | 11/2012 | Kinoshita et al. |
| 2012/0277638 A1 | 11/2012 | Skelton et al. |
| 2012/0283855 A1 | 11/2012 | Hoffman et al. |
| 2012/0289867 A1 | 11/2012 | Kasama |
| 2012/0290109 A1 | 11/2012 | Engelberg et al. |
| 2012/0295233 A1 | 11/2012 | Cooperman |
| 2012/0302855 A1 | 11/2012 | Kamath et al. |
| 2012/0303638 A1 | 11/2012 | Bousamra et al. |
| 2012/0310971 A1 | 12/2012 | Tran |
| 2012/0313776 A1 | 12/2012 | Utter |
| 2012/0315609 A1 | 12/2012 | Miller-Kovach et al. |
| 2012/0315986 A1 | 12/2012 | Walling |
| 2012/0316406 A1 | 12/2012 | Rahman et al. |
| 2012/0316455 A1 | 12/2012 | Rahman et al. |
| 2012/0316456 A1 | 12/2012 | Rahman et al. |
| 2012/0316458 A1 | 12/2012 | Rahman et al. |
| 2012/0316471 A1 | 12/2012 | Rahman et al. |
| 2012/0316661 A1 | 12/2012 | Rahman et al. |
| 2012/0316793 A1 | 12/2012 | Jung et al. |
| 2012/0316896 A1 | 12/2012 | Rahman et al. |
| 2012/0316932 A1 | 12/2012 | Rahman et al. |
| 2012/0317167 A1 | 12/2012 | Rahman et al. |
| 2012/0317430 A1 | 12/2012 | Rahman et al. |
| 2012/0321759 A1 | 12/2012 | Marinkovich et al. |
| 2012/0323346 A1 | 12/2012 | Ashby et al. |
| 2012/0323496 A1 | 12/2012 | Burroughs et al. |
| 2012/0326863 A1 | 12/2012 | Johnson et al. |
| 2012/0326873 A1 | 12/2012 | Utter |
| 2012/0330109 A1 | 12/2012 | Tran |
| 2012/0330112 A1 | 12/2012 | Lamego et al. |
| 2012/0331201 A1 | 12/2012 | Rondel |
| 2013/0002435 A1 | 1/2013 | Utter |
| 2013/0002538 A1 | 1/2013 | Mooring et al. |
| 2013/0002545 A1 | 1/2013 | Heinrich et al. |
| 2013/0002724 A1 | 1/2013 | Heinrich et al. |
| 2013/0004923 A1 | 1/2013 | Utter |
| 2013/0005534 A1 | 1/2013 | Rosenbaum |
| 2013/0006063 A1 | 1/2013 | Wang |
| 2013/0006125 A1 | 1/2013 | Kroll et al. |
| 2013/0006583 A1 | 1/2013 | Weast et al. |
| 2013/0006802 A1 | 1/2013 | Dillahunt et al. |
| 2013/0006807 A1 | 1/2013 | Bai et al. |
| 2013/0009783 A1 | 1/2013 | Tran |
| 2013/0012788 A1 | 1/2013 | Horseman |
| 2013/0012789 A1 | 1/2013 | Horseman |
| 2013/0012790 A1 | 1/2013 | Horseman |
| 2013/0012802 A1 | 1/2013 | Horseman |
| 2013/0013331 A1 | 1/2013 | Horseman |
| 2013/0017789 A1 | 1/2013 | Chi et al. |
| 2013/0021226 A1 | 1/2013 | Bell |
| 2013/0021658 A1 | 1/2013 | Miao et al. |
| 2013/0027060 A1 | 1/2013 | Tralshawala et al. |
| 2013/0029807 A1 | 1/2013 | Amsel |
| 2013/0035563 A1 | 2/2013 | Angelides |
| 2013/0035575 A1 | 2/2013 | Mayou et al. |
| 2013/0035865 A1 | 2/2013 | Mayou et al. |
| 2013/0038056 A1 | 2/2013 | Donelan et al. |
| 2013/0041272 A1 | 2/2013 | Guillen et al. |
| 2013/0041617 A1 | 2/2013 | Pease et al. |
| 2013/0043997 A1 | 2/2013 | Cosentino et al. |
| 2013/0044042 A1 | 2/2013 | Olsson et al. |
| 2013/0045037 A1 | 2/2013 | Schaffer |
| 2013/0045467 A1 | 2/2013 | Kamen |
| 2013/0048737 A1 | 2/2013 | Baym et al. |
| 2013/0048738 A1 | 2/2013 | Baym et al. |
| 2013/0049931 A1 | 2/2013 | Baym et al. |
| 2013/0049932 A1 | 2/2013 | Baym et al. |
| 2013/0049933 A1 | 2/2013 | Baym et al. |
| 2013/0049934 A1 | 2/2013 | Baym et al. |
| 2013/0052623 A1 | 2/2013 | Thukral et al. |
| 2013/0053655 A1 | 2/2013 | Castellanos |
| 2013/0053661 A1 | 2/2013 | Alberth et al. |
| 2013/0053990 A1 | 2/2013 | Ackland |
| 2013/0063342 A1 | 3/2013 | Chen et al. |
| 2013/0065680 A1 | 3/2013 | Zavadsky et al. |
| 2013/0069780 A1 | 3/2013 | Tran et al. |
| 2013/0069931 A1 | 3/2013 | Wilson et al. |
| 2013/0069985 A1 | 3/2013 | Wong et al. |
| 2013/0070338 A1 | 3/2013 | Gupta et al. |
| 2013/0072765 A1 | 3/2013 | Kahn et al. |
| 2013/0072807 A1 | 3/2013 | Tran |
| 2013/0073254 A1 | 3/2013 | Yuen et al. |
| 2013/0073255 A1 | 3/2013 | Yuen et al. |
| 2013/0073368 A1 | 3/2013 | Squires |
| 2013/0080113 A1 | 3/2013 | Yuen et al. |
| 2013/0083003 A1 | 4/2013 | Perez et al. |
| 2013/0083009 A1 | 4/2013 | Geisner et al. |
| 2013/0083064 A1 | 4/2013 | Geisner et al. |
| 2013/0083496 A1 | 4/2013 | Franklin et al. |
| 2013/0090565 A1 | 4/2013 | Quy |
| 2013/0091454 A1 | 4/2013 | Papa et al. |
| 2013/0095459 A1 | 4/2013 | Tran |
| 2013/0096843 A1 | 4/2013 | Yuen et al. |
| 2013/0100027 A1 | 4/2013 | Wang et al. |
| 2013/0102387 A1 | 4/2013 | Barsoum et al. |
| 2013/0103416 A1 | 4/2013 | Amigo et al. |
| 2013/0105565 A1 | 5/2013 | Kamprath |
| 2013/0106603 A1 | 5/2013 | Weast et al. |
| 2013/0106684 A1 | 5/2013 | Weast et al. |
| 2013/0107674 A1 | 5/2013 | Gossweiler et al. |
| 2013/0108993 A1 | 5/2013 | Katz |
| 2013/0109947 A1 | 5/2013 | Wood |
| 2013/0110011 A1 | 5/2013 | McGregor et al. |
| 2013/0110264 A1 | 5/2013 | Weast et al. |
| 2013/0110549 A1 | 5/2013 | Laan et al. |
| 2013/0111611 A1 | 5/2013 | Barros Almedo et al. |
| 2013/0113933 A1 | 5/2013 | Boushey et al. |
| 2013/0115583 A1 | 5/2013 | Gordon et al. |
| 2013/0115584 A1 | 5/2013 | Gordon et al. |
| 2013/0115717 A1 | 5/2013 | Guo et al. |
| 2013/0116525 A1 | 5/2013 | Heller et al. |
| 2013/0117040 A1 | 5/2013 | James et al. |
| 2013/0117041 A1 | 5/2013 | Boyce et al. |
| 2013/0117135 A1 | 5/2013 | Riddiford et al. |
| 2013/0119255 A1 | 5/2013 | Dickinson et al. |
| 2013/0127980 A1 | 5/2013 | Haddick et al. |
| 2013/0130213 A1 | 5/2013 | Burbank et al. |
| 2013/0131519 A1 | 5/2013 | LeBoeuf et al. |
| 2013/0132319 A1 | 5/2013 | Landers |
| 2013/0138230 A1 | 5/2013 | Landers |
| 2013/0141235 A1 | 6/2013 | Utter |
| 2013/0141313 A1 | 6/2013 | Zhou et al. |
| 2013/0149965 A1 | 6/2013 | Gilad-Bachrach et al. |
| 2013/0151196 A1 | 6/2013 | Yuen et al. |
| 2013/0157232 A1 | 6/2013 | Ehrenkranz |
| 2013/0158367 A1 | 6/2013 | Pacione et al. |
| 2013/0158368 A1 | 6/2013 | Pacione et al. |
| 2013/0165842 A1 | 6/2013 | Binmoeller |
| 2013/0178912 A1 | 7/2013 | Sharma |
| 2013/0183400 A1 | 7/2013 | Ioncescu |
| 2013/0184635 A1 | 7/2013 | Levy et al. |
| 2013/0187780 A1 | 7/2013 | Angelides |
| 2013/0253410 A1 | 9/2013 | Levine et al. |
| 2013/0260345 A1 | 10/2013 | Puri et al. |
| 2013/0267794 A1 | 10/2013 | Fernstrom et al. |
| 2013/0268111 A1 | 10/2013 | Dekar |

(56) References Cited

U.S. PATENT DOCUMENTS

| | | |
|---|---|---|
| 2013/0273506 A1 | 10/2013 | Melowsky |
| 2013/0273508 A1 | 10/2013 | Hyde et al. |
| 2013/0280681 A1 | 10/2013 | Narayan et al. |
| 2013/0282398 A1 | 10/2013 | Goldberg |
| 2013/0289466 A1 | 10/2013 | Babkes et al. |
| 2013/0289886 A1 | 10/2013 | Ricks |
| 2013/0289889 A1 | 10/2013 | Yuen et al. |
| 2013/0295531 A1 | 11/2013 | Addanki et al. |
| 2013/0296899 A1 | 11/2013 | Deem et al. |
| 2013/0303335 A1 | 11/2013 | Guidi et al. |
| 2013/0303869 A1 | 11/2013 | Rebec et al. |
| 2013/0306648 A1 | 11/2013 | Kemper |
| 2013/0306853 A1 | 11/2013 | Eastwood |
| 2013/0310658 A1 | 11/2013 | Ricks et al. |
| 2013/0310727 A1 | 11/2013 | Stack et al. |
| 2013/0325394 A1 | 12/2013 | Yuen et al. |
| 2013/0325396 A1 | 12/2013 | Yuen et al. |
| 2013/0325399 A1 | 12/2013 | Yuen et al. |
| 2013/0325404 A1 | 12/2013 | Yuen et al. |
| 2013/0330694 A1 | 12/2013 | Watterson |

FOREIGN PATENT DOCUMENTS

| | | |
|---|---|---|
| WO | WO 2005029242 | 6/2005 |
| WO | WO 2010070645 | 6/2010 |
| WO | WO 2012170584 | 12/2012 |

OTHER PUBLICATIONS

U.S. Appl. No. 13/616,238, filed Sep. 14, 2012, Connor.

Lee, Nicole, "AIRO wristband tracks not just sleep, exercise and stress, but also what you eat," Engadget, Oct. 28, 2013, http://www.engadget.com/2013/10/28/airo-wristband/.

"TellSpec Launches Campaign for the World's First Handheld Consumer Device that Analyzes Chemicals and Allergens in Food," Toronto, Canada (PRWEB), Oct. 2, 2013.

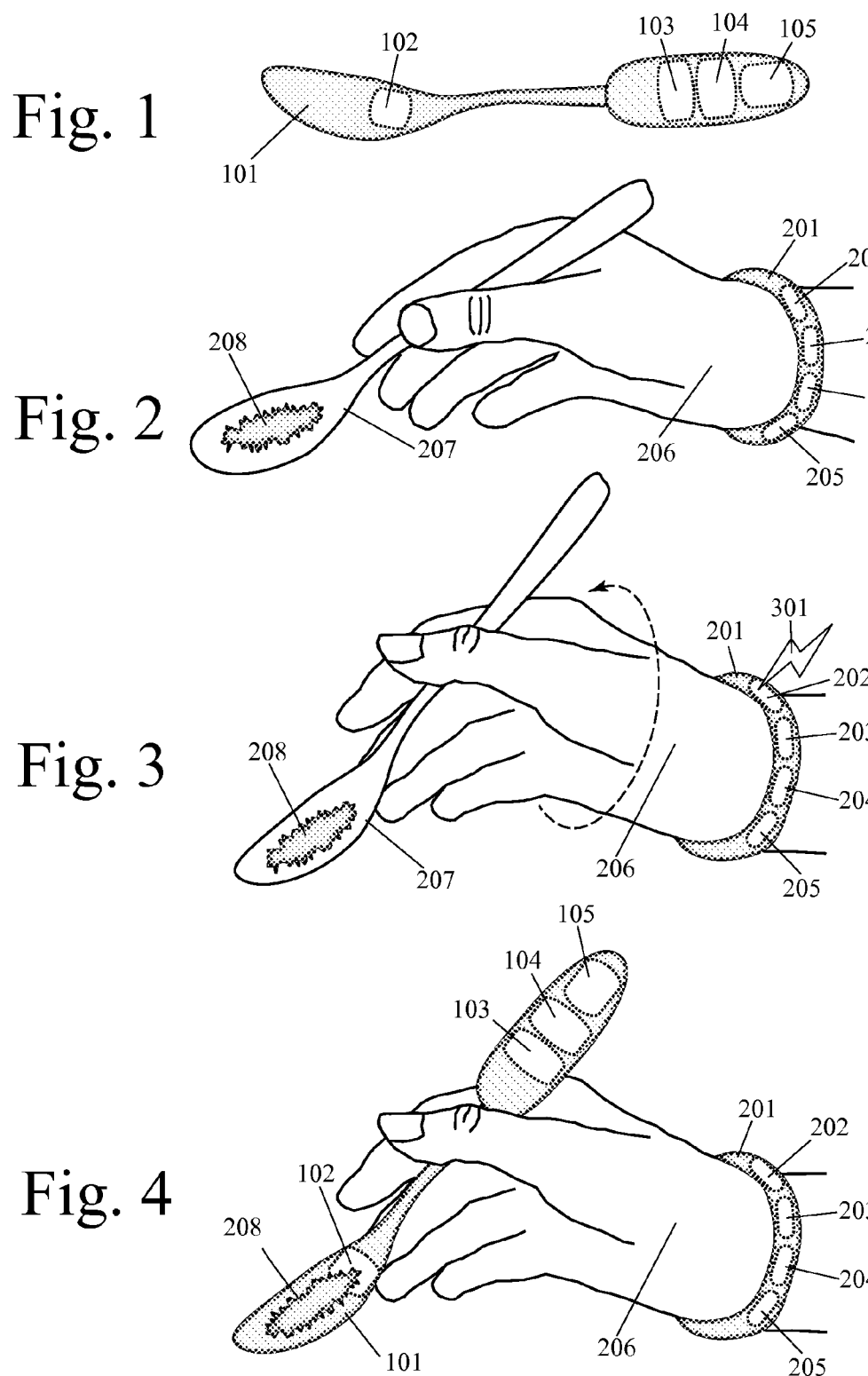

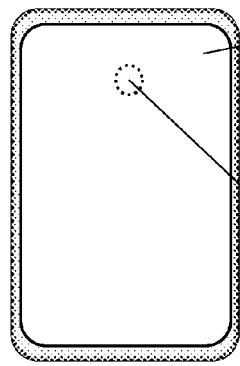
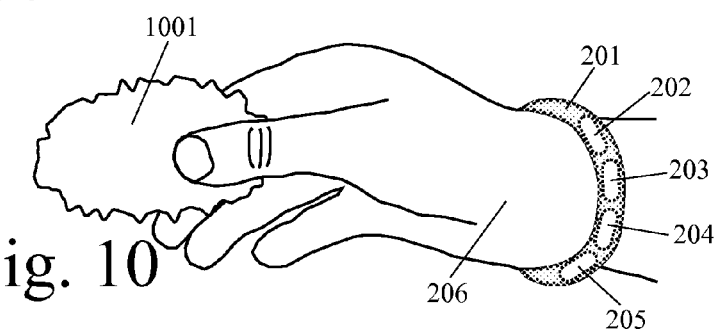
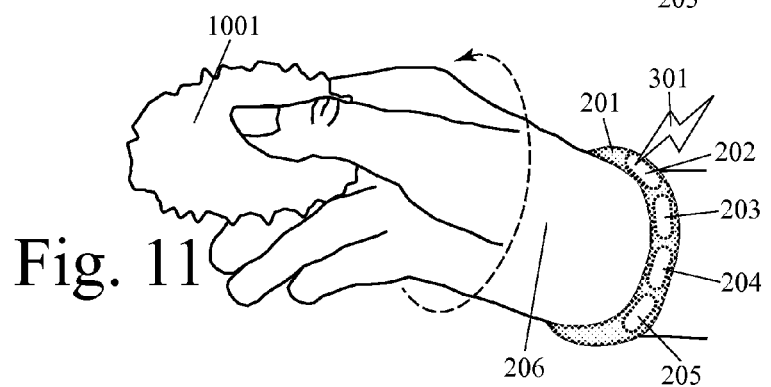
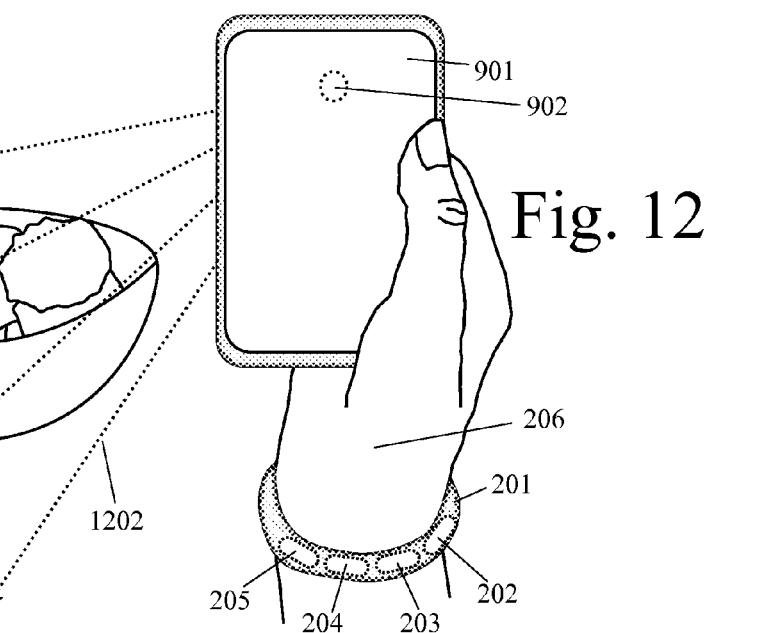

SMART WATCH AND HUMAN-TO-COMPUTER INTERFACE FOR MONITORING FOOD CONSUMPTION

CROSS-REFERENCE TO RELATED APPLICATIONS

This patent application claims the priority benefit of U.S. Provisional Patent Application No. 61/813,780 entitled "Smart Watch that Measures Food Consumption" filed on Apr. 19, 2013 by Robert A. Connor of Medibotics, LLC, the entire contents thereof being incorporated herein by reference. This patent application also claims the priority benefit of U.S. Provisional Patent Application No. 61/825,008 entitled "Smart Watch and Human-to-Computer Interface for Monitoring Food Consumption" filed on May 18, 2013 by Robert A. Connor of Medibotics, LLC, the entire contents thereof being incorporated herein by reference.

FEDERALLY SPONSORED RESEARCH

Not Applicable

SEQUENCE LISTING OR PROGRAM

Not Applicable

BACKGROUND

Field of Invention

This invention relates to energy balance, weight loss, and proper nutrition.

Introduction to Energy Balance and Proper Nutrition

The United States population has some of the highest prevalence rates of obese and overweight people in the world. Further, these rates have increased dramatically during recent decades. In the late 1990's, around one in five Americans was obese. Today, that figure has increased to around one in three. It is estimated that around one in five American children is now obese. The prevalence of Americans who are generally overweight is estimated to be as high as two out of three.

This increase in the prevalence of Americans who are overweight or obese has become one of the most common causes of health problems in the United States. Potential adverse health effects from obesity include: cancer (especially endometrial, breast, prostate, and colon cancers); cardiovascular disease (including heart attack and arterial sclerosis); diabetes (type 2); digestive diseases; gallbladder disease; hypertension; kidney failure; obstructive sleep apnea; orthopedic complications; osteoarthritis; respiratory problems; stroke; metabolic syndrome (including hypertension, abnormal lipid levels, and high blood sugar); impairment of quality of life in general including stigma and discrimination; and even death.

There are estimated to be over a quarter-million obesity-related deaths each year in the United States. The tangible costs to American society of obesity have been estimated at over $100 billion dollars per year. This does not include the intangible costs of human pain and suffering. Despite the considerable effort that has been focused on developing new approaches for preventing and treating obesity, the problem is growing. There remains a serious unmet need for new ways to help people to moderate their consumption of unhealthy food, better manage their energy balance, and lose weight in a healthy and sustainable manner.

Obesity is a complex disorder with multiple interacting causal factors including genetic factors, environmental factors, and behavioral factors. A person's behavioral factors include the person's caloric intake (the types and quantities of food which the person consumes) and caloric expenditure (the calories that the person burns in regular activities and exercise). Energy balance is the net difference between caloric intake and caloric expenditure. Other factors being equal, energy balance surplus (caloric intake greater than caloric expenditure) causes weight gain and energy balance deficit (caloric intake less than caloric expenditure) causes weight loss.

Since many factors contribute to obesity, good approaches to weight management are comprehensive in nature. Proper nutrition and management of caloric intake are key parts of a comprehensive approach to weight management. Consumption of "junk food" that is high in simple sugars and saturated fats has increased dramatically during the past couple decades, particularly in the United States. This has contributed significantly to the obesity epidemic. For many people, relying on willpower and dieting is not sufficient to moderate their consumption of unhealthy "junk food." The results are dire consequences for their health and well-being.

CATEGORIZATION AND REVIEW OF THE PRIOR ART

Introduction to Categorization and Review of the Prior Art

One of the most important methods for addressing the growing problem of obesity is monitoring and modifying a person's net energy balance. A person's net energy balance is their caloric intake minus their caloric expenditure during a period of time. When a person's caloric intake is greater than their caloric expenditure over time, then they have an energy balance surplus and will gain weight. When a person's caloric intake is less than their caloric expenditure over time, then they have an energy balance deficit and will lose weight. In many nations of the world today, including the United States, energy balance surplus and accompanying weight gain is a serious problem for many people.

To help address this problem, there is a need for better devices and methods for monitoring and measuring a person's caloric intake and caloric expenditure as part of an overall approach to energy balance, weight management, and proper nutrition. There has been considerable success in the development of devices and methods for automatically monitoring and measuring caloric expenditure. This is especially true of recent advances in increasingly-sophisticated wearable fitness devices for tracking caloric expenditure activities. These devices range from simple pedometers to innovative wearable fitness monitors and exercise-tracking smart watches. Most of these fitness devices include a wearable accelerometer to track body motion. Some such devices also have other wearable sensors that measure heart rate, blood pressure, temperature, electromagnetic signals from the body, and/or other physiological parameters.

However, measurement of the caloric intake side of the energy balance equation is the weak link in devices and methods for energy balance and weight management. Thus far, monitoring and measuring food consumption has proven to be more challenging than monitoring and measuring caloric expenditure activities. This is particularly troublesome because there is some evidence that the obesity epidemic in the United States is being disproportionately caused by changes in diet.

One possible solution to address this weak link is to use an implantable device for monitoring and measuring a person's food consumption. In an example, an implantable device can monitor physiological signals from organs along a person's gastrointestinal tract. An advantage of such an implantable device is that it does not depend on voluntary action by the person in order to track food consumption. An implantable device can operate automatically and continuously so that user compliance is not a problem.

Although there is a role for implantable devices in monitoring and measuring food consumption, implantable devices are not for everyone. For many people, the cost and potential complications of surgery for implantation make implantable devices less than optimal. There remains a need for a relatively-accurate external device for monitoring and measuring food consumption. Accordingly, the invention disclosed herein is an external, non-implantable device and this review focuses almost entirely on external, non-implantable devices in the prior art.

There is a central dilemma that is confounding the development of external devices for monitoring and measuring a person's food consumption. This dilemma has not yet been solved by the prior art. This dilemma is the tradeoff between personal privacy and food measurement accuracy.

On the one hand, one can create an external device that can be very accurate in monitoring and measuring a person's food consumption, but it will be highly-intrusive with respect to the privacy of the person being monitored and other people nearby. For example, one can create a video imaging device that a person wears continually on their head, neck, or torso. This wearable imaging device can continually take video images of the space surrounding the person. Then these video images can be automatically analyzed to detect eating events and to identify the types of foods that the person consumes. However, continuous video monitoring of the space surrounding a person can be highly-intrusive with respect to the person's privacy and also the privacy of other people nearby.

On the other hand, one can create an external device that is relatively non-intrusive with respect to a person's privacy, but whose accuracy depends completely on the person's compliance in using the device every time that the person eats a meal or snack. For example, one can create a mobile phone application with a menu-driven human-to-computer interface which helps the person to enter information concerning food that they consume. Such an application can also enable a person to use the phone to take pictures of food. These food pictures can then be analyzed to identify the foods that the person consumes. However, the accuracy of such methods based on non-wearable devices depends entirely on the degree of consistency with which the person uses the device every time that they eat a meal or snack. If the person neglects to use the device during a midnight snack or is too embarrassed to use the device in a social dining setting, then the accuracy of food consumption measurement suffers.

In the invention disclosure sections which follow later in this disclosure, I will discuss how the invention herein solves this dilemma of personal privacy vs. food measurement accuracy. Before disclosing this invention, however, it is useful to first thoroughly review the related prior art and to identify its limitations. That is what I do in this categorization and review of the prior art. Then, when I disclose the invention later, it will be clear how this invention addresses the limitations of the prior art. There is a large amount of excellent and innovative prior art in this field. Thus far, however, none of it appears to fully resolve this dilemma of personal privacy vs. food measurement accuracy.

As part of this review, I have categorized the relevant prior art into general categories. There are five general categories of prior art and a sixth miscellaneous category. With the complexity of this field and the volume of patents therein, seeking to categorize all relevant examples of prior art into discrete categories is challenging. Some examples of prior art span multiple categories and no categorization scheme is perfect.

However, even an imperfect categorization scheme can serve a useful purpose for reviewing the prior art. This is especially true when there is a large quantity of relevant prior art. In the categorization and review of the prior art herein, I have identified and classified over 500 examples of prior art. Writing up individual reviews for each of these 500+ examples would be prohibitively lengthy and would also be less useful for the reader, who would have to wade through these 500+ individual reviews. It is more efficient for the reader to be presented with these 500+ examples of prior art having been grouped into six general categories, wherein these six general categories are then reviewed and discussed. To help readers who may wish to dig further into examples within a particular category or to second guess my categorization scheme, I also provide relatively-detailed information on each example of the prior art, including the patent (application) title and date in addition to the inventors and patent (application) number.

The six categories which I use to categorize the 500+ examples of prior art for this review are as follows: (1) non-wearable devices primarily to help measure food consumption; (2) wearable devices primarily to monitor and measure caloric expenditure activities; (3) wearable devices primarily to monitor and measure food consumption; (4) wearable devices to monitor caloric expenditure activities and to help measure food consumption; (5) wearable devices to monitor and measure both caloric expenditure activities and food consumption; and (6) other potentially-relevant devices and methods.

In general, non-wearable devices that help a person to measure their food consumption depend on voluntary action by the person in association with each specific eating event. These non-wearable devices tend to be relatively non-intrusive with respect to privacy, but can suffer from low accuracy if a person does not use them consistently for every meal and snack. In general, there are few current wearable devices for automatically detecting food consumption and these current devices are not very accurate for identifying the specific types of foods that the person consumes. Future generations of wearable devices will probably be more accurate in identifying which specific foods the person consumes, but may also be highly-intrusive with respect to privacy.

The main focus of this invention is on the measurement of food consumption. This is currently the weak link in energy balance measurement. However, devices and methods for measuring caloric expenditure activities, including pedometers and other fitness devices, are also included in this categorization scheme. This is because I believe that there will be increasing convergence of food consumption measurement and caloric expenditure measurement into combined energy balance devices. This makes sense because net energy balance is a function of both energy intake and energy expenditure. This is why, for example, I have included a category in this review for wearable fitness devices which monitor and measure only caloric expenditure activities, even though the primary focus of this invention is on monitoring and measuring food consumption. I now review each of the six categories of prior art.

(1) Non-Wearable Devices Primarily to Help Measure Food Consumption

There are a wide variety of non-wearable devices and methods in the prior art that are intended primarily to help a person measure their food consumption. Since these devices are not worn by a person and do not automatically monitor the person's activities, they require some type of voluntary action by the person in association with each eating event (apart from the actual act of eating).

For decades, many people manually kept track of what foods they ate and/or the associated calories (often called a "food log," "diet log," or "calorie counting") using a pencil and paper. With the development of personal computers, mobile electronic devices, and smart phone applications, much of this manual food consumption tracking has been made easier with menu-driven human-to-computer interfaces that help people to more easily enter information concerning what food they eat. Databases of common foods and their associated nutritional information (including calories) have made calorie counting easier by automatically associating calories with foods entered.

Today, there are mobile phone applications that enable people to manually enter information concerning what foods they eat. Some of these applications also offer automatic analysis of pictures that people take of food in order to at least partially automate the process of identifying the types and amounts of food consumed. The human-to-computer interfaces of such food-logging applications are evolving from keyboards and keypads to touch screens, speech recognition, and gesture recognition. However, these approaches all rely on voluntary human action. Their accuracy is limited by: the degree to which the person consistently uses the device for each meal or snack; and the accuracy with which the person and/or device evaluates the types and amounts of food consumed when the device is actually used.

Although mobile phone food tracking applications are a popular form of device in this category, there are a wide variety of other devices and methods in this category beyond such mobile phone applications. Examples of devices and methods in this category include: specialized portable computing devices that help a person to manual enter food consumption information to create a food log; food databases that automatically link manually-entered foods with nutritional parameters (e.g. calories or nutrient types) associated with those foods; mobile phone applications with menu-driven human-to-computer interfaces for entering food consumption information (e.g. via keypad, touch screen, speech recognition, or gesture recognition); imaging devices and image-analysis systems that enable automatic analysis of food pictures to identify the types and amounts of food in a picture; non-worn food-imaging devices that use bar codes or other packaging codes to identify foods; non-worn food-imaging devices that use food logos or other packaging patterns to identify foods; interactive food logging and meal planning websites and software; smart cards and other systems based on financial transitions that track food purchases; devices that receive information from RFID tags associated with food; computerized food scales, food-weighing dishes and utensils; utensils and accessories designed to track or modify eating speed; smart food utensils or accessories that measure food weight and/or analyze food content; food utensils and containers that track or modify food portions; and smart food containers that track their contents and/or limit access times. Specific limitations of such devices in the prior art include the following.

Specialized hand-held computing devices for measuring food consumption are limited by whether a person wants to carry around a (separate) specialized electronic device, whether the person will consistently use it for every meal or snack they eat, and how skilled the person is in evaluating the amounts and types of food consumed. Food databases are limited when a person eats foods prepared at a home or restaurant for which portion size and ingredients are not standardized. Mobile phone applications are limited by whether a person consistently uses them for every meal or snack and by how accurate the person is in identifying the portion sizes and ingredients of non-standard foods consumed.

Non-worn imaging devices and image analysis systems are limited by whether a person consistently uses them for every meal or snack, problems in identifying food obscured from view (such as in a cup or bowl), and foods that look similar but have different nutritional compositions. Also, such devices and methods can be time-consuming, easy to circumvent, and embarrassing to use in social dining situations. Further, even if a person does consistently take pictures of every meal or snack that they eat, they may be tempted to postpone food identification for hours or days after a meal has occurred. This can cause inaccuracy. How many chips were left in that bag in the picture? Is that a "before" or "after" picture of that half-gallon of ice cream?

Non-worn food-imaging devices that use bar codes or other packaging information to identify foods are limited because not all foods that people eat have such codes and because people may not eat all food that they purchase or otherwise scan into a system. Some of the food in a given package may be thrown out. Interactive food logging and meal planning websites can be helpful, but they depend heavily on information entry compliance and food consumption recall, which can be problematic.

Smart cards and other systems that are based on financial transitions that track food purchases are limited because people purchase food that they do not eat (e.g. for their family) and eat food that they do not purchase (e.g. at home or as a guest). Also, depending on the longevity of food storage, some food may be eaten soon after purchase and some may be eaten long afterwards. Computerized food scales and food-weighing dishes and utensils are limited because they rely on a person using them consistently for all eating events and because some types of food consumption are not conducive to the use of a dish or utensil. Also, such devices and methods can be time-consuming, easy to circumvent, and embarrassing to use in social dining situations.

Utensils and accessories that are designed to track or modify eating speed can be useful, but depend on consistent use of the device and do not shed light on what types of food the person is eating. Smart food utensils or accessories that measure food weight or analyze food content are limited by the consistency of a person's use of the device. Smart food containers that track their contents and/or limit access times depend on the person's exclusive use of such containers for all food that they eat, which can be problematic.

Specific examples of potentially-relevant prior art which appear to be most appropriately classified into this category include the following U.S. Pat. No. 4,207,673 (DiGirolamo et al., Jun. 17, 1980, "Cuttlery"); U.S. Pat. No. 4,212,079 (Segar et al., Jul. 8, 1980, "Electronic Calorie Counter"); U.S. Pat. No. 4,218,611 (Cannon, Aug. 19, 1980, "Method and Apparatus for Controlling Eating Behavior"); U.S. Pat.

No. 4,321,674 (Krames et al., Mar. 23, 1982, "Nutritional Value Accumulating and Display Device"); U.S. Pat. No. 4,650,218 (Hawke, Mar. 17, 1987, "Method and Apparatus for Controlling Caloric Intake"); U.S. Pat. No. 4,686,624 (Blum et al., Aug. 11, 1987, "Portable Apparatus for Acquiring and Processing Data Relative to the Dietetics and/or the Health of a Person"); U.S. Pat. No. 4,796,182 (Duboff, Jan. 3, 1989, "Diet Monitor and Display Device"); U.S. Pat. No. 4,875,533 (Mihara et al., Oct. 24, 1989, "Automatic Weight Detecting Device"); U.S. Pat. No. 4,891,756 (Williams, Jan. 2, 1990, "Nutritional Microcomputer and Method"); U.S. Pat. No. 4,911,256 (Attikiouzel, Mar. 27, 1990, "Dietetic Measurement Apparatus"); U.S. Pat. No. 4,914,819 (Ash, Apr. 10, 1990, "Eating Utensil for Indicating When Food May be Eaten Therewith and a Method for Using the Utensil"); U.S. Pat. No. 4,951,197 (Mellinger, Aug. 21, 1990, "Weight Loss Management System"); U.S. Pat. No. 4,975,682 (Kerr et al., Dec. 4, 1990, "Meal Minder Device"); U.S. Pat. No. 5,033,561 (Hettinger, Jul. 23, 1991, "Diet Control Device"); U.S. Pat. No. 5,173,588 (Harrah, Dec. 22, 1992, "Food Consumption Monitor"); U.S. Pat. No. 5,233,520 (Kretsch et al., Aug. 3, 1993, "Method and System for Measurement of Intake of Foods, Nutrients and Other Food Components in the Diet"); U.S. Pat. No. 5,299,356 (Maxwell, Apr. 5, 1994, "Diet Eating Utensil"); U.S. Pat. No. 5,388,043 (Hettinger, Feb. 7, 1995, "Diet and Behavioral Control Device"); U.S. Pat. No. 5,412,564 (Ecer, May 2, 1995, "System and Method for Diet Control"); U.S. Pat. No. 5,421,089 (Dubus et al., Jun. 6, 1995, "Fork with Timer"); U.S. Pat. No. 5,478,989 (Shepley, Dec. 26, 1995, "Nutritional Information System for Shoppers"); and U.S. Pat. No. 5,542,420 (Goldman et al., Aug. 6, 1996, "Personalized Method and System for Storage, Communication, Analysis, and Processing of Health-Related Data").

Additional U.S. patents which appear to be most appropriately classified into this category include: U.S. Pat. No. 5,673,691 (Abrams et al., Oct. 7, 1997, "Apparatus to Control Diet and Weight Using Human Behavior Modification Techniques"); U.S. Pat. No. 5,691,927 (Gump, Nov. 25, 1997, "Nutritional Aid and Method"); U.S. Pat. No. 5,704,350 (Williams, Jan. 6, 1998, "Nutritional Microcomputer and Method"); U.S. Pat. No. 5,729,479 (Golan, Mar. 17, 1998, "Multifunctional Diet Calculator"); U.S. Pat. No. 5,817,006 (Bergh et al., Oct. 6, 1998, "Method and Apparatus for Measurement of Eating Speed"); U.S. Pat. No. 5,819,735 (Mansfield et al., Oct. 13, 1998, "Device and Method for Monitoring Dietary Intake of Calories and Nutrients"); U.S. Pat. No. 5,836,312 (Moore, Nov. 17, 1998, "Computer-Assisted System and Method for Adjudging the Effect of Consumable Intakes on Physiological Parameters"); U.S. Pat. No. 5,839,901 (Karkanen, Nov. 24, 1998, "Integrated Weight Loss Control Method"); U.S. Pat. No. 5,841,115 (Shepley, Nov. 24, 1998, "Nutritional Information System for Shoppers"); U.S. Pat. No. 5,890,128 (Diaz et al., Mar. 30, 1999, "Personalized Hand Held Calorie Computer (ECC)"); U.S. Pat. No. 5,989,188 (Birkhoelzer, Nov. 23, 1999, "Method and Apparatus for Determining the Energy Balance of a Living Subject on the Basis of Energy Used and Nutrition Intake"); U.S. Pat. No. 6,024,281 (Shepley, Feb. 15, 2000, "Nutritional Information System for Shoppers"); U.S. Pat. No. 6,032,676 (Moore, Mar. 7, 2000, "Method for Correlating Consumable Intakes with Physiological Parameters"); U.S. Pat. No. 6,040,531 (Miller-Kovach, Mar. 21, 2000, "Process For Controlling Body Weight"); U.S. Pat. No. 6,083,006 (Coffman, Jul. 4, 2000, "Personalized Nutrition Planning"); U.S. Pat. No. 6,283,914 (Mansfield et al., Sep. 4, 2001, "Device and Method for Monitoring Dietary Intake of Calories and Nutrients"); U.S. Pat. No. 6,290,646 (Cosentino et al., Sep. 18, 2001, "Apparatus and Method for Monitoring and Communicating Wellness Parameters of Ambulatory Patients"); and U.S. Pat. No. 6,336,136 (Harris, Jan. 1, 2002, "Internet Weight Reduction System").

Further U.S. patents in this category include: U.S. Pat. No. 6,341,295 (Stotler, Jan. 22, 2002, "Virtual Reality Integrated Caloric Tabulator"); U.S. Pat. No. 6,454,705 (Cosentino et al., Sep. 24, 2002, "Medical Wellness Parameters Management System, Apparatus and Method"); U.S. Pat. No. 6,478,736 (Mault, Nov. 12, 2002, "Integrated Calorie Management System"); U.S. Pat. No. 6,553,386 (Alabaster, Apr. 22, 2003, "System and Method for Computerized Visual Diet Behavior Analysis and Training"); U.S. Pat. No. 6,694,182 (Yamazaki et al., Feb. 17, 2004, "Wearable Calorie Calculator"); U.S. Pat. No. 6,723,045 (Cosentino et al., Apr. 20, 2004, "Apparatus and Method for Monitoring and Communicating Wellness Parameters of Ambulatory Patients"); U.S. Pat. No. 6,745,214 (Inoue et al., Jun. 1, 2004, "Calorie Control Apparatus with Voice Recognition"); U.S. Pat. No. 6,755,783 (Cosentino et al., Jun. 29, 2004, "Apparatus and Method for Two-Way Communication in a Device for Monitoring and Communicating Wellness Parameters of Ambulatory Patients"); U.S. Pat. No. 6,856,938 (Kurtz, Feb. 15, 2005, "Weight Monitoring Computer"); U.S. Pat. No. 6,878,885 (Miller-Kovach, Apr. 12, 2005, "Process for Controlling Body Weight"); U.S. Pat. No. 6,917,897 (Mork, Jul. 12, 2005, "Food and Exercise Calculator"); U.S. Pat. No. 6,978,221 (Rudy, Dec. 20, 2005, "Computerized Dietetic Scale"); U.S. Pat. No. 7,044,739 (Matson, May 16, 2006, "System for Controlled Nutrition Consumption"); U.S. Pat. No. 7,096,221 (Nakano, Aug. 22, 2006, "Food Information Management System"); U.S. Pat. No. 7,454,002 (Gardner et al., Nov. 18, 2008, "Integrating Personal Data Capturing Functionality into a Portable Computing Device and a Wireless Communication Device"); U.S. Pat. No. 7,500,937 (Hercules, Mar. 10, 2009, "Diet Compliance System"); U.S. Pat. No. 7,550,683 (Daughtry, Jun. 23, 2009, "Portable Digital Plate Scale"); and U.S. Pat. No. 7,577,475 (Cosentino et al., Aug. 18, 2009, "System, Method, and Apparatus for Combining Information from an Implanted Device with Information from a Patient Monitoring Apparatus").

Further U.S. patents in this category include: U.S. Pat. No. 7,736,318 (Cosentino et al., Jun. 15, 2010, "Apparatus and Method for Monitoring and Communicating Wellness Parameters of Ambulatory Patients"); U.S. Pat. No. 7,769,635 (Simons-Nikolova, Aug. 3, 2010, "Weight Management System with Simple Data Input"); U.S. Pat. No. 7,857,730 (Dugan, Dec. 28, 2010, "Methods and Apparatus for Monitoring and Encouraging Health and Fitness"); U.S. Pat. No. 7,899,709 (Allard et al., Mar. 1, 2011, "System and Method for Identification and Tracking of Food Items"); U.S. Pat. No. 7,949,506 (Hill et al., May 24, 2011, "Method for Determining and Compensating for a Weight Loss Energy Gap"); U.S. Pat. No. 7,956,997 (Wang et al., Jun. 7, 2011, "Systems and Methods for Food Safety Detection"); U.S. Pat. No. 7,999,674 (Kamen, Aug. 16, 2011, "Device and Method for Food Management"); U.S. Pat. No. 8,075,451 (Dugan, Dec. 13, 2011, "Methods and Apparatus for Monitoring and Encouraging Health and Fitness"); U.S. Pat. No. 8,087,937 (Peplinski et al., Jan. 3, 2012, "System and Method for Monitoring Weight and Nutrition"); U.S. Pat. No. 8,229,676 (Hyde et al., Jul. 24, 2012, "Food Content Detector"); U.S. Pat. No. 8,285,488 (Hyde et al., Oct. 9, 2012, "Food Content Detector"); U.S. Pat. No. 8,290,712 (Hyde et al., Oct. 16, 2012, "Food Content Detector"); U.S.

Pat. No. 8,294,581 (Kamen, Oct. 23, 2012, "Device and Method for Food Management"); U.S. Pat. No. 8,299,930 (Schmid-Schonbein et al., Oct. 30, 2012, "Devices, Systems and Methods to Control Caloric Intake"); U.S. Pat. No. 8,321,141 (Hyde et al., Nov. 27, 2012, "Food Content Detector"); U.S. Pat. No. 8,330,057 (Sharawi et al., Dec. 11, 2012, "System and Method for Weighing Food and Calculating Calorie Content Thereof"); U.S. Pat. No. 8,337,367 (Dugan, Dec. 25, 2013, "Methods and Apparatus for Monitoring and Encouraging Health and Fitness"); U.S. Pat. No. 8,345,930 (Tamrakar et al., Jan. 1, 2013, "Method for Computing Food Volume in a Method for Analyzing Food"); U.S. Pat. No. 8,355,875 (Hyde et al., Jan. 15, 2013, "Food Content Detector"); U.S. Pat. No. 8,363,913 (Boushey et al., Jan. 29, 2013, "Dietary Assessment System and Method"); U.S. Pat. No. 8,386,185 (Hyde et al., May 20, 2010, "Food Content Detector"); U.S. Pat. No. 8,392,123 (Hyde et al., May 20, 2010, "Food Content Detector"); U.S. Pat. No. 8,392,124 (Hyde et al., May 20, 2010, "Food Content Detector"); U.S. Pat. No. 8,392,125 (Hyde et al., Mar. 5, 2013, "Food Content Detector"); U.S. Pat. No. 8,396,672 (Hyde et al., Mar. 12, 2013, "Food Content Detector"); and U.S. Pat. No. 8,438,038 (Cosentino et al., May 7, 2013, "Weight Loss or Weight Management System").

Specific examples of potentially-relevant prior art which appear to be most appropriately classified into this category also include the following U.S. patent applications: 20020062069 (Mault, May 23, 2002, "System and Method of Integrated Calorie Management Using Interactive Television"); 20020124017 (Mault, Sep. 5, 2002, "Personal Digital Assistant with Food Scale Accessory"); 20020167863 (Davis et al., Nov. 14, 2002, "Portable, Compact Device to Monitor Rate and Quantity of Dietary Intake to Control Body Weight"); 20030076983 (Cox, Apr. 24, 2003, "Personal Food Analyzer"); 20030152607 (Mault, Aug. 14, 2003, "Caloric Management System and Method with Voice Recognition"); 20030163354 (Shamoun, Aug. 28, 2003, "Device for Collecting and Analyzing Nutritional Data and Method Therefor"); 20030165799 (Bisogno, Sep. 4, 2003, "Computer Program, Method, and System for Monitoring Nutrition Content of Consumables and for Facilitating Menu Planning"); 20030219513 (Gordon, Nov. 27, 2003, "Personal Nutrition Control Method"); 20050008994 (Bisogno, Jan. 13, 2005, "Computer Program, Method, and System for Monitoring Nutrition Content of Consumables and for Facilitating Menu Planning"); 20050011367 (Crow, Jan. 20, 2005, "Portion Control Serving Utensils"); 20050014111 (Matson, Jan. 20, 2005, "System for Controlled Nutrition Consumption"); 20050153052 (Williams et al., Jul. 14, 2005, "Food and Beverage Quality Sensor"); 20050184148 (Perlman, Aug. 25, 2005, "Scale Having Nutritional Information Readouts"); 20050247213 (Slilaty, Nov. 10, 2005, "Method of Identifying Particular Attributes of Food Products Consistent with Consumer Needs and/or Desires"); and 20050266385 (Bisogno, Dec. 1, 2005, "Computer Program, Method, and System for Monitoring Nutrition Content of Consumables and for Facilitating Menu Planning").

Additional U.S. patent applications which appear to be most appropriately classified into this category include: 20060036395 (Shaya et al., Feb. 16, 2006, "Method and Apparatus for Measuring and Controlling Food Intake of an Individual"); 20060074716 (Tilles et al., Apr. 6, 2006, "System and Method for Providing Customized Interactive and Flexible Nutritional Counseling"); 20060189853 (Brown, Aug. 24, 2006, "Method and System for Improving Adherence with a Diet Program or Other Medical Regimen"); 20060229504 (Johnson, Oct. 12, 2006, "Methods and Systems for Lifestyle Management"); 20060263750 (Gordon, Nov. 23, 2006, "Personal Nutrition Control Devices"); 20070021979 (Cosentino et al., Jan. 25, 2007, "Multiuser Wellness Parameter Monitoring System"); 20070027366 (Osburn, Feb. 1, 2007, "Device and System for Entering and Monitoring Dietary Data"); 20070028453 (Crow, Feb. 8, 2007, "Portion Control Serving Utensils"); 20070030339 (Findlay et al., Feb. 8, 2007, "Method, System and Software for Monitoring Compliance"); 20070050058 (Zuziak et al., Mar. 1, 2007, "Placemat for Calculating and Monitoring Calorie Intake"); 20070059672 (Shaw, Mar. 15, 2007, "Nutrition Tracking Systems and Methods"); 20070089335 (Smith et al., Apr. 26, 2007, "Nutrient Consumption/Expenditure Planning and Tracking Apparatus System and Method"); 20070098856 (LePine, May 3, 2007, "Mealtime Eating Regulation Device"); 20070173703 (Lee et al., Jul. 26, 2007, "Method, Apparatus, and Medium for Managing Weight by Using Calorie Consumption Information"); 20070179355 (Rosen, Aug. 2, 2007, "Mobile Self-Management Compliance and Notification Method, System and Computer Program Product"); 20070208593 (Hercules, Sep. 6, 2007, "Diet Compliance System"); 20080019122 (Kramer, Jan. 24, 2008, "Foodware System Having Sensory Stimulating, Sensing and/or Data Processing Components"); 20080060853 (Davidson et al., Mar. 13, 2008, "Scales Displaying Nutritional Information"); and 20080255955 (Simons-Nikolova, Oct. 16, 2008, "Weight Management System with Simple Data Input").

Further U.S. patent applications in this category include: 20080267444 (Simons-Nikolova, Oct. 30, 2008, "Modifying a Person's Eating and Activity Habits"); 20080270324 (Allard et al., Oct. 30, 2008, "System and Method for Identification and Tracking of Food Items"); 20080276461 (Gold, Nov. 13, 2008, "Eating Utensil Capable of Automatic Bite Counting"); 20090112800 (Athsani, Apr. 30, 2009, "System and Method for Visual Contextual Search"); 20090176526 (Altman, Jul. 9, 2009, "Longitudinal Personal Health Management System Using Mobile Data Capture"); 20090191514 (Barnow, Jul. 30, 2009, "Calorie Counter"); 20090219159 (Morgenstern, Sep. 3, 2009, "Method and System for an Electronic Personal Trainer"); 20090253105 (Lepine, Oct. 8, 2009, "Device for Regulating Eating by Measuring Potential"); 20100003647 (Brown et al., Jan. 7, 2010, "System and Method for Automated Meal Recommendations"); 20100057564 (Godsey et al., Mar. 4, 2010, "System and Method for Fitness Motivation"); 20100062119 (Miller-Kovach, Mar. 11, 2010, "Processes and Systems for Achieving and Assisting in Improved Nutrition"); 20100062402 (Miller-Kovach, Mar. 11, 2010, "Processes and Systems Using and Producing Food Healthfulness Data Based on Linear Combinations of Nutrients"); 20100080875 (Miller-Kovach, Apr. 1, 2010, "Processes and Systems for Achieving and Assisting in Improved Nutrition Based on Food Energy Data and Relative Healthfulness Data"); 20100109876 (Schmid-Schonbein et al., May 6, 2010, "Devices, Systems and Methods to Control Caloric Intake"); 20100111383 (Boushey et al., May 6, 2010, "Dietary Assessment System and Method"); 20100125176 (Hyde et al., May 20, 2010, "Food Content Detector"); and 20100125177 (Hyde et al., May 20, 2010, "Food Content Detector").

Further U.S. patent applications in this category include: 20100125178 (Hyde et al., May 20, 2010, "Food Content Detector"); 20100125179 (Hyde et al., May 20, 2010, "Food Content Detector"); 20100125180 (Hyde et al., May 20, 2010, "Food Content Detector"); 20100125181 (Hyde et al., May 20, 2010, "Food Content Detector"); 20100125417 (Hyde et al., May 20, 2010, "Food Content Detector"); 20100125418 (Hyde et al., May 20, 2010, "Food Content Detector"); 20100125419 (Hyde et al., May 20, 2010, "Food Content Detector"); 20100125420 (Hyde et al., May 20, 2010, "Food Content Detector"); 20100173269 (Puri et al., Jul. 8, 2010, "Food Recognition Using Visual Analysis and Speech Recognition"); 20100191155 (Kim et al., Jul. 29, 2010, "Apparatus for Calculating Calories Balance by Classifying User's Activity"); 20100205209 (Jokinen, Aug. 12, 2010, "Method and System for Monitoring a Personal Intake"); 20100332571 (Healey et al., Dec. 30, 2010, "Device Augmented Food Identification"); 20110124978 (Williams, May 26, 2011, "Health and Fitness System"); 20110182477 (Tamrakar et al., Jul. 28, 2011, "Method for Computing Food Volume in a Method for Analyzing Food"); 20110184247 (Contant et al., Jul. 28, 2011, "Comprehensive Management of Human Health"); 20110281245 (Mansour, Nov. 17, 2011, "System for Regulating Caloric Intake and Method for Using Same"); 20110318717 (Adamowicz, Dec. 29, 2011, "Personalized Food Identification and Nutrition Guidance System"); 20120031805 (Stolarczyk, Feb. 9, 2012, "Daily Meal Planning System"); 20120055718 (Chen, Mar. 8, 2012, "Electronic Scale for Recording Health Administration Data"); and 20120072233 (Hanlon et al., Mar. 22, 2012, "Medical Health Information System for Health Assessment, Weight Management and Meal Planning").

Further U.S. patent applications in this category include: 20120077154 (Highet et al., Mar. 29, 2012, "Incrementally-Sized Standard-Sized Eating-Ware System for Weight Management"); 20120083669 (Abujbara, Apr. 5, 2012, "Personal Nutrition and Wellness Advisor"); 20120096405 (Seo, Apr. 19, 2012, "Apparatus and Method for Diet Management"); 20120115111 (Lepine, May 10, 2012, "Mealtime Eating Regulation Device"); 20120126983 (Breibart, May 24, 2012, "Method and Associated Device for Personal Weight Control or Weight Loss"); 20120144912 (Kates et al., Jun. 14, 2012, "Portion Control System for Weight Loss and Maintenance"); 20120170801 (De Oliveira et al., Jul. 5, 2012, "System for Food Recognition Method Using Portable Devices Having Digital Cameras"); 20120178065 (Naghavi et al., Jul. 12, 2012, "Advanced Button Application for Individual Self-Activating and Monitored Control System in Weight Loss Program"); 20120179665 (Baarman et al., Jul. 12, 2012, "Health Monitoring System"); 20120221495 (Landers, Aug. 30, 2012, "Digital Weight Loss Aid"); 20120295233 (Cooperman, Nov. 22, 2012, "Computerized System and Method for Monitoring Food Consumption"); 20120315609 (Miller-Kovach et al., Dec. 13, 2012, "Methods and Systems for Weight Control by Utilizing Visual Tracking of Living Factor(s)"); 20120321759 (Marinkovich et al., Dec. 20, 2012, "Characterization of Food Materials by Optomagnetic Fingerprinting"); 20130006063 (Wang, Jan. 3, 2013, "Physiological Condition, Diet and Exercise Plan Recommendation and Management System"); 20130006802 (Dillahunt et al., Jan. 3, 2013, "Generating a Location-Aware Preference and Restriction-Based Customized Menu"); and 20130006807 (Bai et al., Jan. 3, 2013, "Guideline-Based Food Purchase Management").

Further U.S. patent applications in this category include: 20130012788 (Horseman, Jan. 10, 2013, "Systems, Computer Medium and Computer-Implemented Methods for Monitoring and Improving Biometric Health of Employees"); 20130012789 (Horseman, Jan. 10, 2013, "Systems, Computer Medium and Computer-Implemented Methods for Monitoring and Improving Biomechanical Health of Employees"); 20130012790 (Horseman, Jan. 10, 2013, "Systems, Computer Medium and Computer-Implemented Methods for Monitoring and Improving Health and Productivity of Employees"); 20130012802 (Horseman, Jan. 10, 2013, "Systems, Computer Medium and Computer-Implemented Methods for Monitoring and Improving Cognitive and Emotive Health of Employees"); 20130013331 (Horseman, Jan. 10, 2013, "Systems, Computer Medium and Computer-Implemented Methods for Monitoring Health of Employees Using Mobile Devices"); 20130043997 (Cosentino et al., Feb. 21, 2013, "Weight Loss Or Weight Management System"); 20130043997 (Cosentino et al., Feb. 21, 2013, "Weight Loss or Weight Management System"); 20130045467 (Kamen, Feb. 21, 2013, "Device and Method for Food Management"); 20130090565 (Quy, Apr. 11, 2013, "Method and Apparatus for Monitoring Exercise with Wireless Internet Connectivity"); 20130091454 (Papa et al., Apr. 11, 2013, "Physical Health Application and Method for Implementation"); 20130105565 (Kamprath, May 2, 2013, "Nutritional Information System"); 20130108993 (Katz; David L. May 2, 2013, "Method and System for Scoring a Diet"); and 20130113933 (Boushey et al., May 9, 2013, "Dietary Assessment System and Method"). Prior art which appears to be most appropriately classified into this category also includes WO 1997028738 (Zuabe, Aug. 14, 1997, "Portable Apparatus for Monitoring Food Intake").

(2) Wearable Devices Primarily to Monitor and Measure Caloric Expenditure Activities Although the main focus of this invention is on the monitoring and measurement of food consumption, there are reasons why I have also included this category for wearable fitness devices which primarily or exclusively monitor and measure caloric expenditure activities. First, there has been more progress in the prior art toward automatic monitoring and measuring of caloric expenditure activities than there has been toward automatic monitoring and measuring of caloric intake. There can be lessons learned and cross-over technology between the two sides of the energy balance equation. Second, there will probably be increasing convergence of caloric expenditure and intake measurement into combined energy balance devices. For example, especially for wearable fitness devices that include an accelerometer, it may be possible to use this accelerometer to also monitor for possible eating events (especially if the device is worn on a body member that moves when a person is eating).

Most devices and methods in this category include a wearable accelerometer which is used to analyze a person's movements and/or estimate their caloric expenditure. Some of the more-sophisticated devices also include wearable sensors that measure heart rate, blood pressure, temperature, electromagnetic signals from the body, and/or other physiologic parameters. Some fitness monitors also supplement an accelerometer with an altimeter and GPS functionality.

Most devices and methods in this category measure motion from one location on a person's body, unlike the full-body "motion capture" technology that is used for animation in motion pictures. There is movement toward the use of full-body motion recognition in gaming systems for measuring caloric expenditure, but this is not currently wearable and portable technology. Most wearable and portable technology is still based on measurement of body movement from one location on a person's body. Accordingly, some types of calorie burning activities are more accurately measured than others. For example, although fidgeting burns calories, an accelerometer attached to a person's torso, on their neck, or in their pocket will not measure this type of calorie-burning activity very well.

Although devices and methods in this category can be an important part of monitoring and measuring energy balance, they currently provide very little (if any) monitoring or measurement of a person's food consumption. I did my best to thoroughly review the 500+ examples of prior art and to place into this category those examples which appear to focus primarily on measuring caloric expenditure activities with little (or no) mention of food, nutrition, eating, or caloric intake. However, if I missed a reference to measuring food consumption or caloric intake in the details of one of these examples, then that example could be better classified into either category 4 or 5 which follow. By definition, prior art in this category is very limited in terms of monitoring or measuring food consumption.

Specific examples of potentially-relevant prior art which appear to be most appropriately classified into this category include the following U.S. Pat. No. 4,757,453 (Nasiff, Jul. 12, 1988, "Body Activity Monitor Using Piezoelectric Transducers on Arms and Legs"); U.S. Pat. No. 5,038,792 (Mault, Aug. 13, 1991, "Oxygen Consumption Meter"); U.S. Pat. No. 6,135,951 (Richardson et al., Oct. 24, 2000, "Portable Aerobic Fitness Monitor for Walking and Running"); U.S. Pat. No. 6,498,994 (Vock et al., Dec. 24, 2002, "Systems and Methods for Determining Energy Experienced by a User and Associated With Activity"); U.S. Pat. No. 6,527,711 (Stivoric et al., Mar. 4, 2003, "Wearable Human Physiological Data Sensors and Reporting System Therefor"); U.S. Pat. No. 6,856,934 (Vock et al., Feb. 15, 2005, "Sport Monitoring Systems and Associated Methods"); U.S. Pat. No. 7,054,784 (Flentov et al., May 30, 2006, "Sport Monitoring Systems"); U.S. Pat. No. 7,057,551 (Vogt, Jun. 6, 2006, "Electronic Exercise Monitor and Method Using a Location Determining Component and a Pedometer"); U.S. Pat. No. 7,153,262 (Stivoric et al., Dec. 26, 2006, "Wearable Human Physiological Data Sensors and Reporting System Therefor"); U.S. Pat. No. 7,255,437 (Howell et al., Aug. 14, 2007, "Eyeglasses with Activity Monitoring"); U.S. Pat. No. 7,373,820 (James, May 20, 2008, "Accelerometer for Data Collection and Communication"); U.S. Pat. No. 7,398,151 (Burrell et al., Jul. 8, 2008, "Wearable Electronic Device"); U.S. Pat. No. 7,401,918 (Howell et al., Jul. 22, 2008, "Eyeglasses with Activity Monitoring"); U.S. Pat. No. 7,438,410 (Howell et al., Oct. 21, 2008, "Tethered Electrical Components for Eyeglasses"); U.S. Pat. No. 7,451,056 (Flentov et al., Nov. 11, 2008, "Activity Monitoring Systems and Methods"); U.S. Pat. No. 7,481,531 (Howell et al., Jan. 27, 2009, "Eyeglasses with User Monitoring"); U.S. Pat. No. 7,512,515 (Vock et al., Mar. 31, 2009, "Activity Monitoring Systems and Methods"); U.S. Pat. No. 7,640,804 (Daumer et al., Jan. 5, 2010, "Apparatus for Measuring Activity"); and U.S. Pat. No. 7,717,866 (Damen, May 18, 2010, "Portable Device Comprising an Acceleration Sensor and Method of Generating Instructions or Advice").

Additional U.S. patents which appear to be most appropriately classified into this category include: U.S. Pat. No. 7,805,196 (Miesel et al., Sep. 28, 2010, "Collecting Activity Information to Evaluate Therapy"); U.S. Pat. No. 7,841,966 (Aaron et al., Nov. 30, 2010, "Methods, Systems, and Products for Monitoring Athletic Performance"); U.S. Pat. No. 7,980,997 (Thukral et al., Jul. 19, 2011, "System for Encouraging a User to Perform Substantial Physical Activity"); U.S. Pat. No. 8,021,297 (Aerts, Sep. 20, 2011, "Wearable Device"); U.S. Pat. No. 8,033,959 (Oleson et al., Oct. 11, 2011, "Portable Fitness Monitoring Systems, and Applications Thereof"); U.S. Pat. No. 8,068,858 (Werner et al., Nov. 29, 2011, "Methods and Computer Program Products for Providing Information about a User During a Physical Activity"); U.S. Pat. No. 8,162,804 (Tagliabue, Apr. 24, 2012, "Collection and Display of Athletic Information"); U.S. Pat. No. 8,184,070 (Taubman, May 22, 2012, "Method and System for Selecting a User Interface for a Wearable Computing Device"); U.S. Pat. No. 8,244,278 (Werner et al., Aug. 14, 2012, "Portable Fitness Systems, and Applications Thereof"); U.S. Pat. No. 8,265,907 (Nanikashvili et al., Sep. 11, 2012, "System and a Method for Physiological Monitoring"); U.S. Pat. No. 8,352,211 (Vock et al., Jan. 8, 2013, "Activity Monitoring Systems and Methods"); U.S. Pat. No. 8,370,549 (Burton et al., Feb. 5, 2013, "Wearable Device Assembly Having Athletic Functionality"); U.S. Pat. No. 8,378,811 (Crump et al., Feb. 19, 2013, "Mobile Wireless Customizable Health and Condition Monitor"); U.S. Pat. No. 8,403,845 (Stivoric et al., Mar. 26, 2013, "Wearable Human Physiological and Environmental Data Sensors and Reporting System Therefor"); U.S. Pat. No. 8,408,436 (Berry et al., Apr. 2, 2013, "Wearable Device Assembly Having Athletic Functionality"); U.S. Pat. No. 8,416,102 (Yin Apr. 9, 2013, "Activity Monitoring System Insensitive to Accelerations Induced by External Motion Factors"); and U.S. Pat. No. 8,421,620 (Boyd et al., Apr. 16, 2013, "Electronically Triggered Personal Athletic Device").

Specific examples of potentially-relevant prior art which appear to be most appropriately classified into this category also include the following U.S. patent applications: 20110288379 (Wu, Nov. 24, 2011, "Body Sign Dynamically Monitoring System"); 20120004883 (Vock et al., Jan. 5, 2012, "Activity Monitoring Systems and Methods"); 20120150074 (Yanev et al., Jun. 14, 2012, "Physical Activity Monitoring System"); 20120150327 (Altman et al., Jun. 14, 2012, "System, Method, Apparatus, or Computer Program Product for Exercise and Personal Security"); 20120245716 (Srinivasan et al., Sep. 27, 2012, "Activity Monitoring Device and Method"); 20120251079 (Meschter et al., Oct. 4, 2012, "Systems and Methods for Time-Based Athletic Activity Measurement and Display"); 20120253485 (Weast et al., Oct. 4, 2012, "Wearable Device Having Athletic Functionality"); 20120258433 (Hope et al., Oct. 11, 2012, "Fitness Monitoring Methods, Systems, and Program Products, and Applications Thereof"); 20120268592 (Aragones et al., Oct. 25, 2012, "Processing Data of a User Performing an Athletic Activity to Estimate Energy Expenditure"); 20120274508 (Brown et al., Nov. 1, 2012, "Athletic Watch"); 20120274554 (Kinoshita et al., Nov. 1, 2012, "Body Movement Detection Device and Display Control Method of Body Movement Detection Device"); 20120283855 (Hoffman et al., Nov. 8, 2012, "Monitoring Fitness Using a Mobile Device"); 20120289867 (Kasama, Nov. 15, 2012, "State Determining Device and State Determination Method"); 20120290109 (Engelberg et al., Nov. 15, 2012, "Methods and Systems for Encouraging Athletic Activity"); 20120310971 (Tran, Dec. 6, 2012, "Fitness Device"); 20120316406 (Rahman et al., Dec. 13, 2012, "Wearable Device and Platform for Sensory Input"); 20120316455 (Rahman et al., Dec. 13, 2012, "Wearable Device and Platform for Sensory Input"); and 20120316456 (Rahman et al., Dec. 13, 2012, "Sensory User Interface").

Additional U.S. patent applications which appear to be most appropriately classified into this category include: 20120316471 (Rahman et al., Dec. 13, 2012, "Power Management in a Data-Capable Strapband"); 20120316661 (Rahman et al., Dec. 13, 2012, "Media Device, Application, and Content Management Using Sensory Input"); 20120317430 (Rahman et al., Dec. 13, 2012, "Power Management in a Data-Capable Strapband"); 20120323346

(Ashby et al., Dec. 20, 2012, "Portable Physical Activity Sensing System"); 20120323496 (Burroughs et al., Dec. 20, 2012, "Tracking of User Performance Metrics During a Workout Session"); 20130005534 (Rosenbaum, Jan. 3, 2013, "Instrumented Article of Fitness and Method of Determining Caloric Requirements"); 20130006583 (Weast et al., Jan. 3, 2013, "Sensor-Based Athletic Activity Measurements"); 20130041617 (Pease et al., Feb. 14, 2013, "Systems and Methods for Monitoring Athletic Performance"); 20130052623 (Thukral et al., Feb. 28, 2013, "System for Encouraging a User to Perform Substantial Physical Activity"); 20130053990 (Ackland, Feb. 28, 2013, "Classification System and Method"); 20130073368 (Squires, Mar. 21, 2013, "Incentivizing Physical Activity"); 20130083009 (Geisner et al., Apr. 4, 2013, "Exercising Applications for Personal Audio/Visual System"); 20130102387 (Barsoum et al., Apr. 25, 2013, "Calculating Metabolic Equivalence with a Computing Device"); 20130103416 (Amigo et al., Apr. 25, 2013, "Systems and Methods for Activity Evaluation"); 20130106603 (Weast et al., May 2, 2013, "Wearable Device Assembly Having Athletic Functionality"); 20130106684 (Weast et al., May 2, 2013, "Wearable Device Assembly Having Athletic Functionality"); 20130110011 (McGregor et al., May 2, 2013, "Method of Monitoring Human Body Movement"); 20130110264 (Weast et al., May 2, 2013, "Wearable Device Having Athletic Functionality"); 20130115583 (Gordon et al., May 9, 2013, "User Interface for Remote Joint Workout Session"); and 20130115584 (Gordon et al., May 9, 2013, "User Interface and Fitness Meters for Remote Joint Workout Session").

(3) Wearable Devices Primarily to Monitor and Measure Food Consumption

Devices and methods in the previous category (category 2) focus primarily or exclusively on the caloric expenditure side of the energy balance equation. Devices and methods in this present category (category 3) focus primarily or exclusively on the caloric intake side of energy balance. Prior art in this present category includes wearable devices that are primarily for monitoring and measuring food consumption. In general, there has been less progress on the caloric intake side of the equation. Also, most devices that offer automatic monitoring and measurement of food consumption also offer at least some monitoring and measurement of caloric expenditure activities. Wearable devices that offer at least some measurement of both food consumption and caloric expenditure activities are classified in categories 4 or 5 which follow.

Examples of devices and methods in this category include: wearable accelerometers or other motion sensors that detect body motions associated with eating (e.g. particular patterns of hand movements or mouth movements); wearable heart rate, blood pressure, and/or electromagnetic body signal monitors that are used to detect eating events; wearable thermal energy sensors that are used to detect eating events; wearable glucose monitors that are used to detect eating events and provide some information about the nutritional composition of food consumed; wearable body fluid sampling devices such as continuous micro-sampling blood analysis devices; wearable sound sensors that detect body sounds or environmental sounds associated with eating events (e.g. chewing sounds, swallowing sounds, gastrointestinal organ sounds, and verbal food orders); and wearable cameras that continually take video images of the space surrounding the person wherein these video images are analyzed to detect eating events and identify foods consumed.

As mentioned previously, the prior art for devices and methods for wearable food consumption monitoring is generally less well-developed than the prior art for wearable caloric expenditure monitoring. Most of the prior art in this category offers some indication of eating events, but not very good identification of the specific amounts and types of food that a person eats. For example, a wrist-mounted accelerometer may be able to generally count the number of mouthfuls of food that a person consumes, but does not shed light on what type of food that person is eating. The same limitation is generally true for wearable heart rate, blood pressure, temperature, and electromagnetic monitors. Wearable continuous glucose monitors can provide more information than the preceding monitors, but still fall far short of creating a complete food consumption log for energy balance and nutritional purposes.

Wearable video imaging devices that continually record video images of the space surrounding a person have the potential to offer much more accurate detection of eating and identification of the types and amounts of food consumed. However, as we have discussed, such devices can also be highly-intrusive with respect to the privacy of the person being monitored and also everyone around them. This privacy concern can be a serious limitation for the use of a wearable video imaging device for monitoring and measuring food consumption. Since most developers of wearable video imaging devices appear to be developing such devices for many more applications than just monitoring food consumption, most such prior art is not categorized into this category.

Specific examples of potentially-relevant prior art which appear to be most appropriately classified into this category include the following U.S. Pat. No. 4,100,401 (Tutt et al., Jul. 11, 1978, "Calorie Calculator-Chronometer"); U.S. Pat. No. 4,192,000 (Lipsey, Mar. 4, 1980, "Electronic Calorie Counter"); U.S. Pat. No. 4,509,531 (Ward, Apr. 9, 1985, "Personal Physiological Monitor"); U.S. Pat. No. 4,823,808 (Clegg et al., Apr. 25, 1989, "Method for Control of Obesity Overweight and Eating Disorders"); U.S. Pat. No. 4,965,553 (DelBiondo et al., Oct. 23, 1990, "Hand-Near-Mouth Warning Device"); U.S. Pat. No. 5,050,612 (Matsumura, Sep. 24, 1991, "Device for Computer-Assisted Monitoring of the Body"); U.S. Pat. No. 5,067,488 (Fukada et al., Nov. 26, 1991, "Mastication Detector and Measurement Apparatus and Method of Measuring Mastication"); U.S. Pat. No. 5,263,491 (Thornton, Nov. 23, 1993, "Ambulatory Metabolic Monitor"); U.S. Pat. No. 5,398,688 (Laniado, Mar. 21, 1995, "Method, System and Instrument for Monitoring Food Intake"); U.S. Pat. No. 5,424,719 (Ravid, Jun. 13, 1995, "Consumption Control"); U.S. Pat. No. 5,497,772 (Schulman et al., Mar. 12, 1996, "Glucose Monitoring System"); U.S. Pat. No. 5,563,850 (Hanapole, Oct. 8, 1996, "Food Intake Timer"); U.S. Pat. No. 6,135,950 (Adams, Oct. 24, 2000, "E-fit Monitor"); U.S. Pat. No. 6,249,697 (Asano, Jun. 19, 2001, "Electrogastrograph and Method for Analyzing Data Obtained by the Electrogastrograph"); U.S. Pat. No. 6,425,862 (Brown, Jul. 30, 2002, "Interactive Furniture for Dieters"); U.S. Pat. No. 6,508,762 (Karnieli, Jan. 21, 2003, "Method for Monitoring Food Intake"); and U.S. Pat. No. 6,893,406 (Takeuchi et al., May 17, 2005, "Mastication Monitoring Device").

Additional U.S. patents which appear to be most appropriately classified into this category include: U.S. Pat. No. 7,855,936 (Czarnek et al., Dec. 21, 2010, "Diet Watch"); U.S. Pat. No. 7,878,975 (Liljeryd et al., Feb. 1, 2011, "Metabolic Monitoring, a Method and Apparatus for Indicating a Health-Related Condition of a Subject"); U.S. Pat.

No. 8,112,281 (Yeung et al., Feb. 7, 2012, "Accelerometer-Based Control of Wearable Audio Recorders"); U.S. Pat. No. 8,158,082 (Imran, Apr. 17, 2012, "Micro-Fluidic Device"); U.S. Pat. No. 8,236,242 (Drucker et al., Aug. 7, 2012, "Blood Glucose Tracking Apparatus and Methods"); U.S. Pat. No. 8,275,438 (Simpson et al., Sep. 25, 2012, "Analyte Sensor"); U.S. Pat. No. 8,280,476 (Jina, Oct. 2, 2012, "Devices, Systems, Methods and Tools for Continuous Glucose Monitoring"); U.S. Pat. No. 8,287,453 (Li et al., Oct. 16, 2012, "Analyte Sensor"); U.S. Pat. No. 8,298,142 (Simpson et al., Oct. 30, 2012, "Analyte Sensor"); U.S. Pat. No. 8,310,368 (Hoover et al., Nov. 13, 2012, "Weight Control Device"); U.S. Pat. No. 8,369,919 (Kamath et al., Feb. 5, 2013, "Systems and Methods for Processing Sensor Data"); U.S. Pat. No. 8,417,312 (Kamath et al., Apr. 9, 2013, "Systems and Methods for Processing Sensor Data"); and U.S. Pat. No. 8,423,113 (Shariati et al., Apr. 16, 2013, "Systems and Methods for Processing Sensor Data"); U.S. Pat. No. 8,438,163 (Li et al., May 7, 2013, "Automatic Learning of Logos for Visual Recognition").

Specific examples of potentially-relevant prior art which appear to be most appropriately classified into this category also include the following U.S. patent applications: 20020022774 (Karnieli, Feb. 21, 2002, "Method for Monitoring Food Intake"); 20040073142 (Takeuchi et al., Apr. 15, 2004, "Mastication Monitoring Device"); 20050283096 (Chau et al., Dec. 22, 2005, "Apparatus and Method for Detecting Swallowing Activity"); 20060197670 (Breibart, Sep. 7, 2006, "Method and Associated Device for Personal Weight Control"); 20080137486 (Czarenk et al., Jun. 12, 2008, "Diet Watch"); 20080262557 (Brown, Oct. 23, 2008, "Obesity Management System"); 20100194573 (Hoover et al., Aug. 5, 2010, "Weight Control Device"); 20100240962 (Contant, Sep. 23, 2010, "Eating Utensil to Monitor and Regulate Dietary Intake"); 20120078071 (Bohm et al., Mar. 29, 2012, "Advanced Continuous Analyte Monitoring System"); 20120149996 (Stivoric et al., Jun. 14, 2012, "Method and Apparatus for Providing Derived Glucose Information Utilizing Physiological and/or Contextual Parameters"); 20120149996 (Stivoric et al., Jun. 14, 2012, "Method and Apparatus for Providing Derived Glucose Information Utilizing Physiological and/or Contextual Parameters"); 20120191052 (Rao, Jul. 26, 2012, "Intelligent Activated Skin Patch System"); 20120194418 (Osterhout et al., Aug. 2, 2012, "AR Glasses with User Action Control and Event Input Based Control of Eyepiece Application"); 20120194419 (Osterhout et al., Aug. 2, 2012, "AR Glasses with Event and User Action Control of External Applications"); and 20120194420 (Osterhout et al., Aug. 2, 2012, "AR Glasses with Event Triggered User Action Control of AR Eyepiece Facility").

Additional U.S. patent applications which appear to be most appropriately classified into this category include: 20120194549 (Osterhout et al., Aug. 2, 2012, "AR Glasses Specific User Interface Based on a Connected External Device Type"); 20120194550 (Osterhout et al., Aug. 2, 2012, "Sensor-Based Command and Control of External Devices with Feedback from the External Device to the AR Glasses"); 20120194551 (Osterhout et al., Aug. 2, 2012, "AR Glasses with User-Action Based Command and Control of External Devices"); 20120194552 (Osterhout et al., Aug. 2, 2012, "AR Glasses with Predictive Control of External Device Based on Event Input"); 20120194553 (Osterhout et al., Aug. 2, 2012, "AR Glasses with Sensor and User Action Based Control of External Devices with Feedback"); 20120200488 (Osterhout et al., Aug. 9, 2012, "AR Glasses with Sensor and User Action Based Control of Eyepiece Applications with Feedback"); 20120200499 (Osterhout et al., Aug. 9, 2012, "AR Glasses with Event, Sensor, and User Action Based Control of Applications Resident on External Devices with Feedback"); 20120200601 (Osterhout et al., Aug. 9, 2012, "AR Glasses with State Triggered Eye Control Interaction with Advertising Facility"); 20120201725 (Imran, Aug. 9, 2012, "Micro-Fluidic Device"); 20120203081 (Leboeuf et al., Aug. 9, 2012, "Physiological and Environmental Monitoring Apparatus and Systems"); 20120206322 (Osterhout et al., Aug. 16, 2012, "AR Glasses with Event and Sensor Input Triggered User Action Capture Device Control of AR Eyepiece Facility"); 20120206323 (Osterhout et al., Aug. 16, 2012, "AR Glasses with Event and Sensor Triggered AR Eyepiece Interface to External Devices"); and 20120206334 (Osterhout et al., Aug. 16, 2012, "AR Glasses with Event and User Action Capture Device Control of External Applications").

Further U.S. patent applications in this category include: 20120206335 (Osterhout et al., Aug. 16, 2012, "AR Glasses with Event, Sensor, and User Action Based Direct Control of External Devices with Feedback"); 20120206485 (Osterhout et al., Aug. 16, 2012, "AR Glasses with Event and Sensor Triggered User Movement Control of AR Eyepiece Facilities"); 20120212398 (Border et al., Aug. 23, 2012, "See-Through Near-Eye Display Glasses Including a Partially Reflective, Partially Transmitting Optical Element"); 20120212399 (Border et al., Aug. 23, 2012, "See-Through Near-Eye Display Glasses Wherein Image Light Is Transmitted to and Reflected from an Optically Flat Film"); 20120212400 (Border et al., Aug. 23, 2012, "See-Through Near-Eye Display Glasses Including a Curved Polarizing Film in the Image Source, a Partially Reflective, Partially Transmitting Optical Element and an Optically Flat Film"); 20120212406 (Osterhout et al., Aug. 23, 2012, "AR Glasses with Event and Sensor Triggered AR Eyepiece Command and Control Facility of the AR Eyepiece"); 20120212414 (Osterhout et al., Aug. 23, 2012, "AR Glasses with Event and Sensor Triggered Control of AR Eyepiece Applications"); 20120218172 (Border et al., Aug. 30, 2012, "See-Through Near-Eye Display Glasses with a Small Scale Image Source"); 20120218301 (Miller, Aug. 30, 2012, "See-Through Display with an Optical Assembly Including a Wedge-Shaped Illumination System"); 20120235883 (Border et al., Sep. 20, 2012, "See-Through Near-Eye Display Glasses with a Light Transmissive Wedge Shaped Illumination System"); 20120235885 (Miller et al., Sep. 20, 2012, "Grating in a Light Transmissive Illumination System for See-Through Near-Eye Display Glasses"); and 20120235886 (Border et al., Sep. 20, 2012, "See-Through Near-Eye Display Glasses with a Small Scale Image Source").

Further U.S. patent applications in this category include: 20120235887 (Border et al., Sep. 20, 2012, "See-Through Near-Eye Display Glasses Including a Partially Reflective, Partially Transmitting Optical Element and an Optically Flat Film"); 20120235900 (Border et al., Sep. 20, 2012, "See-Through Near-Eye Display Glasses with a Fast Response Photochromic Film System for Quick Transition from Dark to Clear"); 20120236030 (Border et al., Sep. 20, 2012, "See-Through Near-Eye Display Glasses Including a Modular Image Source"); 20120236031 (Haddick et al., Sep. 20, 2012, "System and Method for Delivering Content to a Group of See-Through Near Eye Display Eyepieces"); 20120242678 (Border et al., Sep. 27, 2012, "See-Through Near-Eye Display Glasses Including an Auto-Brightness Control for the Display Brightness Based on the Brightness in the Environment"); 20120242697 (Border et al., Sep. 27, 2012, "See-Through Near-Eye Display Glasses with the Optical Assembly Including Absorptive Polarizers or Anti-Reflective Coatings to Reduce Stray Light"); 20120242698 (Haddick et al., Sep. 27, 2012, "See-Through Near-Eye Display Glasses with a Multi-Segment Processor-Controlled Optical Layer"); 20120249797 (Haddick et al., Oct. 4, 2012, "Head-Worn Adaptive Display"); 20120302855 (Kamath et al., Nov. 29, 2012, "Systems and Methods for Processing Sensor Data"); 20130035563 (Angelides, Feb. 7, 2013, "Progressively Personalized Wireless-Based Interactive Diabetes Treatment"); 20130083003 (Perez et al., Apr. 4, 2013, "Personal Audio/Visual System"); 20130083064 (Geisner et al., Apr. 4, 2013, "Personal Audio/Visual Apparatus Providing Resource Management"); and 20130095459 (Tran, Apr. 18, 2013, "Health Monitoring System"). Prior art which appears to be most appropriately classified into this category also includes: U.S. patent application Ser. No. 13/523,739 (Connor, Jun. 14, 2012, "The Willpower Watch™: A Wearable Food Consumption Monitor"); U.S. patent application Ser. No. 13/616,238 (Connor, Sep. 14, 2012, "Interactive Voluntary and Involuntary Caloric Intake Monitor"); and WO 2003032629 (Grosvenor, Apr. 17, 2003, "Automatic Photography").

(4) Wearable Devices to Monitor Caloric Expenditure Activities and to Help Measure Food Consumption Wearable devices and methods in this category provide at least some measurement of both caloric expenditure activities and food consumption, but their measurement of food consumption is much less automated and accurate than that of caloric expenditure activities. In some respects, devices and methods in this category are like those in the first category, with the addition of caloric expenditure monitoring.

Most of the devices and methods in this category include a wearable accelerometer (and possibly also other wearable sensors) for measuring caloric expenditure, but rely on non-automated logging of food consumption information through a human-to-computer interface. Most of the devices and methods in this category display information concerning food consumption as part of the energy balance equation, but do not automatically collect this food consumption information.

Wearable devices and methods in this category are a useful step toward developing wearable energy balance devices that can help people to monitor and manage their energy balance and weight. However, prior art in this category has limitations with respect to the accuracy of food consumption measurement. These limitations are generally the same as the limitations of devices and methods in the first category (non-wearable devices to help measure food consumption). Their accuracy depends critically on the consistency with which a person enters information into the device and the accuracy with which the person assesses the amounts and ingredients of non-standard foods consumed. Both of these factors can be problematic.

Specific examples of potentially-relevant prior art which appear to be most appropriately classified into this category include the following U.S. Pat. No. 6,095,949 (Arai, Aug. 1, 2000, "Health Management Device"); U.S. Pat. No. 6,506,152 (Lackey et al., Jan. 14, 2003, "Caloric Energy Balance Monitor"); U.S. Pat. No. 6,571,200 (Mault, May 27, 2003, "Monitoring Caloric Expenditure Resulting from Body Activity"); U.S. Pat. No. 6,635,015 (Sagel, Oct. 21, 2003, "Body Weight Management System"); U.S. Pat. No. 6,675,041 (Dickinson, Jan. 6, 2004, "Electronic Apparatus and Method for Monitoring Net Calorie Intake"); U.S. Pat. No. 7,361,141 (Nissila et al., Apr. 22, 2008, "Method and Device for Weight Management of Humans"); U.S. Pat. No. 8,180,591 (Yuen et al., May 15, 2012, "Portable Monitoring Devices and Methods of Operating Same"); U.S. Pat. No. 8,180,592 (Yuen et al., May 15, 2012, "Portable Monitoring Devices and Methods of Operating Same"); U.S. Pat. No. 8,311,769 (Yuen et al., Nov. 13, 2012, "Portable Monitoring Devices and Methods of Operating Same"); U.S. Pat. No. 8,311,770 (Yuen et al., Nov. 13, 2012, "Portable Monitoring Devices and Methods of Operating Same"); U.S. Pat. No. 8,386,008 (Yuen et al., Feb. 26, 2013, "Activity Monitoring Systems and Methods of Operating Same"); U.S. Pat. No. 8,386,008 (Yuen et al., Feb. 26, 2013, "Portable Monitoring Devices and Methods of Operating Same"); and U.S. Pat. No. 8,437,980 (Yuen et al., May 7, 2013, "Portable Monitoring Devices and Methods of Operating Same").

Specific examples of potentially-relevant prior art which appear to be most appropriately classified into this category also include the following U.S. patent applications: 20020109600 (Mault et al., Aug. 15, 2002, "Body Supported Activity and Condition Monitor"); 20020156351 (Sagel, Oct. 24, 2002, "Body Weight Management System"); 20050004436 (Nissila et al., Jan. 6, 2005, "Method and Device for Weight Management of Humans"); 20100079291 (Kroll et al., Apr. 1, 2010, "Personalized Activity Monitor and Weight Management System"); 20100228160 (Schweizer, Sep. 9, 2010, "Apparatus for Activity Monitoring"); 20110087137 (Hanoun, Apr. 14, 2011, "Mobile Fitness and Personal Caloric Management System"); 20120083705 (Yuen et al., Apr. 5, 2012, "Activity Monitoring Systems and Methods of Operating Same"); 20120083714 (Yuen et al., Apr. 5, 2012, "Activity Monitoring Systems and Methods of Operating Same"); 20120083715 (Yuen et al., Apr. 5, 2012, "Portable Monitoring Devices and Methods of Operating Same"); 20120083716 (Yuen et al., Apr. 5, 2012, "Portable Monitoring Devices and Methods of Operating Same"); 20120084053 (Yuen et al., Apr. 5, 2012, "Portable Monitoring Devices and Methods of Operating Same"); 20120084054 (Yuen et al., Apr. 5, 2012, "Portable Monitoring Devices and Methods of Operating Same"); and 20120226471 (Yuen et al., Sep. 6, 2012, "Portable Monitoring Devices and Methods of Operating Same").

Additional U.S. patent applications which appear to be most appropriately classified into this category include: 20120226472 (Yuen et al., Sep. 6, 2012, "Portable Monitoring Devices and Methods of Operating Same"); 20120316458 (Rahman et al., Dec. 13, 2012, "Data-Capable Band for Medical Diagnosis, Monitoring, and Treatment"); 20120316896 (Rahman et al., Dec. 13, 2012, "Personal Advisor System Using Data-Capable Band"); 20120316932 (Rahman et al., Dec. 13, 2012, "Wellness Application for Data-Capable Band"); 20120316932 (Rahman et al., Dec. 13, 2012, "Wellness Application for Data-Capable Band"); 20120317167 (Rahman et al., Dec. 13, 2012, "Wellness Application for Data-Capable Band"); 20130006125 (Kroll et al., Jan. 3, 2013, "Personalized Activity Monitor and Weight Management System"); 20130029807 (Amsel, Jan. 31, 2013, "Health Tracking Program"); 20130073254 (Yuen et al., Mar. 21, 2013, "Portable Monitoring Devices and Methods of Operating Same"); 20130073255 (Yuen et al., Mar. 21, 2013, "Portable Monitoring Devices and Methods of Operating Same"); 20130080113 (Yuen et al., Mar. 28, 2013, "Portable Monitoring Devices and Methods of Operating Same"); and 20130096843 (Yuen et al., Apr. 18, 2013, "Portable Monitoring Devices and Methods of Operating Same").

(5) Wearable Devices to Monitor and Measure Both Caloric Expenditure Activities and Food Consumption Wearable devices and methods in this category provide monitoring and measurement of both caloric expenditure activities and food consumption. Their monitoring and measurement of food consumption is generally not as automated or accurate as the monitoring and measurement of caloric expenditure activities, but devices in this category are a significant step toward integrated wearable energy balance devices. In some respects, devices and methods in this category are like those in the third category, with the addition of caloric expenditure monitoring.

Although wearable device and methods in this category are a significant step toward developing integrated energy balance devices which can be useful for energy balance, weight management, and proper nutrition, prior art in this category has not yet solved the dilemma of personal privacy vs. accuracy of food consumption measurement. Some prior art in this category offers relatively-low privacy intrusion, but has relatively-low accuracy of food consumption measurement. Other prior art in this category offers relatively-high accuracy for food consumption measurement, but comes with relatively-high privacy intrusion. The invention that we will disclose later will solve this problem by offering relatively-high accuracy for food consumption measurement with relatively-low privacy intrusion.

Specific examples of potentially-relevant prior art which appear to be most appropriately classified into this category include the following U.S. Pat. No. 6,513,532 (Mault et al., Feb. 4, 2003, "Diet and Activity Monitoring Device"); U.S. Pat. No. 6,605,038 (Teller et al., Aug. 12, 2003, "System for Monitoring Health, Wellness and Fitness"); U.S. Pat. No. 6,790,178 (Mault et al., Sep. 14, 2004, "Physiological Monitor and Associated Computation, Display and Communication Unit"); U.S. Pat. No. 7,020,508 (Stivoric et al., Mar. 28, 2006, "Apparatus for Detecting Human Physiological and Contextual Information"); U.S. Pat. No. 7,261,690 (Teller et al., Aug. 28, 2007, "Apparatus for Monitoring Health, Wellness and Fitness"); U.S. Pat. No. 7,285,090 (Stivoric et al., Oct. 23, 2007, "Apparatus for Detecting, Receiving, Deriving and Displaying Human Physiological and Contextual Information"); U.S. Pat. No. 7,689,437 (Teller et al., Mar. 30, 2010, "System for Monitoring Health, Wellness and Fitness"); U.S. Pat. No. 7,914,468 (Shalon et al., Mar. 29, 2011, "Systems and Methods for Monitoring and Modifying Behavior"); U.S. Pat. No. 7,959,567 (Stivoric et al., Jun. 14, 2011, "Device to Enable Quick Entry of Caloric Content"); U.S. Pat. No. 8,073,707 (Teller et al., Dec. 6, 2011, "System for Detecting Monitoring and Reporting an Individual's Physiological or Contextual Status"); U.S. Pat. No. 8,157,731 (Teller et al., Apr. 17, 2012, "Method and Apparatus for Auto Journaling of Continuous or Discrete Body States Utilizing Physiological and/or Contextual Parameters"); U.S. Pat. No. 8,323,189 (Tran et al., Dec. 4, 2012, "Health monitoring appliance"); U.S. Pat. No. 8,328,718 (Tran, Dec. 11, 2012, "Health Monitoring Appliance"); U.S. Pat. No. 8,398,546 (Pacione et al., Mar. 19, 2013, "System for Monitoring and Managing Body Weight and Other Physiological Conditions Including Iterative and Personalized Planning, Intervention and Reporting Capability"); and U.S. Pat. No. 8,425,415 (Tran, Apr. 23, 2013, "Health Monitoring Appliance").

Specific examples of potentially-relevant prior art which appear to be most appropriately classified into this category also include the following U.S. patent applications: 20010049470 (Mault et al., Dec. 6, 2001, "Diet and Activity Monitoring Device"); 20020027164 (Mault et al., Mar. 7, 2002, "Portable Computing Apparatus Particularly Useful in a Weight Management Program"); 20020047867 (Mault et al., Apr. 25, 2002, "Image Based Diet Logging"); 20020133378 (Mault et al., Sep. 19, 2002, "System and Method of Integrated Calorie Management"); 20030065257 (Mault et al., Apr. 3, 2003, "Diet and Activity Monitoring Device"); 20030208110 (Mault et al., Nov. 6, 2003, "Physiological Monitoring using Wrist-Mounted Device"); 20040034289 (Teller et al., Feb. 19, 2004, "System for Monitoring Health, Wellness and Fitness"); 20040133081 (Teller et al., Jul. 8, 2004, "Method and Apparatus for Auto Journaling of Continuous or Discrete Body States Utilizing Physiological and/or Contextual Parameters"); 20040152957 (Stivoric et al., Aug. 5, 2004, "Apparatus for Detecting, Receiving, Deriving and Displaying Human Physiological and Contextual Information"); 20050113650 (Pacione et al., May 26, 2005, "System for Monitoring and Managing Body Weight and Other Physiological Conditions Including Iterative and Personalized Planning Intervention and Reporting Capability"); 20060031102 (Teller et al., Feb. 9, 2006, "System for Detecting Monitoring and Reporting an Individual's Physiological or Contextual Status"); 20060064037 (Shalon et al., Mar. 23, 2006, "Systems and Methods for Monitoring and Modifying Behavior"); 20060122474 (Teller et al., Jun. 8, 2006, "Apparatus for Monitoring Health Wellness and Fitness"); and 20060264730 (Stivoric et al., Nov. 23, 2006, "Apparatus for Detecting Human Physiological and Contextual Information").

Additional U.S. patent applications which appear to be most appropriately classified into this category include: 20070100666 (Stivoric et al., May 3, 2007, "Devices and Systems for Contextual and Physiological-Based Detection, Monitoring, Reporting, Entertainment, and Control of Other Devices"); 20080161654 (Teller et al., Jul. 3, 2008, "Method and Apparatus for Auto Journaling of Body States and Providing Derived Physiological States Utilizing Physiological and/or Contextual Parameter"); 20080161655 (Teller et al., Jul. 3, 2008, "Method and Apparatus for Auto Journaling of Body States and Providing Derived Physiological States Utilizing Physiological and/or Contextual Parameter"); 20080167535 (Andre et. al, Jul. 10, 2008, "Devices and Systems for Contextual and Physiological-Based Reporting, Entertainment, Control of Other Devices, Health Assessment and Therapy"); 20080167536 (Teller et al., Jul. 10, 2008, "Method and Apparatus for Auto Journaling of Body States and Providing Derived Physiological States Utilizing Physiological and/or Contextual Parameter"); 20080167537 (Teller et al., Jul. 10, 2008, "Method and Apparatus for Auto Journaling of Body States and Providing Derived Physiological States Utilizing Physiological and/or Contextual Parameter"); 20080167538 (Teller et al., Jul. 10, 2008, "Method and Apparatus for Auto Journaling of Body States and Providing Derived Physiological States Utilizing Physiological and/or Contextual Parameter"); 20080167539 (Teller et al., Jul. 10, 2008, "Method and Apparatus for Auto Journaling of Body States and Providing Derived Physiological States Utilizing Physiological and/or Contextual Parameter"); and 20080171920 (Teller et al., Jul. 17, 2008, "Method and Apparatus for Auto Journaling of Body States and Providing Derived Physiological States Utilizing Physiological and/or Contextual Parameter").

Further U.S. patent applications in this category include: 20080171921 (Teller et al., Jul. 17, 2008, "Method and Apparatus for Auto Journaling of Body States and Providing Derived Physiological States Utilizing Physiological and/or Contextual Parameter"); 20080171922 (Teller et al., Jul. 17, 2008, "Method and Apparatus for Auto Journaling of Body States and Providing Derived Physiological States Utilizing Physiological and/or Contextual Parameter"); 20080275309 (Stivoric et al., Nov. 6, 2008, "Input Output Device for Use with Body Monitor"); 20090012433 (Fernstrom et al., Jan. 8, 2009, "Method, Apparatus and System for Food Intake and Physical Activity Assessment"); 20090177068 (Stivoric et al., Jul. 9, 2009, "Method and Apparatus for Providing Derived Glucose Information Utilizing Physiological and/or Contextual Parameters"); 20110125063 (Shalon et al., May 26, 2011, "Systems and Methods for Monitoring and Modifying Behavior"); 20110276312 (Shalon et al., Nov. 10, 2011, "Device for Monitoring and Modifying Eating Behavior"); 20120313776 (Utter et al., Dec. 13, 2012, "General Health and Wellness Management Method and Apparatus for a Wellness Application Using Data from a Data-Capable Band"); 20120313776 (Utter, Dec. 13, 2012, "General Health and Wellness Management Method and Apparatus for a Wellness Application Using Data from a Data-Capable Band"); and 20120326873 (Utter, Dec. 27, 2012, "Activity Attainment Method and Apparatus for a Wellness Application Using Data from a Data-Capable Band").

Further U.S. patent applications in this category include: 20120326873 (Utter, Dec. 27, 2012, "Activity Attainment Method and Apparatus for a Wellness Application Using Data from a Data-Capable Band"); 20120330109 (Tran, Dec. 27, 2012, "Health Monitoring Appliance"); 20130002435 (Utter, Jan. 3, 2013, "Sleep Management Method and Apparatus for a Wellness Application Using Data from a Data-Capable Band"); 20130004923 (Utter, Jan. 3, 2013, "Nutrition Management Method and Apparatus for a Wellness Application Using Data from a Data-Capable Band"); 20130069780 (Tran et al., Mar. 21, 2013, "Health Monitoring Appliance"); and 20130072765 (Kahn et al., Mar. 21, 2013, "Body-Worn Monitor"). Prior art which appears to be most appropriately classified into this category also includes: WO 2005029242 (Pacione et al., Jun. 9, 2005, "System for Monitoring and Managing Body Weight and Other Physiological Conditions Including Iterative and Personalized Planning, Intervention and Reporting Capability"); WO 2010070645 (Einav, Jun. 24, 2010, "Method and System for Monitoring Eating Habits"); and WO 2012170584 (Utter, Dec. 13, 2012, "General Health and Wellness Management Method and Apparatus for a Wellness Application Using Data from a Data-Capable Band").

(6) Other Potentially-Relevant Devices and Methods

When reviewing the prior art, I found a number of examples of prior art that may be potentially relevant to this present invention but which do not fall neatly into one of the above five categories. I include them here in a miscellaneous category of other potentially-relevant devices and methods. The titles are given to help the reader get insights into their diverse, but potentially-relevant, contents. Specific examples of potentially-relevant prior art which appear to be most appropriately classified into this category include the following U.S. Pat. No. 3,885,576 (Symmes, May 27, 1975, "Wrist Band Including a Mercury Switch to Induce an Electric Shock"); U.S. Pat. No. 4,221,959 (Sessler, Sep. 9, 1980, "Checking Device for Checking the Food Intake"); U.S. Pat. No. 4,310,316 (Thomann, Jan. 12, 1982, "Diet Control Apparatus"); U.S. Pat. No. 4,355,645 (Mitani et al., Oct. 26, 1982, "Device for Displaying Masticatory Muscle Activities"); U.S. Pat. No. 4,819,860 (Hargrove et al., Apr. 11, 1989, "Wrist-Mounted Vital Functions Monitor and Emergency Locator"); U.S. Pat. No. 4,917,108 (Mault, Apr. 17, 1990, "Oxygen Consumption Meter"); U.S. Pat. No. 5,148,002 (Kuo et al., Sep. 15, 1992, "Multi-Functional Garment System"); U.S. Pat. No. 5,285,398 (Janik, Feb. 8, 1994, "Flexible Wearable Computer"); U.S. Pat. No. 5,301,679 (Taylor, Apr. 12, 1994, "Method and System for Analysis of Body Sounds"); U.S. Pat. No. 5,491,651 (Janik, Feb. 13, 1996, "Flexible Wearable Computer"); U.S. Pat. No. 5,515,858 (Myllymaki, May 14, 1996, "Wrist-Held Monitoring Device for Physical Condition"); U.S. Pat. No. 5,555,490 (Carroll, Sep. 10, 1996, "Wearable Personal Computer System"); U.S. Pat. No. 5,581,492 (Janik, Dec. 3, 1996, "Flexible Wearable Computer"); U.S. Pat. No. 5,636,146 (Flentov et al., Jun. 3, 1997, "Apparatus and Methods for Determining Loft Time and Speed"); U.S. Pat. No. 5,908,301 (Lutz, Jun. 1, 1999, "Method and Device for Modifying Behavior"); U.S. Pat. No. 6,095,985 (Raymond et al., Aug. 1, 2000, "Health Monitoring System"); U.S. Pat. No. 6,218,358 (Firestein et al., Apr. 17, 2001, "Functional Expression of, and Assay for, Functional Cellular Receptors In Vivo"); U.S. Pat. No. 6,266,623 (Vock et al., Jul. 24, 2001, "Sport Monitoring Apparatus for Determining Loft Time, Speed, Power Absorbed and Other Factors Such as Height"); U.S. Pat. No. 6,387,329 (Lewis et al., May 14, 2002, "Use of an Array of Polymeric Sensors of Varying Thickness for Detecting Analytes in Fluids"); U.S. Pat. No. 6,473,368 (Stanfield, Oct. 29, 2002, "Consumption Controller"); and U.S. Pat. No. 6,572,542 (Houben et al., Jun. 3, 2003, "System and Method for Monitoring and Controlling the Glycemic State of a Patient").

Additional U.S. patents which appear to be most appropriately classified into this category include: U.S. Pat. No. 6,595,929 (Stivoric et al., Jul. 22, 2003, "System for Monitoring Health Wellness and Fitness Having a Method and Apparatus for Improved Measurement of Heat Flow"); U.S. Pat. No. 6,610,367 (Lewis et al., Aug. 26, 2003, "Use of an Array of Polymeric Sensors of Varying Thickness for Detecting Analytes in Fluids"); U.S. Pat. No. 6,765,488 (Stanfield, Jul. 20, 2004, "Enhanced Consumption Controller"); U.S. Pat. No. 6,850,861 (Faiola et al., Feb. 1, 2005, "System for Monitoring Sensing Device Data Such as Food Sensing Device Data"); U.S. Pat. No. 7,122,152 (Lewis et al., Oct. 17, 2006, "Spatiotemporal and Geometric Optimization of Sensor Arrays for Detecting Analytes Fluids"); U.S. Pat. No. 7,192,136 (Howell et al., Mar. 20, 2007, "Tethered Electrical Components for Eyeglasses"); U.S. Pat. No. 7,241,880 (Adler et al., Jul. 10, 2007, "T1R Taste Receptors and Genes Encoding Same"); U.S. Pat. No. 7,247,023 (Peplinski et al., Jul. 24, 2007, "System and Method for Monitoring Weight and Nutrition"); U.S. Pat. No. 7,502,643 (Farringdon et al., Mar. 10, 2009, "Method and Apparatus for Measuring Heart Related Parameters"); U.S. Pat. No. 7,595,023 (Lewis et al., Sep. 29, 2009, "Spatiotemporal and Geometric Optimization of Sensor Arrays for Detecting Analytes in Fluids"); U.S. Pat. No. 7,651,868 (Mcdevitt et al., Jan. 26, 2010, "Method and System for the Analysis of Saliva using a Sensor Array"); U.S. Pat. No. 7,882,150 (Badyal, Feb. 1, 2011, "Health Advisor"); U.S. Pat. No. 7,905,815 (Ellis et al., Mar. 15, 2011, "Personal Data Collection Systems and Methods"); U.S. Pat. No. 7,905,832 (Lau et al., Mar. 15, 2011, "Method and System for Personalized Medical Monitoring and Notifications Therefor"); and U.S. Pat. No. 7,931,562 (Ellis et al., Apr. 26, 2011, "Mobile Data Logging Systems and Methods").

Further U.S. patents in this category include: U.S. Pat. No. 8,067,185 (Zoller et al., Nov. 29, 2011, "Methods of Quantifying Taste of Compounds for Food or Beverages"); U.S. Pat. No. 8,116,841 (Bly et al., Feb. 14, 2012, "Adherent Device with Multiple Physiological Sensors"); U.S. Pat. No. 8,121,673 (Tran, Feb. 12, 1012, "Health Monitoring Appliance"); U.S. Pat. No. 8,170,656 (Tan et al., May 1, 2012, "Wearable Electromyography-Based Controllers for Human-Computer Interface"); U.S. Pat. No. 8,275,635 (Stivoric et al., Sep. 25, 2012, "Integration of Lifeotypes with Devices and Systems"); U.S. Pat. No. 8,285,356 (Bly et al., Oct. 9, 2012, "Adherent Device with Multiple Physiological Sensors"); U.S. Pat. No. 8,314,224 (Adler et al., Nov. 20, 2012, "T1R Taste Receptors and Genes Encoding Same"); U.S. Pat. No. 8,323,188 (Tran, Dec. 4, 2012, "Health Monitoring Appliance"); U.S. Pat. No. 8,323,218 (Davis et al., Dec. 4, 2012, "Generation of Proportional Posture Information Over Multiple Time Intervals"); U.S. Pat. No. 8,334,367 (Adler, Dec. 18, 2012, "T2R Taste Receptors and Genes Encoding Same"); U.S. Pat. No. 8,340,754 (Chamney et al., Dec. 25, 2012, "Method and a Device for Determining the Hydration and/or Nutrition Status of a Patient"); U.S. Pat. No. 8,344,325 (Merrell et al., Jan. 1, 2013, "Electronic Device With Sensing Assembly and Method for Detecting Basic Gestures"); U.S. Pat. No. 8,344,998 (Fitzgerald et al., Jan. 1, 2013, "Gesture-Based Power Management of a Wearable Portable Electronic Device with Display"); U.S. Pat. No. 8,345,414 (Mooring et al., Jan. 1, 2013, "Wearable Computing Module"); U.S. Pat. No. 8,364,250 (Moon et al., Jan. 29, 2013, "Body-Worn Vital Sign Monitor"); and U.S. Pat. No. 8,369,936 (Farringdon et al., Feb. 5, 2013, "Wearable Apparatus for Measuring Heart-Related Parameters and Deriving Human Status Parameters from Sensed Physiological and Contextual Parameters").

Further U.S. patents in this category include: U.S. Pat. No. 8,370,176 (Vespasiani, Feb. 5, 2013, "Method and System for Defining and Interactively Managing a Watched Diet"); U.S. Pat. No. 8,379,488 (Gossweiler et al., Feb. 19, 2013, "Smart-Watch Including Flip Up Display"); U.S. Pat. No. 8,382,482 (Miller-Kovach et al., Feb. 26, 2013, "Processes and Systems for Achieving and Assisting in Improved Nutrition Based on Food Energy Data and Relative Healthfulness Data"); U.S. Pat. No. 8,382,681 (Escutia et al., Feb. 26, 2013, "Fully Integrated Wearable or Handheld Monitor"); U.S. Pat. No. 8,409,118 (Agrawal et al., Apr. 2, 2013, "Upper Arm Wearable Exoskeleton"); U.S. Pat. No. 8,417,298 (Mittleman et al., Apr. 9, 2013, "Mounting Structures for Portable Electronic Devices"); U.S. Pat. No. 8,419,268 (Yu Apr. 16, 2013, "Wearable Electronic Device"); U.S. Pat. No. 8,421,634 (Tan et al., Apr. 16, 2013, "Sensing Mechanical Energy to Appropriate the Body for Data Input"); U.S. Pat. No. 8,423,378 (Goldberg, Apr. 16, 2013, "Facilitating Health Care Management of Subjects"); U.S. Pat. No. 8,423,380 (Gelly Apr. 16, 2013, "Method and System for Interactive Health Regimen Accountability and Patient Monitoring"); and U.S. Pat. No. 8,437,823 (Ozawa et al., May 7, 2013, "Noninvasive Living Body Measurement Apparatus and Noninvasive Living Body Measurement Method").

Specific examples of potentially-relevant prior art which appear to be most appropriately classified into this category also include the following U.S. patent applications: 20020049482 (Fabian et al., Apr. 25, 2002, "Lifestyle Management System"); 20040100376 (Lye et al., May 27, 2004, "Healthcare Monitoring System"); 20050113649 (Bergantino, May 26, 2005, "Method and Apparatus for Managing a User's Health"); 20050146419 (Porter, Jul. 7, 2005, "Programmable Restricted Access Food Storage Container and Behavior Modification Assistant"); 20050263160 (Utley et al., Dec. 1, 2005, "Intraoral Aversion Devices and Methods"); 20060015016 (Thornton, Jan. 19, 2006, "Caloric Balance Weight Control System and Methods of Making and Using Same"); 20060122468 (Tavor, Jun. 8, 2006, "Nutritional Counseling Method and Server"); 20070106129 (Srivathsa et al., May 10, 2007, "Dietary Monitoring System for Comprehensive Patient Management"); 20080036737 (Hernandez-Rebollar, Feb. 14, 2008, "Arm Skeleton for Capturing Arm Position and Movement"); 20080140444 (Karkanias et al., Jun. 12, 2008, "Patient Monitoring Via Image Capture"); 20090261987 (Sun, Oct. 22, 2009, "Sensor Instrument System Including Method for Detecting Analytes in Fluids"); 20100000292 (Karabacak et al., Jan. 7, 2010, "Sensing Device"); 20100049004 (Edman et al., Feb. 25, 2010, "Metabolic Energy Monitoring System"); 20100049010 (Goldreich, Feb. 25, 2010, "Method and Device for Measuring Physiological Parameters at the Wrist"); 20100055271 (Miller-Kovach et al., Mar. 4, 2010, "Processes and Systems Based on Metabolic Conversion Efficiency"); 20100055652 (Miller-Kovach et al., Mar. 4, 2010, "Processes and Systems Based on Dietary Fiber as Energy"); and 20100055653 (Miller-Kovach et al., Mar. 4, 2010, "Processes and Systems Using and Producing Food Healthfulness Data Based on Food Metagroups").

Additional U.S. patent applications which appear to be most appropriately classified into this category include: 20100209897 (Utley et al., Aug. 19, 2010, "Intraoral Behavior Monitoring and Aversion Devices and Methods"); 20100291515 (Pinnisi et al., Nov. 18, 2010, "Regulating Food and Beverage Intake"); 20110053128 (Alman, Mar. 3, 2011, "Automated Patient Monitoring and Counseling System"); 20110077471 (King, Mar. 31, 2011, "Treatment and Prevention of Overweight and Obesity by Altering Visual Perception of Food During Consumption"); 20110205851 (Harris, Aug. 25, 2011, "E-Watch"); 20110218407 (Haberman et al., Sep. 8, 2011, "Method and Apparatus to Monitor, Analyze and Optimize Physiological State of Nutrition"); 20120015432 (Adler, Jan. 19, 2012, "Isolated Bitter Taste Receptor Polypeptides"); 20120021388 (Arbuckle et al., Jan. 26, 2012, "System and Method for Weight Management"); 20120053426 (Webster et al., Mar. 1, 2012, "System and Method for Measuring Calorie Content of a Food Sample"); 20120071731 (Gottesman, Mar. 22, 2012, "System and Method for Physiological Monitoring"); 20120179020 (Wekell, Jul. 12, 2012, "Patient Monitoring Device"); 20120188158 (Tan et al., Jul. 26, 2012, "Wearable Electromyography-Based Human-Computer Interface"); 20120214594 (Kirovski et al., Aug. 23, 2012, "Motion Recognition"); 20120231960 (Osterfeld et al., Sep. 13, 2012, "Systems and Methods for High-Throughput Detection of an Analyte in a Sample"); 20120235647 (Chung et al., Sep. 20, 2012, "Sensor with Energy-Harvesting Device"); 20120239304 (Hayter et al., Sep. 20, 2012, "Method and System for Determining Analyte Levels"); 20120242626 (Hu, Sep. 27, 2012, "Electronic Watch Capable of Adjusting Display Angle of Screen Content Thereof"); and 20120245472 (Rulkov et al., Sep. 27, 2012, "Monitoring Device with an Accelerometer, Method and System").

Further U.S. patent applications in this category include: 20120245714 (Mueller et al., Sep. 27, 2012, "System and Method for Counting Swimming Laps"); 20120254749 (Downs et al., Oct. 4, 2012, "System and Method for Controlling Life Goals"); 20120258804 (Ahmed, Oct. 11, 2012, "Motion-Based Input for Platforms and Applications"); 20120277638 (Skelton et al., Nov. 1, 2012, "Obtaining Baseline Patient Information"); 20120303638 (Bousamra et al., Nov. 29, 2012, "Location Enabled Food Database"); 20120315986 (Walling, Dec. 13, 2012, "Virtual Performance System"); 20120316793 (Jung et al., Dec. 13, 2012, "Methods and Systems for Indicating Behavior in a Population Cohort"); 20120326863 (Johnson et al., Dec. 27, 2012, "Wearable Portable Device and Method"); 20120330112 (Lamego et al., Dec. 27, 2012, "Patient Monitoring System"); 20120331201 (Rondel, Dec. 27, 2012, "Strap-Based Computing Device"); 20130002538 (Mooring et al., Jan. 3, 2013, "Gesture-Based User Interface for a Wearable Portable Device"); 20130002545 (Heinrich et al., Jan. 3, 2013, "Wearable Computer with Curved Display and Navigation Tool"); 20130002724 (Heinrich et al., Jan. 3, 2013, "Wearable Computer with Curved Display and Navigation Tool"); 20130009783 (Tran, Jan. 10, 2013, "Personal Emergency Response (PER) System"); 20130017789 (Chi et al., Jan. 17, 2013, "Systems and Methods for Accessing an Interaction State Between Multiple Devices"); 20130021226 (Bell, Jan. 24, 2013, "Wearable Display Devices"); 20130021658 (Miao et al., Jan. 24, 2013, "Compact See-Through Display System"); 20130027060 (Tralshawala et al., Jan. 31, 2013, "Systems and Methods for Non-Destructively Measuring Calorie Contents of Food Items"); and 20130035575 (Mayou et al., Feb. 7, 2013, "Systems and Methods for Detecting Glucose Level Data Patterns").

Further U.S. patent applications in this category include: 20130035865 (Mayou et al., Feb. 7, 2013, "Systems and Methods for Detecting Glucose Level Data Patterns"); 20130038056 (Donelan et al., Feb. 14, 2013, "Methods and Apparatus for Harvesting Biomechanical Energy"); 20130041272 (Guillen et al., Feb. 14, 2013, "Sensor Apparatus Adapted to be Incorporated in a Garment"); 20130044042 (Olsson et al., Feb. 21, 2013, "Wearable Device with Input and Output Structures"); 20130045037 (Schaffer, Feb. 21, 2013, "Wristwatch Keyboard"); 20130048737 (Baym et al., Feb. 28, 2013, "Systems, Devices, Admixtures, and Methods Including Transponders for Indication of Food Attributes"); 20130048738 (Baym et al., Feb. 28, 2013, "Systems, Devices, Admixtures, and Methods Including Transponders for Indication of Food Attributes"); 20130049931 (Baym et al., Feb. 28, 2013, "Systems, Devices, Methods, and Admixtures of Transponders and Food Products for Indication of Food Attributes"); 20130049932 (Baym et al., Feb. 28, 2013, "Systems, Devices, Methods, and Admixtures of Transponders and Food Products for Indication of Food Attributes"); 20130049933 (Baym et al., Feb. 28, 2013, "Systems, Devices, Methods, and Admixtures Including Interrogators and Interrogation of Tags for Indication of Food Attributes"); 20130049934 (Baym et al., Feb. 28, 2013, "Systems, Devices, Methods, and Admixtures Including Interrogators and Interrogation of Tags for Indication of Food Attributes"); and 20130053655 (Castellanos, Feb. 28, 2013, "Mobile Vascular Health Evaluation Devices").

Further U.S. patent applications in this category include: 20130053661 (Alberth et al., Feb. 28, 2013, "System for Enabling Reliable Skin Contract of an Electrical Wearable Device"); 20130063342 (Chen et al., Mar. 14, 2013, "Human Interface Input Acceleration System"); 20130065680 (Zavadsky et al., Mar. 14, 2013, "Method and Apparatus for Facilitating Strength Training"); 20130069931 (Wilson et al., Mar. 21, 2013, "Correlating Movement Information Received from Different Sources"); 20130069985 (Wong et al., Mar. 21, 2013, "Wearable Computer with Superimposed Controls and Instructions for External Device"); 20130070338 (Gupta et al., Mar. 21, 2013, "Lightweight Eyepiece for Head Mounted Display"); 20130072807 (Tran, Mar. 21, 2013, "Health Monitoring Appliance"); 20130083496 (Franklin et al., Apr. 4, 2013, "Flexible Electronic Devices"); 20130100027 (Wang et al., Apr. 25, 2013, "Portable Electronic Device"); 20130107674 (Gossweiler et al., May 2, 2013, "Smart-Watch with User Interface Features"); 20130109947 (Wood, May 2, 2013, "Methods and Systems for Continuous Non-Invasive Blood Pressure Measurement Using Photoacoustics"); 20130110549 (Lawn et al., May 2, 2013, "Device and Method for Assessing Blood Glucose Control"); 20130111611 (Barros Almedo et al., May 2, 2013, "Method to Measure the Metabolic Rate or Rate of Glucose Consumption of Cells or Tissues with High Spatiotemporal Resolution Using a Glucose Nanosensor"); 20130115717 (Guo et al., May 9, 2013, "Analyzing Chemical and Biological Substances Using Nano-Structure Based Spectral Sensing"); 20130116525 (Heller et al., May 9, 2013, "Analyte Monitoring Device and Methods of Use"); 20130117040 (James et al., May 9, 2013, "Method and System for Supporting a Health Regimen"); 20130117041 (Boyce et al., May 9, 2013, "Computer Method and System for Promoting Health, Wellness, and Fitness with Multiple Sponsors"); 20130117135 (Riddiford et al., May 9, 2013, "Multi-User Food and Drink Ordering System"); and 20130119255 (Dickinson et al., May 16, 2013, "Methods and Devices for Clothing Detection about a Wearable Electronic Device").

SUMMARY AND ADVANTAGES OF THIS INVENTION

This invention is a device, system, and method for monitoring food consumption comprising: (a) a wearable sensor that is configured to be worn on a person's body or clothing, wherein this wearable sensor automatically collects data that is used to detect probable eating events without requiring action by the person in association with a probable eating event apart from the act of eating, and wherein a probable eating event is a period of time during which the person is probably eating; (b) a voluntary human-to-computer interface, wherein this interface receives data from the person concerning the food that the person eats, wherein receipt of this data requires voluntary action by the person apart from the act of eating, and wherein the person is prompted to enter data using this interface when data collected by the wearable sensor indicates a probable eating event; and (c) a data analysis component, wherein this component analyzes data received from the human-to-computer interface to estimate the types and amounts of foods, ingredients, nutrients, and/or calories that are consumed by the person.

In an example, the wearable sensor of this invention can be part of a smart watch or smart bracelet that is worn on a person's wrist and monitors the person's wrist or hand motions to detect probable eating events. In an example, the voluntary human-to-computer interface of this invention can be part of a smart phone that the person is prompted to use to enter food consumption data during a selected period of time associated with an eating event.

In the design of devices and systems for monitoring a person's food consumption, there can be a tradeoff between greater accuracy of food consumption measurement versus preservation of a person's privacy. On the one hand, it is possible to create a wearable device with high compliance and accuracy for monitoring a person's food consumption, but such a device can be highly intrusive with respect the person's privacy. For example, one can create a wearable video camera that a person wears all the time. This wearable camera can continually record video pictures of what the person does and/or sees in order to detect and measure food consumption. However, such a continuously-recording wearable camera can be highly intrusive with respect to the person's privacy.

On the other hand, it is possible to create a system for measuring food consumption that relies only on a person's voluntary use of a hand-held device to enter food consumption data. This approach can be good for preserving a person's privacy, but can have low compliance for measuring total food consumption. People can easily forget, or otherwise fail, to consistently enter food consumption data for every meal and snack that they consume. Accordingly, there can be large gaps in the measurement of food consumption with this approach.

The invention disclosed herein addresses this tradeoff of accuracy versus privacy by integrating the operation of a wearable sensor (such as a smart watch that automatically detects food events) and a voluntary human-to-computer interface (such as a smart phone that the person is prompted to use to enter food consumption data) to achieve relatively-high measurement accuracy with relatively-low privacy intrusion. The strength of the prompt to enter food consumption data during eating events can be adjusted depending on how strongly the person feels about the need for self-control and accurate measurement of food consumption. This invention is a significant improvement over prior art that is based on a smart watch alone or a smart phone alone.

Information from this invention can be combined with a computer-to-human interface that provides feedback to encourage the person to eat healthy foods and to limit excess consumption of unhealthy foods. In order to be really useful for achieving good nutrition and health goals, a device, system, and method for measuring food consumption should differentiate between a person's consumption of healthy foods versus unhealthy foods. A device, system, or method can monitor a person's eating habits to encourage consumption of healthy foods and to discourage excess consumption of unhealthy foods. In an example, one or more of the following types of foods, ingredients, and/or nutrients can be classified as healthy or unhealthy and tracked by this device, system, and method.

In an example, at least one selected type of food, ingredient, or nutrient can be selected from the group consisting of: a specific type of carbohydrate, a class of carbohydrates, or all carbohydrates; a specific type of sugar, a class of sugars, or all sugars; a specific type of fat, a class of fats, or all fats; a specific type of cholesterol, a class of cholesterols, or all cholesterols; a specific type of protein, a class of proteins, or all proteins; a specific type of fiber, a class of fiber, or all fiber; a specific sodium compound, a class of sodium compounds, and all sodium compounds; high-carbohydrate food, high-sugar food, high-fat food, fried food, high-cholesterol food, high-protein food, high-fiber food, and high-sodium food.

A device, system, and method for monitoring a person's food consumption is not a panacea for good nutrition, energy balance, and weight management. However, such a device, system, and method can be a useful part of an overall strategy for encouraging good nutrition, energy balance, weight management, and health improvement when a person is engaged and motivated to make good use of it.

INTRODUCTION TO THE FIGURES

FIGS. 1 through 22 show examples of how this invention can be embodied, but they do not limit the full generalizability of the claims.

FIGS. 1 through 4 show an example of a device to monitor a person's food consumption comprising a smart watch (with a motion sensor) to detect eating events and a smart spoon (with a built-in chemical composition sensor), wherein the person is prompted to use the smart spoon to eat food when the smart watch detects an eating event.

FIGS. 5 through 8 show an example of a device to monitor a person's food consumption comprising a smart watch (with a motion sensor) to detect eating events and a smart spoon (with a built-in camera), wherein the person is prompted to use the smart spoon to take pictures of food when the smart watch detects an eating event.

FIGS. 9 through 12 show an example of a device to monitor a person's food consumption comprising a smart watch (with a motion sensor) to detect eating events and a smart phone (with a built-in camera), wherein the person is prompted to use the smart phone to take pictures of food when the smart watch detects an eating event.

FIGS. 13 through 15 show an example of a device to monitor a person's food consumption comprising a smart necklace (with a microphone) to detect eating events and a smart phone (with a built-in camera), wherein the person is prompted to use the smart phone to take pictures of food when the smart necklace detects an eating event.

FIGS. 16 through 18 show an example of a device to monitor a person's food consumption comprising a smart necklace (with a microphone) to detect eating events and a smart spoon (with a built-in chemical composition sensor), wherein the person is prompted to use the smart spoon to eat food when the smart necklace detects an eating event.

FIGS. 19 through 22 show an example of a device to monitor a person's food consumption comprising a smart watch (with a motion sensor) to detect eating events and a smart phone (with a touch screen interface), wherein the person is prompted to use the smart phone to enter food consumption data when the smart watch detects an eating event.

DETAILED DESCRIPTION OF THE FIGURES

Figure 5:
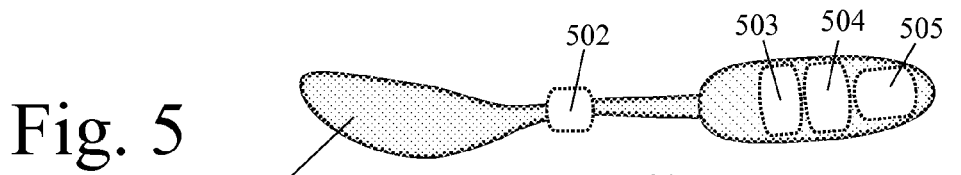

1. Overall Strategy for Good Nutrition and Energy Balance

A device, system, or method for measuring a person's consumption of at least one selected type of food, ingredient, and/or nutrient is not a panacea for good nutrition, energy balance, and weight management, but it can be a useful part of an overall strategy for encouraging good nutrition, energy balance, weight management, and health improvement. Although such a device, system, or method is not sufficient to ensure energy balance and good health, it can be very useful in combination with proper exercise and other good health behaviors. Such a device, system, or method can help a person to track and modify their eating habits as part of an overall system for good nutrition, energy balance, weight management, and health improvement.

In an example, at least one component of such a device can be worn on a person's body or clothing. A wearable food-consumption monitoring device or system can operate in a more-consistent manner than an entirely hand-held food-consumption monitoring device, while avoiding the potential invasiveness and expense of a food-consumption monitoring device that is implanted within the body.

Information from a food-consumption monitoring device that measures a person's consumption of at least one selected type of food, ingredient, and/or nutrient can be combined with information from a separate caloric expenditure monitoring device that measures a person's caloric expenditure to comprise an overall system for energy balance, fitness, weight management, and health improvement. In an example, a food-consumption monitoring device can be in wireless communication with a separate fitness monitoring device. In an example, capability for monitoring food consumption can be combined with capability for monitoring caloric expenditure within a single device. In an example, a single device can be used to measure the types and amounts of food, ingredients, and/or nutrients that a person consumes as well as the types and durations of the calorie-expending activities in which the person engages.

Information from a food-consumption monitoring device that measures a person's consumption of at least one selected type of food, ingredient, and/or nutrient can also be combined with a computer-to-human interface that provides feedback to encourage the person to eat healthy foods and to limit excess consumption of unhealthy foods. In an example, a food-consumption monitoring device can be in wireless communication with a separate feedback device that modifies the person's eating behavior. In an example, capability for monitoring food consumption can be combined with capability for providing behavior-modifying feedback within a single device. In an example, a single device can be used to measure the selected types and amounts of foods, ingredients, and/or nutrients that a person consumes and to provide visual, auditory, tactile, or other feedback to encourage the person to eat in a healthier manner.

A combined device and system for measuring and modifying caloric intake and caloric expenditure can be a useful part of an overall approach for good nutrition, energy balance, fitness, weight management, and good health. As part of such an overall system, a device that measures a person's consumption of at least one selected type of food, ingredient, and/or nutrient can play a key role in helping that person to achieve their goals with respect to proper nutrition, food consumption modification, energy balance, weight management, and good health outcomes.

2. Selected Types of Foods, Ingredients, and Nutrients

In order to be really useful for achieving good nutrition and health goals, a device and method for measuring a person's consumption of at least one selected type of food, ingredient, and/or nutrient should be able to differentiate between a person's consumption of healthy foods vs unhealthy foods. This requires the ability to identify consumption of selected types of foods, ingredients, and/or nutrients, as well as estimating the amounts of such consumption. It also requires selection of certain types and/or amounts of food, ingredients, and/or nutrients as healthy vs. unhealthy.

Generally, the technical challenges of identifying consumption of selected types of foods, ingredients, and/or nutrients are greater than the challenges of identifying which types are healthy or unhealthy. Accordingly, while this disclosure covers both food identification and classification, it focuses in greatest depth on identification of consumption of selected types of foods, ingredients, and nutrients. In this disclosure, food consumption is broadly defined to include consumption of liquid beverages and gelatinous food as well as solid food.

In an example, a device can identify consumption of at least one selected type of food. In such an example, selected types of ingredients or nutrients can be estimated indirectly using a database that links common types and amounts of food with common types and amounts of ingredients or nutrients. In another example, a device can directly identify consumption of at least one selected type of ingredient or nutrient. The latter does not rely on estimates from a database, but does require more complex ingredient-specific or nutrient-specific sensors. Since the concepts of food identification, ingredient identification, and nutrient identification are closely related, we consider them together for many portions of this disclosure, although we consider them separately in some sections for greater methodological detail. Various embodiments of the device and method disclosed herein can identify specific nutrients indirectly (through food identification and use of a database) or directly (through the use of nutrient-specific sensors).

Many people consume highly-processed foods whose primary ingredients include multiple types of sugar. The total amount of sugar is often obscured or hidden, even from those who read ingredients on labels. Sometimes sugar is disguised as "evaporated cane syrup." Sometimes different types of sugar are labeled as different ingredients (such as "plain sugar," "brown sugar," "maltose", "dextrose," and "evaporated cane syrup") in a single food item. In such cases, "sugar" does not appear as the main ingredient. However, when one adds up all the different types of sugar in different priority places on the ingredient list, then sugar really is the main ingredient. These highly-processed conglomerations of sugar (often including corn syrup, fats, and/or caffeine) often have colorful labels with cheery terms like "100% natural" or "high-energy." However, they are unhealthy when eaten in the quantities to which many Americans have become accustomed. It is no wonder that there is an obesity epidemic. The device and method disclosed herein is not be fooled by deceptive labeling of ingredients.

In various examples, a device for measuring a person's consumption of one or more selected types of foods, ingredients, and/or nutrients can measure one or more types selected from the group consisting of: a selected type of carbohydrate, a class of carbohydrates, or all carbohydrates; a selected type of sugar, a class of sugars, or all sugars; a selected type of fat, a class of fats, or all fats; a selected type of cholesterol, a class of cholesterols, or all cholesterols; a selected type of protein, a class of proteins, or all proteins; a selected type of fiber, a class of fiber, or all fibers; a specific sodium compound, a class of sodium compounds, or all sodium compounds; high-carbohydrate food, high-sugar food, high-fat food, fried food, high-cholesterol food, high-protein food, high-fiber food, and/or high-sodium food.

In various examples, a device for measuring a person's consumption of one or more selected types of foods, ingredients, and/or nutrients can measure one or more types selected from the group consisting of: simple carbohydrates, simple sugars, saturated fat, trans fat, Low Density Lipoprotein (LDL), and salt. In an example, a device for measuring consumption of a selected nutrient can measure a person's consumption of simple carbohydrates. In an example, a device for measuring consumption of a selected nutrient can measure a person's consumption of simple sugars. In an example, a device for measuring consumption of a selected nutrient can measure a person's consumption of saturated fats. In an example, a device for measuring consumption of a selected nutrient can measure a person's consumption of trans fats. In an example, a device for measuring consumption of a selected nutrient can measure a person's consumption of Low Density Lipoprotein (LDL). In an example, a device for measuring consumption of a selected nutrient can measure a person's consumption of sodium.

In various examples, a food-identifying sensor can detect one or more nutrients selected from the group consisting of: amino acid or protein (a selected type or general class), carbohydrate (a selected type or general class, such as single carbohydrates or complex carbohydrates), cholesterol (a selected type or class, such as HDL or LDL), dairy products (a selected type or general class), fat (a selected type or general class, such as unsaturated fat, saturated fat, or trans fat), fiber (a selected type or class, such as insoluble fiber or soluble fiber), mineral (a selected type), vitamin (a selected type), nuts (a selected type or general class, such as peanuts), sodium compounds (a selected type or general class), sugar (a selected type or general class, such as glucose), and water. In an example, food can be classified into general categories such as fruits, vegetables, or meat.

In an example, a device for measuring a person's consumption of a selected nutrient can measure a person's consumption of food that is high in simple carbohydrates. In an example, a device for measuring consumption of a selected nutrient can measure a person's consumption of food that is high in simple sugars. In an example, a device for measuring consumption of a selected nutrient can measure a person's consumption of food that is high in saturated fats. In an example, a device for measuring consumption of a selected nutrient can measure a person's consumption of food that is high in trans fats. In an example, a device for measuring consumption of a selected nutrient can measure a person's consumption of food that is high in Low Density Lipoprotein (LDL). In an example, a device for measuring consumption of a selected nutrient can measure a person's consumption of food that is high in sodium.

In an example, a device for measuring a person's consumption of a selected nutrient can measure a person's consumption of food wherein a high proportion of its calories comes from simple carbohydrates. In an example, a device for measuring consumption of a selected nutrient can measure a person's consumption of food wherein a high proportion of its calories comes from simple sugars. In an example, a device for measuring consumption of a selected nutrient can measure a person's consumption of food wherein a high proportion of its calories comes from saturated fats. In an example, a device for measuring consumption of a selected nutrient can measure a person's consumption of food wherein a high proportion of its calories comes from trans fats. In an example, a device for measuring consumption of a selected nutrient can measure a person's consumption of food wherein a high proportion of its calories comes from Low Density Lipoprotein (LDL). In an example, a device for measuring consumption of a selected nutrient can measure a person's consumption of food wherein a high proportion of its weight or volume is comprised of sodium compounds.

In an example, a device for measuring nutrient consumption can track the quantities of selected chemicals that a person consumes via food consumption. In various examples, these consumed chemicals can be selected from the group consisting of carbon, hydrogen, nitrogen, oxygen, phosphorus, and sulfur. In an example, a food-identifying device can selectively detect consumption of one or more types of unhealthy food, wherein unhealthy food is selected from the group consisting of: food that is high in simple carbohydrates; food that is high in simple sugars; food that is high in saturated or trans fat; fried food; food that is high in Low Density Lipoprotein (LDL); and food that is high in sodium.

In a broad range of examples, a food-identifying sensor can measure one or more types selected from the group consisting of: a selected food, ingredient, or nutrient that has been designated as unhealthy by a health care professional organization or by a specific health care provider for a specific person; a selected substance that has been identified as an allergen for a specific person; peanuts, shellfish, or dairy products; a selected substance that has been identified as being addictive for a specific person; alcohol; a vitamin or mineral; vitamin A, vitamin B1, thiamin, vitamin B12, cyanocobalamin, vitamin B2, riboflavin, vitamin C, ascorbic acid, vitamin D, vitamin E, calcium, copper, iodine, iron, magnesium, manganese, niacin, pantothenic acid, phosphorus, potassium, riboflavin, thiamin, and zinc; a selected type of carbohydrate, class of carbohydrates, or all carbohydrates; a selected type of sugar, class of sugars, or all sugars; simple carbohydrates, complex carbohydrates; simple sugars, complex sugars, monosaccharides, glucose, fructose, oligosaccharides, polysaccharides, starch, glycogen, disaccharides, sucrose, lactose, starch, sugar, dextrose, disaccharide, fructose, galactose, glucose, lactose, maltose, monosaccharide, processed sugars, raw sugars, and sucrose; a selected type of fat, class of fats, or all fats; fatty acids, monounsaturated fat, polyunsaturated fat, saturated fat, trans fat, and unsaturated fat; a selected type of cholesterol, a class of cholesterols, or all cholesterols; Low Density Lipoprotein (LDL), High Density Lipoprotein (HDL), Very Low Density Lipoprotein (VLDL), and triglycerides; a selected type of protein, a class of proteins, or all proteins; dairy protein, egg protein, fish protein, fruit protein, grain protein, legume protein, lipoprotein, meat protein, nut protein, poultry protein, tofu protein, vegetable protein, complete protein, incomplete protein, or other amino acids; a selected type of fiber, a class of fiber, or all fiber; dietary fiber, insoluble fiber, soluble fiber, and cellulose; a specific sodium compound, a class of sodium compounds, and all sodium compounds; salt; a selected type of meat, a class of meats, and all meats; a selected type of vegetable, a class of vegetables, and all vegetables; a selected type of fruit, a class of fruits, and all fruits; a selected type of grain, a class of grains, and all grains; high-carbohydrate food, high-sugar food, high-fat food, fried food, high-cholesterol food, high-protein food, high-fiber food, and high-sodium food.

In an example, a device for measuring a person's consumption of at least one specific food, ingredient, and/or nutrient that can analyze food composition can also identify one or more potential food allergens, toxins, or other substances selected from the group consisting of: ground nuts, tree nuts, dairy products, shell fish, eggs, gluten, pesticides, animal hormones, and antibiotics. In an example, a device can analyze food composition to identify one or more types of food whose consumption is prohibited or discouraged for religious, moral, and/or cultural reasons, such as pork or meat products of any kind.

3. Metrics for Measuring Foods, Ingredients, and Nutrients

Having discussed different ways to classify types of foods, ingredients, and nutrients, we now turn to different metrics for measuring the amounts of foods, ingredients, and nutrients consumed. Overall, amounts or quantities of food, ingredients, and nutrients consumed can be measured in terms of volume, mass, or weight. Volume measures how much space the food occupies. Mass measures how much matter the food contains. Weight measures the pull of gravity on the food. The concepts of mass and weight are related, but not identical. Food, ingredient, or nutrient density can also be measured, sometimes as a step toward measuring food mass.

Volume can be expressed in metric units (such as cubic millimeters, cubic centimeters, or liters) or U.S. (historically English) units (such as cubic inches, teaspoons, tablespoons, cups, pints, quarts, gallons, or fluid ounces). Mass (and often weight in colloquial use) can be expressed in metric units (such as milligrams, grams, and kilograms) or U.S. (historically English) units (ounces or pounds). The density of specific ingredients or nutrients within food is sometimes measured in terms of the volume of specific ingredients or nutrients per total food volume or measured in terms of the mass of specific ingredients or nutrients per total food mass.

In an example, the amount of a specific ingredient or nutrient within (a portion of) food can be measured directly by a sensing mechanism. In an example, the amount of a specific ingredient or nutrient within (a portion of) food can be estimated indirectly by measuring the amount of food and then linking this amount of food to amounts of ingredients or nutrients using a database that links specific foods with standard amounts of ingredients or nutrients.

In an example, an amount of a selected type of food, ingredient, or nutrient consumed can be expressed as an absolute amount. In an example, an amount of a selected type of food, ingredient, or nutrient consumed can be expressed as a percentage of a standard amount. In an example, an amount of a selected type of food, ingredient, or nutrient consumed can be displayed as a portion of a standard amount such as in a bar chart, pie chart, thermometer graphic, or battery graphic.

In an example, a standard amount can be selected from the group consisting of: daily recommended minimum amount; daily recommended maximum amount or allowance; weekly recommended minimum amount; weekly recommended maximum amount or allowance; target amount to achieve a health goal; and maximum amount or allowance per meal. In an example, a standard amount can be a Reference Daily Intake (RDI) value or a Daily Reference Value.

In an example, the volume of food consumed can be estimated by analyzing one or more pictures of that food. In an example, volume estimation can include the use of a physical or virtual fiduciary marker or object of known size for estimating the size of a portion of food. In an example, a physical fiduciary marker can be placed in the field of view of an imaging system for use as a point of reference or a measure. In an example, this fiduciary marker can be a plate, utensil, or other physical place setting member of known size. In an example, this fiduciary marker can be created virtually by the projection of coherent light beams. In an example, a device can project (laser) light points onto food and, in conjunction with infrared reflection or focal adjustment, use those points to create a virtual fiduciary marker. A fiduciary marker may be used in conjunction with a distance-finding mechanism (such as infrared range finder) that determines the distance from the camera and the food.

In an example, volume estimation can include obtaining video images of food or multiple still pictures of food in order to obtain pictures of food from multiple perspectives. In an example, pictures of food from multiple perspectives can be used to create three-dimensional or volumetric models of that food in order to estimate food volume. In an example, such methods can be used prior to food consumption and again after food consumption, in order to estimate the volume of food consumed based on differences in food volume measured. In an example, food volume estimation can be done by analyzing one or more pictures of food before (and after) consumption. In an example, multiple pictures of food from different angles can enable three-dimensional modeling of food volume. In an example, multiple pictures of food at different times (such as before and after consumption) can enable estimation of the amount of proximal food that is actually consumed vs. just being served in proximity to the person.

In a non-imaging example of food volume estimation, a utensil or other apportioning device can be used to divide food into mouthfuls. Then, the number of times that the utensil is used to bring food up to the person's mouth can be tracked. Then, the number of utensil motions is multiplied times the estimated volume of food per mouthful in order to estimate the cumulative volume of food consumed. In an example, the number of hand motions or mouth motions can be used to estimate the quantity of food consumed. In an example, a motion sensor worn on a person's wrist or incorporated into a utensil can measure the number of hand-to-mouth motions. In an example, a motion sensor, sound sensor, or electromagnetic sensor in communication with a person's mouth can measure the number of chewing motions which, in turn, can be used to estimate food volume.

In an example, a device for measuring a person's consumption of one or more selected types of foods, ingredients, or nutrients can measure the weight or mass of food that the person consumes. In an example, a device and method for measuring consumption of one or more selected types of foods, ingredients, or nutrients can include a food scale that measures the weight of food. In an example a food scale can measure the weight of food prior to consumption and the weight of unconsumed food remaining after consumption in order to estimate the weight of food consumed based on the difference in pre vs. post consumption measurements. In an example, a food scale can be a stand-alone device. In an example, a food scale can be incorporated into a plate, glass, cup, glass coaster, place mat, or other place setting. In an example a plate can include different sections which separately measure the weights of different foods on the plate. In an example, a food scale embedded into a place setting or smart utensil can automatically transmit data concerning food weight to a computer.

In an example, a food scale can be incorporated into a smart utensil. In an example, a food scale can be incorporated into a utensil rest on which a utensil is placed for each bite or mouthful. In an example, a food scale can be incorporated into a smart utensil which tracks the cumulative weight of cumulative mouthfuls of food during an eating event. In an example, a smart utensil can approximate the weight of mouthfuls of food by measuring the effect of food carried by the utensil on an accelerometer or other inertial sensor. In an example, a smart utensil can incorporate a spring between the food-carrying portion and the hand-held portion of a utensil and food weight can be estimated by measuring distension of the spring as food is brought up to a person's mouth.

In an example, a smart utensil can use an inertial sensor, accelerometer, or strain gauge to estimate the weight of the food-carrying end of utensil at a first time (during an upswing motion as the utensil carries a mouthful of food up to the person's mouth), can use this sensor to estimate the weight of the food-carrying end of the utensil at a second time (during a downswing motion as the person lowers the utensil from their mouth), and can estimate the weight of the mouthful of food by calculating the difference in weight between the first and second times.

In an example, a device or system can measure nutrient density or concentration as part of an automatic food, ingredient, or nutrient identification method. In an example, such nutrient density can be expressed as the average amount of a specific ingredient or nutrient per unit of food weight. In an example, such nutrient density can be expressed as the average amount of a specific ingredient or nutrient per unit of food volume. In an example, food density can be estimated by interacting food with light, sound, or electromagnetic energy and measuring the results of this interaction. Such interaction can include energy absorption or reflection.

In an example, nutrient density can be determined by reading a label on packaging associated with food consumed. In an example, nutrient density can be determined by receipt of wirelessly transmitted information from a grocery store display, electronically-functional restaurant menu, or vending machine. In an example, food density can be estimated by ultrasonic scanning of food. In an example, food density and food volume can be jointly analyzed to estimate food weight or mass.

In an example, for some foods with standardized sizes (such as foods that are manufactured in standard sizes at high volume), food weight can be estimated as part of food identification. In an example, information concerning the weight of food consumed can be linked to nutrient quantities in a computer database in order to estimate cumulative consumption of selected types of nutrients.

In an example, a method for measuring a person's consumption of at least one selected type of food, ingredient, or nutrient can comprise monitoring changes in the volume or weight of food at a reachable location near the person. In an example, pictures of food can be taken at multiple times before, during, and after food consumption in order to better estimate the amount of food that the person actually consumes, which can differ from the amount of food served to the person or the amount of food left over after the person eats. In an example, estimates of the amount of food that the person actually consumes can be made by digital image subtraction and/or 3D modeling. In an example, changes in the volume or weight of nearby food can be correlated with hand motions in order to estimate the amount of food that a person actually eats. In an example, a device can track the cumulative number of hand-to-mouth motions, number of chewing motions, or number of swallowing motions. In an example, estimation of food consumed can also involve asking the person whether they ate all the food that was served to them.

In an example, a device and method for measuring a person's consumption of at least one selected type of food, ingredient, or nutrient can collect data that enables tracking the cumulative amount of a type of food, ingredient, or nutrient which the person consumes during a period of time (such as an hour, day, week, or month) or during a particular eating event. In an example, the time boundaries of a particular eating event can be defined by a maximum time between chews or mouthfuls during a meal and/or a minimum time between chews or mouthfuls between meals. In an example, the time boundaries of a particular eating event can be defined by Fourier Transformation analysis of the variable frequencies of chewing, swallowing, or biting during meals vs. between meals.

In an example, a device and method for measuring a person's consumption of at least one selected type of food, ingredient, or nutrient can track the cumulative amount of that food, ingredient, or nutrient consumed by the person and provide feedback to the person based on the person's cumulative consumption relative to a target amount. In an example, a device can provide negative feedback when a person exceeds a target amount of cumulative consumption. In an example, a device and system can sound an alarm or provide other real-time feedback to a person when the cumulative consumed amount of a selected type of food, ingredient, or nutrient exceeds an allowable amount (in total, per meal, or per unit of time).

In various examples, a target amount of consumption can be based on one or more factors selected from the group consisting of: the selected type of selected food, ingredient, or nutrient; amount of this type recommended by a health care professional or governmental agency; specificity or breadth of the selected nutrient type; the person's age, gender, and/or weight; the person's diagnosed health conditions; the person's exercise patterns and/or caloric expenditure; the person's physical location; the person's health goals and progress thus far toward achieving them; one or more general health status indicators; magnitude and/or certainty of the effects of past consumption of the selected nutrient on the person's health; the amount and/or duration of the person's consumption of healthy food or nutrients; changes in the person's weight; time of day; day of the week; occurrence of a holiday or other occasion involving special meals; dietary plan created for the person by a health care provider; input from a social network and/or behavioral support group; input from a virtual health coach; health insurance copay and/or health insurance premium; financial payments, constraints, and/or incentives; cost of food; speed or pace of nutrient consumption; and accuracy of the sensor in detecting the selected nutrient.

4. Food Consumption and Nutrient Identification Sensors

A device and method for measuring a person's consumption of at least one selected type of food, ingredient, or nutrient can include: a general food-consumption monitor that detects when a person is probably eating, but does not identify the selected types of foods, ingredients, or nutrients that the person is eating; and a food-identifying sensor that identifies the person's consumption of at least one selected type of food, ingredient, or nutrient.

In an example, operation of a food-identifying sensor can be triggered by the results of a general food-consumption monitor. In an example, a general food-consumption monitor with low privacy intrusion (but low food identification accuracy) can operate continually and trigger the operation of a food-identifying sensor with high privacy intrusion (but high food identification accuracy) when the person is eating. In an example, a general food-consumption monitor with low privacy intrusion (but low power or resource requirements) can operate continually and trigger the operation of a food-identifying sensor with high privacy intrusion (but high power or resource requirements) when the person is eating. In an example, the combination of a general food-consumption monitor and a food-identifying sensor can achieve relatively-high food identification accuracy with relatively-low privacy intrusion or resource requirements.

In an example, a food-consumption monitor or food-identifying sensor can measure food weight, mass, volume, or density. In an example, such a sensor can be a scale, strain gauge, or inertial sensor. In an example, such a sensor can measure the weight or mass of an entire meal, a portion of one type of food within that meal, or a mouthful of a type of food that is being conveyed to a person's mouth. In general, a weight, mass, or volume sensor is more useful for general detection of food consumption and food amount than it is for identification of consumption of selected types of foods, ingredients, and nutrients. However, it can be very useful when used in combination with a specific food-identifying sensor.

In an example, a food-consumption monitor can be a motion sensor. In various examples, a motion sensor can be selected from the group consisting of: bubble accelerometer, dual-axial accelerometer, electrogoniometer, gyroscope, inclinometer, inertial sensor, multi-axis accelerometer, piezoelectric sensor, piezo-mechanical sensor, pressure sensor, proximity detector, single-axis accelerometer, strain gauge, stretch sensor, and tri-axial accelerometer. In an example, a motion sensor can collect data concerning the movement of a person's wrist, hand, fingers, arm, head, mouth, jaw, or neck. In an example, analysis of this motion data can be used to identify when the person is probably eating. In general, a motion sensor is more useful for general detection of food consumption and food amount than it is for identification of consumption of selected types of foods, ingredients, and nutrients. However, it can be very useful when used in combination with a specific food-identifying sensor.

In an example, there can be an identifiable pattern of movement that is highly-associated with food consumption and a motion sensor can monitor a person's movements to identify times when the person is probably eating. In an example, this movement can include repeated movement of a person's hand up to their mouth. In an example, this movement can include a combination of three-dimensional roll, pitch, and yaw by a person's wrist and/or hand. In an example, this movement can include repeated bending of a person's elbow. In an example, this movement can include repeated movement of a person's jaws. In an example, this movement can include peristaltic motion of the person's esophagus that is detectable from contact with a person's neck.

In an example, a motion sensor can be used to estimate the quantity of food consumed based on the number of motion cycles. In an example, a motion sensor can be used to estimate the speed of food consumption based on the speed or frequency of motion cycles. In an example, a proximity sensor can detect when a person's hand gets close to their mouth. In an example, a proximity sensor can detect when a wrist (or hand or finger) is in proximity to a person's mouth. However, a proximity detector can be less useful than a motion detector because it does not identify complex three-dimensional motions that can differentiate eating from other hand-to-mouth motions such as coughing, yawning, smoking, and tooth brushing.

In various examples, a device to measure a person's consumption of at least one selected type of food, ingredient, or nutrient can include a motion sensor that collects data concerning movement of the person's body. In an example, this data can be used to detect when a person is consuming food. In an example, this data can be used to aid in the identification of what types and amounts of food the person is consuming. In an example, analysis of this data can be used to trigger additional data collection to resolve uncertainty concerning the types and amounts of food that the person is consuming.

In an example, a motion sensor can include one or more accelerometers, inclinometers, electrogoniometers, and/or strain gauges. In an example, movement of a person's body that can be monitored and analyzed can be selected from the group consisting of: finger movements, hand movements, wrist movements, arm movements, elbow movements, eye movements, and head movements; tilting movements, lifting movements; hand-to-mouth movements; angles of rotation in three dimensions around the center of mass known as roll, pitch and yaw; and Fourier Transformation analysis of repeated body member movements. In an example, each hand-to-mouth movement that matches a certain pattern can be used to estimate bite or mouthful of food. In an example, the speed of hand-to-mouth movements that match a certain pattern can be used to estimate eating speed. In an example, this pattern can include upward and tilting hand movement, followed by a pause, following by a downward and tilting hand movement.

In an example, a motion sensor that is used to detect food consumption can be worn on a person's wrist, hand, arm, or finger. In an example, a motion sensor can be incorporated into a smart watch, fitness watch, or watch phone. In an example, a fitness watch that already uses an accelerometer to measure motion for estimating caloric expenditure can also use an accelerometer to detect (and estimate the quantity of) food consumption.

Motion-sensing devices that are worn on a person's wrist, hand, arm, or finger can continuously monitor a person's movements to detect food consumption with high compliance and minimal privacy intrusion. They do not require that a person carry a particular piece of electronic equipment everywhere they go and consistently bring that piece of electronic equipment out for activation each time that they eat a meal or snack. However, a motion-detecting device that is worn constantly on a person's wrist, hand, arm, or finger can be subject to false alarms due to motions (such as coughing, yawning, smoking, and tooth brushing) that can be similar to eating motions. To the extent that there is a distinctive pattern of hand and/or arm movement associated with bringing food up to one's mouth, such a device can detect when food consumption is occurring.

In an example, a motion-sensing device that is worn on a person's wrist, hand, arm, or finger can measure how rapidly or often the person brings their hand up to their mouth. A common use of such information is to encourage a person to eat at a slower pace. The idea that a person will eat less if they eat at a slower pace is based on the lag between food consumption and the feeling of satiety from internal gastric organs. If a person eats slower, then they will tend to not overeat past the point of internal identification of satiety.

In an example, a smart watch, fitness watch, watch phone, smart ring, or smart bracelet can measure the speed, pace, or rate at which a person brings food up to their mouth while eating and provide feedback to the person to encourage them to eat slower if the speed, pace, or rate is high. In an example, feedback can be sound-based, such as an alarm, buzzer, or computer-generated voice. In an example, feedback can be tactile, such as vibration or pressure. In an example, such feedback can be visual, such as a light, image, or display screen. In an alternative example, eating speed can be inferred indirectly by a plate, dish, bowl, glass or other place setting member that measures changes in the weight of food on the member. Negative feedback can be provided to the person if the weight of food on the plate, dish, bowl, or glass decreases in a manner that indicates that food consumption is too fast.

In an example, a motion sensor that is used to detect food consumption can be incorporated into, or attached to, a food utensil such as a fork or spoon. A food utensil with a motion sensor can be less prone to false alarms than a motion sensor worn on a person's wrist, hand, arm, or finger because the utensil is only used when the person eats food. Since the utensil is only used for food consumption, analysis of complex motion and differentiation of food consumption actions vs. other hand gestures is less important with a utensil than it is with a device that is worn on the person's body. In an example, a motion sensor can be incorporated into a smart utensil. In an example, a smart utensil can estimate the amount of food consumed by the number of hand-to-mouth motions (combined with information concerning how much food is conveyed by the utensil with each movement). In an example, a smart utensil can encourage a person to eat slower. The idea is that if the person eats more slowly, then they will tend to not overeat past the point of internal identification of satiety.

In an example, a food-consumption monitor or food-identifying sensor can be a light-based sensor that records the interaction between light and food. In an example, a light-based sensor can be a camera, mobile phone, or other conventional imaging device that takes plain-light pictures of food. In an example, a light-based food consumption or identification sensor can comprise a camera that takes video pictures or still pictures of food. In an example, such a camera can take pictures of the interaction between a person and food, including food apportionment, hand-to-mouth movements, and chewing movements.

In an example, a device and method for measuring a person's consumption of at least one selected type of food, ingredient, or nutrient can include a camera, or other picture-taking device, that takes pictures of food. In the following section, we discuss different examples of how a camera or other imaging-device can be used to take pictures of food and how those pictures can be analyzed to identify the types and amounts of food consumed. After that section, we discuss some other light-based approaches to food identification (such as spectroscopy) that do not rely on conventional imaging devices and plain-light food pictures.

A food-consumption monitor or food-identifying sensor can be a camera or other imaging device that is carried and held by a person. In an example, a camera that is used for food identification can be part of a mobile phone, cell phone, electronic tablet, or smart food utensil. In an example, a food-consumption monitor or food-identifying sensor can be a camera or other imaging device that is worn on a person's body or clothing. In an example, a camera can be incorporated into a smart watch, smart bracelet, smart button, or smart necklace.

In an example, a camera that is used for monitoring food consumption and/or identifying consumption of at least one selected type of food, ingredient, or nutrient can be a dedicated device that is specifically designed for this purpose. In an example, a camera that is used for monitoring food consumption and/or identifying consumption of specific foods can be a part of a general purpose device (such as a mobile phone, cell phone, electronic tablet, or digital camera) and in wireless communication with a dedicated device for monitoring food consumption and identifying specific food types.

In an example, use of a hand-held camera, mobile phone, or other imaging device to identify food depends on a person's manually aiming and triggering the device for each eating event. In an example, the person must bring the imaging device with them to each meal or snack, orient it toward the food to be consumed, and activate taking a picture of the food by touch or voice command. In an example, a camera, smart watch, smart necklace or other imaging device that is worn on a person's body or clothing can move passively as the person moves. In an example, the field of vision of an imaging device that is worn on a person's wrist, hand, arm, or finger can move as the person brings food up to their mouth when eating. In an example, such an imaging device can passively capture images of a reachable food source and interaction between food and a person's mouth.

In another example, the imaging vector and/or focal range of an imaging device worn on a person's body or clothing can be actively and deliberately adjusted to better track the person's hands and mouth to better monitor for possible food consumption. In an example, a device can optically scan the space surrounding the person for reachable food sources, hand-to-food interaction, and food-to-mouth interaction. In an example, in the interest of privacy, an imaging device that is worn on a person's body or clothing can only take pictures when some other sensor or information indicates that the person is probably eating.

In an example, a camera that is used for identifying food consumption can have a variable focal length. In an example, the imaging vector and/or focal distance of a camera can be actively and automatically adjusted to focus on: the person's hands, space surrounding the person's hands, a reachable food source, a food package, a menu, the person's mouth, and the person's face. In an example, in the interest of privacy, the focal length of a camera can be automatically adjusted in order to focus on food and not other people.

In an example, a device for measuring a person's consumption of at least one selected type of food, ingredient, or nutrient can include an imaging component that the person must manually aim toward food and manually activate for taking food pictures (such as through touch or voice commands). In an example, the taking of food pictures in this manner requires at least one specific voluntary human action associated with each food consumption event, apart from the actual act of eating, in order to take pictures of food during that food consumption event. In an example, such specific voluntary human actions can be selected from the group consisting of: transporting a mobile imaging device to a meal; aiming an imaging device at food; clicking a button to activate picture taking; touching a screen to activate picture taking; and speaking a voice command to activate picture taking.

In an example, a device for measuring a person's consumption of at least one selected type of food, ingredient, or nutrient can prompt a person to take pictures of food when a non-imaging sensor or other source of information indicates that the person is probably eating. In an alternative example, a device for measuring a person's consumption of at least one selected type of food, ingredient, or nutrient can automatically take pictures of food consumed without the need for specific action by the person in association with a specific eating event apart from the act of eating.

In an example, a device and method for measuring food consumption can include taking multiple pictures of food. In an example, such a device and method can include taking pictures of food from at least two different angles in order to better segment a meal into different types of foods, estimate the three-dimensional volume of each type of food, and control for lighting and shading differences. In an example, a camera or other imaging device can take pictures of food from multiple perspectives to create a virtual three-dimensional model of food in order to determine food volume. In an example, an imaging device can estimate the quantities of specific foods from pictures or images of those foods by volumetric analysis of food from multiple perspectives and/or by three-dimensional modeling of food from multiple perspectives.

In an example, a camera can use an object of known size within its field of view as a fiduciary marker in order to measure the size or scale of food. In an example, a camera can use projected laser beams to create a virtual or optical fiduciary marker in order to measure food size or scale. In an example, pictures of food can be taken at different times. In an example, a camera can be used to take pictures of food before and after consumption. The amount of food that a person actually consumes (not just the amount ordered or served) can be estimated by the difference in observed food volume from the pictures before and after consumption.

In an example, images of food can be automatically analyzed in order to identify the types and quantities of food consumed. In an example, pictures of food taken by a camera or other picture-taking device can be automatically analyzed to estimate the types and amounts of specific foods, ingredients, or nutrients that a person is consumes. In an example, an initial stage of an image analysis system can comprise adjusting, normalizing, or standardizing image elements for better food segmentation, identification, and volume estimation. These elements can include: color, texture, shape, size, context, geographic location, adjacent food, place setting context, and temperature (infrared). In an example, a device can identify specific foods from pictures or images by image segmentation, color analysis, texture analysis, and pattern recognition.

In various examples, automatic identification of food types and quantities can be based on: color and texture analysis; image segmentation; image pattern recognition; volumetric analysis based on a fiduciary marker or other object of known size; and/or three-dimensional modeling based on pictures from multiple perspectives. In an example, a device can collect food images that are used to extract a vector of food parameters (such as color, texture, shape, and size) that are automatically associated with vectors of food parameters in a database of such parameters for food identification.

In an example, a device can collect food images that are automatically associated with images of food in a food image database for food identification. In an example, specific ingredients or nutrients that are associated with these selected types of food can be estimated based on a database linking foods to ingredients and nutrients. In another example, specific ingredients or nutrients can be measured directly. In various examples, a device for measuring consumption of food, ingredient, or nutrients can directly (or indirectly) measure consumption at least one selected type of food, ingredient, or nutrient.

In an example, food image information can be transmitted from a wearable or hand-held device to a remote location where automatic food identification occurs and the results can be transmitted back to the wearable or hand-held device. In an example, identification of the types and quantities of foods, ingredients, or nutrients that a person consumes from pictures of food can be a combination of, or interaction between, automated identification food methods and human-based food identification methods.

We now transition to discussion of light-based methods for measuring food consumption that do not rely of conventional imaging devices and plain-light images. Probably the simplest such method involves identifying food by scanning a barcode or other machine-readable code on the food's packaging (such as a Universal Product Code or European Article Number), on a menu, on a store display sign, or otherwise in proximity to food at the point of food selection, sale, or consumption. In an example, the type of food (and/or specific ingredients or nutrients within the food) can be identified by machine-recognition of a food label, nutritional label, or logo on food packaging, menu, or display sign. However, there are many types of food and food consumption situations in which food is not accompanied by such identifying packaging. Accordingly, a robust imaged-based device and method for measuring food consumption should not rely on bar codes or other identifying material on food packaging.

In an example, selected types of foods, ingredients, and/or nutrients can be identified by the patterns of light that are reflected from, or absorbed by, the food at different wavelengths. In an example, a light-based sensor can detect food consumption or can identify consumption of a specific food, ingredient, or nutrient based on the reflection of light from food or the absorption of light by food at different wavelengths. In an example, an optical sensor can detect fluorescence. In an example, an optical sensor can detect whether food reflects light at a different wavelength than the wavelength of light shone on food. In an example, an optical sensor can be a fluorescence polarization immunoassay sensor, chemiluminescence sensor, thermoluminescence sensor, or piezoluminescence sensor.

In an example, a light-based food-identifying sensor can collect information concerning the wavelength spectra of light reflected from, or absorbed by, food. In an example, an optical sensor can be a chromatographic sensor, spectrographic sensor, analytical chromatographic sensor, liquid chromatographic sensor, gas chromatographic sensor, optoelectronic sensor, photochemical sensor, and photocell. In an example, an optical sensor can analyze modulation of light wave parameters by the interaction of that light with a portion of food. In an example, an optical sensor can detect modulation of light reflected from, or absorbed by, a receptor when the receptor is exposed to food. In an example, an optical sensor can emit and/or detect white light, infrared light, or ultraviolet light.

In an example, a light-based food-identifying sensor can identify consumption of a selected type of food, ingredient, or nutrient with a spectral analysis sensor. In various examples, a food-identifying sensor can identify a selected type of food, ingredient, or nutrient with a sensor that detects light reflection spectra, light absorption spectra, or light emission spectra. In an example, a spectral measurement sensor can be a spectroscopy sensor or a spectrometry sensor. In an example, a spectral measurement sensor can be a white light spectroscopy sensor, an infrared spectroscopy sensor, a near-infrared spectroscopy sensor, an ultraviolet spectroscopy sensor, an ion mobility spectroscopic sensor, a mass spectrometry sensor, a backscattering spectrometry sensor, or a spectrophotometer. In an example, light at different wavelengths can be absorbed by, or reflected off, food and the results can be analyzed in spectral analysis.

In an example, a food-consumption monitor or food-identifying sensor can be a microphone or other type of sound sensor. In an example, a sensor to detect food consumption and/or identify consumption of a selected type of food, ingredient, or nutrient can be a sound sensor. In an example, a sound sensor can be an air conduction microphone or bone conduction microphone. In an example, a microphone or other sound sensor can monitor for sounds associated with chewing or swallowing food. In an example, data collected by a sound sensor can be analyzed to differentiate sounds from chewing or swallowing food from other types of sounds such as speaking, singing, coughing, and sneezing.

In an example, a sound sensor can include speech recognition or voice recognition to receive verbal input from a person concerning food that the person consumes. In an example, a sound sensor can include speech recognition or voice recognition to extract food selecting, ordering, purchasing, or consumption information from other sounds in the environment.

In an example, a sound sensor can be worn or held by a person. In an example, a sound sensor can be part of a general purpose device, such as a cell phone or mobile phone, which has multiple applications. In an example, a sound sensor can measure the interaction of sound waves (such as ultrasonic sound waves) and food in order to identify the type and quantity of food that a person is eating.

In an example, a food-consumption monitor or food-identifying sensor can be a chemical sensor. In an example, a chemical sensor can include a receptor to which at least one specific nutrient-related analyte binds and this binding action creates a detectable signal. In an example, a chemical sensor can include measurement of changes in energy wave parameters that are caused by the interaction of that energy with food. In an example, a chemical sensor can be incorporated into a smart utensil to identify selected types of foods, ingredients, or nutrients. In an example, a chemical sensor can be incorporated into a portable food probe to identify selected types of foods, ingredients, or nutrients. In an example, a sensor can analyze the chemical composition of a person's saliva. In an example, a chemical sensor can be incorporated into an intraoral device that analyzes microsamples of a person's saliva. In an example, such an intraoral device can be adhered to a person's upper palate.

In various examples, a food-consumption monitor or food-identifying sensor can be selected from the group consisting of: receptor-based sensor, enzyme-based sensor, reagent based sensor, antibody-based receptor, biochemical sensor, membrane sensor, pH level sensor, osmolality sensor, nucleic acid-based sensor, or DNA/RNA-based sensor; a biomimetic sensor (such as an artificial taste bud or an artificial olfactory sensor), a chemiresistor, a chemoreceptor sensor, a electrochemical sensor, an electroosmotic sensor, an electrophoresis sensor, or an electroporation sensor; a specific nutrient sensor (such as a glucose sensor, a cholesterol sensor, a fat sensor, a protein-based sensor, or an amino acid sensor); a color sensor, a colorimetric sensor, a photochemical sensor, a chemiluminescence sensor, a fluorescence sensor, a chromatography sensor (such as an analytical chromatography sensor, a liquid chromatography sensor, or a gas chromatography sensor), a spectrometry sensor (such as a mass spectrometry sensor), a spectrophotometer sensor, a spectral analysis sensor, or a spectroscopy sensor (such as a near-infrared spectroscopy sensor); and a laboratory-on-a-chip or microcantilever sensor.

In an example, a food-consumption monitor or food-identifying sensor can be an electromagnetic sensor. In an example, a device for measuring food consumption or identifying specific nutrients can emit and measure electromagnetic energy. In an example, a device can expose food to electromagnetic energy and collect data concerning the effects of this interaction which are used for food identification. In various examples, the results of this interaction can include measuring absorption or reflection of electromagnetic energy by food. In an example, an electromagnetic sensor can detect the modulation of electromagnetic energy that is interacted with food.

In an example, an electromagnetic sensor that detects food or nutrient consumption can detect electromagnetic signals from the body in response to the consumption or digestion of food. In an example, analysis of this electromagnetic energy can help to identify the types of food that a person consumes. In an example, a device can measure electromagnetic signals emitted by a person's stomach, esophagus, mouth, tongue, afferent nervous system, or brain in response to general food consumption. In an example, a device can measure electromagnetic signals emitted by a person's stomach, esophagus, mouth, tongue, afferent nervous system, or brain in response to consumption of selected types of foods, ingredients, or nutrients.

In various examples, a sensor to detect food consumption or identify consumption of a selected type of nutrient can be selected from the group consisting of: neuroelectrical sensor, action potential sensor, ECG sensor, EKG sensor, EEG sensor, EGG sensor, capacitance sensor, conductivity sensor, impedance sensor, galvanic skin response sensor, variable impedance sensor, variable resistance sensor, interferometer, magnetometer, RF sensor, electrophoretic sensor, optoelectronic sensor, piezoelectric sensor, and piezocapacitive sensor.

In an example, a sensor to monitor, detect, or sense food consumption or to identify a selected type of food, ingredient, or nutrient consumed can be pressure sensor or touch sensor. In an example, a pressure or touch sensor can sense pressure or tactile information from contact with food that will be consumed. In an example, a pressure or touch sensor can be incorporated into a smart food utensil or food probe. In an example, a pressure or touch based sensor can be incorporated into a pad on which a food utensil is placed between mouthfuls or when not in use. In an example, a pressure or touch sensor can sense pressure or tactile information from contact with a body member whose internal pressure or external shape is affected by food consumption. In various examples, a pressure or touch sensor can be selected from the group consisting of: food viscosity sensor, blood pressure monitor, muscle pressure sensor, button or switch on a food utensil, jaw motion pressure sensor, and hand-to-mouth contact sensor.

In an example, a food-consumption monitor or food-identifying sensor can be a thermal energy sensor. In an example, a thermal sensor can detect or measure the temperature of food. In an example, a thermal sensor can detect or measure the temperature of a portion of a person's body wherein food consumption changes the temperature of this member. In various examples, a food-consumption monitor can be selected from the group consisting of: a thermometer, a thermistor, a thermocouple, and an infrared energy detector.

In an example, a food-consumption monitor or food-identifying sensor can be a location sensor. In an example, such a sensor can be geographic location sensor or an intra-building location sensor. A device for detecting food consumption and/or identifying a selected type of food, ingredient, or nutrient consumed can use information concerning a person's location as part of the means for food consumption detection and/or food identification. In an example, a device can identify when a person in a geographic location that is associated with probable food consumption. In an example, a device can use information concerning the person's geographic location as measured by a global positioning system or other geographic location identification system. In an example, if a person is located at a restaurant with a known menu or at a store with a known food inventory, then information concerning this menu or food inventory can be used to narrow down the likely types of food being consumed. In an example, if a person is located at a restaurant, then the sensitivity of automated detection of food consumption can be adjusted. In an example, if a person is located at a restaurant or grocery store, then visual, auditory, or other information collected by a sensor can be interpreted within the context of that location.

In an example, a device can identify when a person is in a location within a building that is associated with probable food consumption. In an example, if a person is in a kitchen or in a dining room within a building, then the sensitivity of automated detection of food consumption can be adjusted.

In an example, a food-consumption monitoring system can increase the continuity or level of automatic data collection when a person is in a restaurant, in a grocery store, in a kitchen, or in a dining room. In an example, a person's location can be inferred from analysis of visual signals or auditory signals instead of via a global positioning system. In an example, a person's location can be inferred from interaction between a device and local RF beacons or local wireless networks.

In an example, a food-consumption monitor or food-identifying sensor can have a biological component. In an example, a food-identifying sensor can use biological or biomimetic components to identify specific foods, ingredients, or nutrients. In various examples, a food-identifying sensor can use one or more biological or biomimetic components selected from the group consisting of: biochemical sensor, antibodies or antibody-based chemical receptor, enzymes or enzyme-based chemical receptor, protein or protein-based chemical receptor, biomarker for a specific dietary nutrient, biomembrane or biomembrane-based sensor, porous polymer or filter paper containing a chemical reagent, nucleic acid-based sensor, polynucleotide-based sensor, artificial taste buds or biomimetic artificial tongue, and taste bud cells in communication with an electromagnetic sensor.

In an example, a food-consumption monitor or food-identifying sensor can be a taste or smell sensor. In an example, a sensor can be an artificial taste bud that emulates the function of a natural taste bud. In an example, a sensor can be an artificial olfactory receptor that emulates the function of a natural olfactory receptor. In an example, a sensor can comprise biological taste buds or olfactory receptors that are configured to be in electrochemical communication with an electronic device. In an example, a sensor can be an electronic tongue. In an example, a sensor can be an electronic nose.

In an example, a food-consumption monitor or food-identifying sensor can be a high-energy sensor. In an example, a high-energy sensor can identify a selected type of food, ingredient, or nutrient based on the interaction of microwaves or x-rays with a portion of food. In various examples a high-energy sensor to detect food consumption or identify consumption of a selected type of nutrient can be selected from the group consisting of: a microwave sensor, a microwave spectrometer, and an x-ray detector.

In an example, a person's consumption of food or the identification of a selected type of food, ingredient, or nutrient can be done by a sensor array. A sensor array can comprise multiple sensors of different types. In an example, multiple sensors in a sensor array can operate simultaneously in order to jointly identify food consumption or to jointly identify a selected type of food, ingredient, or nutrient. In an example, a sensor array can comprise multiple cross-reactive sensors. In an example, different sensors in a sensor array can operate independently to identify different types of foods, ingredients, or nutrients. In an example, a single sensor can detect different types of foods, ingredients, or nutrients.

In various examples, a food-consumption monitor or food-identifying sensor can be selected from the group consisting of: chemical sensor, biochemical sensor, amino acid sensor, chemiresistor, chemoreceptor, photochemical sensor, optical sensor, chromatography sensor, fiber optic sensor, infrared sensor, optoelectronic sensor, spectral analysis sensor, spectrophotometer, olfactory sensor, electronic nose, metal oxide semiconductor sensor, conducting polymer sensor, quartz crystal microbalance sensor, electromagnetic sensor, variable impedance sensor, variable resistance sensor, conductance sensor, neural impulse sensor, EEG sensor, EGG sensor, EMG sensor, interferometer, galvanic skin response sensor, cholesterol sensor, HDL sensor, LDL sensor, electrode, neuroelectrical sensor, neural action potential sensor, Micro Electrical Mechanical System (MEMS) sensor, laboratory-on-a-chip, or medichip, micronutrient sensor, osmolality sensor, protein-based sensor or reagent-based sensor, saturated fat sensor or trans fat sensor, action potential sensor, biological sensor, enzyme-based sensor, protein-based sensor, reagent-based sensor, camera, video camera, fixed focal-length camera, variable focal-length camera, pattern recognition sensor, microfluidic sensor, motion sensor, accelerometer, flow sensor, strain gauge, electrogoniometer, inclinometer, peristalsis sensor, multiple-analyte sensor array, an array of cross-reactive sensors, pH level sensor, sodium sensor, sonic energy sensor, microphone, sound-based chewing sensor, sound-based swallow sensor, ultrasonic sensor, sugar sensor, glucose sensor, temperature sensor, thermometer, and thermistor.

In an example, a sensor to monitor, detect, or sense food consumption or to identify consumption of a selected type of food, ingredient, or nutrient can be a wearable sensor that is worn by the person whose food consumption is monitored, detected, or sensed. In an example, a wearable food-consumption monitor or food-identifying sensor can be worn directly on a person's body. In an example a wearable food-consumption monitor or food-identifying sensor can be worn on, or incorporated into, a person's clothing.

In various examples, a wearable sensor can be worn on a person in a location selected from the group consisting of: wrist, neck, finger, hand, head, ear, eyes, nose, teeth, mouth, torso, chest, waist, and leg. In various examples, a wearable sensor can be attached to a person or to a person's clothing by a means selected from the group consisting of: strap, clip, clamp, snap, pin, hook and eye fastener, magnet, and adhesive.

In various examples, a wearable sensor can be worn on a person in a manner like a clothing accessory or piece of jewelry selected from the group consisting of: wristwatch, wristphone, wristband, bracelet, cufflink, armband, armlet, and finger ring; necklace, neck chain, pendant, dog tags, locket, amulet, necklace phone, and medallion; eyewear, eyeglasses, spectacles, sunglasses, contact lens, goggles, monocle, and visor; clip, tie clip, pin, brooch, clothing button, and pin-type button; headband, hair pin, headphones, ear phones, hearing aid, earring; and dental appliance, palatal vault attachment, and nose ring.

In an example, a sensor to monitor, detect, or sense food consumption or to identify consumption of a selected type of food, ingredient or nutrient can be a utensil-based sensor such as a spoon or fork. In an example, a utensil-based food-consumption monitor or food-identifying sensor can be attached to a generic food utensil. In an example, a utensil-based sensor can be incorporated into specialized "smart utensil." In an example, a sensor can be attached to, or incorporated into a smart fork or smart spoon. In an example, a sensor can be attached to, or incorporated into, a beverage holding member such as a glass, cup, mug, or can. In an example, a food-identifying sensor can be incorporated into a portable food probe.

In an example, a device to measure a person's consumption of at least one selected type of food, ingredient, or nutrient can comprise one or more sensors that are integrated into a place setting. In various examples, sensors can be integrated into one or more of the following place setting members: plate, glass, cup, bowl, serving dish, place mat, fork, spoon, knife, and smart utensil. In various examples, a place setting member can incorporate a sensor selected from the group consisting of: scale, camera, chemical receptor, spectroscopy sensor, infrared sensor, electromagnetic sensor. In an example, a place setting member with an integrated food sensor can collect data concerning food with which the place setting member is in contact at different times. In an example, changes in measurements concerning food at different times can be used to estimate the amount of food that a person is served, the amount of food that a person actually eats, and the amount of left-over food that a person does not eat.

In an example, a sensor to detect food consumption or to identify consumption of a selected type of food, ingredient, or nutrient can be incorporated into a multi-purpose mobile electronic device such as a cell phone, mobile phone, smart phone, smart watch, electronic tablet device, electronic book reader, electronically-functional jewelry, or other portable consumer electronics device. In an example, a smart phone application can turn the camera function of a smart phone into a means of food identification. In an example, such a smart phone application can be in wireless communication with a wearable device that is worn by the person whose food consumption is being measured.

In an example, a wearable device can prompt a person to collect information concerning food consumption using a smart phone application. In an example, a wearable device can automatically activate a smart phone or other portable electronic device to collect information concerning food consumption. In an example, a wearable device can automatically trigger a smart phone or other portable electronic device to start recording audio information using the smart phone's microphone when the wearable device detects that the person is probably eating. In an example, a wearable device can automatically trigger a smart phone or other portable electronic device to start recording visual information using the smart phone's camera when the wearable device detects that the person is probably eating.

In an example, a food-consumption monitor or specific food-identifying sensor can monitor, detect, and/or analyze chewing or swallowing actions by a person. In particular, such a monitor or sensor can differentiate between chewing and swallowing actions that are probably associated with eating vs. other activities. In various examples, chewing or swallowing can be monitored, detected, sensed, or analyzed based on sonic energy (differentiated from speaking, talking, singing, coughing, or other non-eating sounds), motion (differentiated from speaking or other mouth motions), imaging (differentiated from other mouth-related activities) or electromagnetic energy (such as electromagnetic signals from mouth muscles). There are differences in food consumed per chew or per swallow between people, and even for the same person over time, based on the type of food, the person's level of hunger, and other variables. This can make it difficult to estimate the amount of food consumed based only on the number of chews or swallows.

In an example, a food-consumption monitor or food-identifying sensor can monitor a particular body member. In various examples, such a monitor or sensor can be selected from the group consisting of: a blood monitor (for example using a blood pressure monitor, a blood flow monitor, or a blood glucose monitor); a brain monitor (such as an electroencephalographic monitor); a heart monitor (such as electrocardiographic monitor, a heartbeat monitor, or a pulse rate monitor); a mouth function monitor (such as a chewing sensor, a biting sensor, a jaw motion sensor, a swallowing sensor, or a saliva composition sensor); a muscle function monitor (such as an electromyographic monitor or a muscle pressure sensor); a nerve monitor or neural monitor (such as a neural action potential monitor, a neural impulse monitor, or a neuroelectrical sensor); a respiration monitor (such as a breathing monitor, an oxygen consumption monitor, an oxygen saturation monitor, a tidal volume sensor, or a spirometry monitor); a skin sensor (such as a galvanic skin response monitor, a skin conductance sensor, or a skin impedance sensor); and a stomach monitor (such as an electrogastrographic monitor or a stomach motion monitor). In various examples, a sensor can monitor sonic energy or electromagnetic energy from selected portions of a person's gastrointestinal tract (ranging from the mouth to the intestines) or from nerves which innervate those portions. In an example, a monitor or sensor can monitor peristaltic motion or other movement of selected portions of a person's gastrointestinal tract.

In an example, a monitor or sensor to detect food consumption or to identify a selected type of food, ingredient, or nutrient can be a micro-sampling sensor. In an example, a micro-sampling sensor can automatically extract and analyze micro-samples of food, intra-oral fluid, saliva, intra-nasal air, chyme, or blood. In an example, a micro-sampling sensor can collect and analyze micro-samples periodically. In an example, a micro-sampling sensor can collect and analyze micro-samples randomly. In an example, a micro-sampling sensor can collect and analyze micro-samples when a different sensor indicates that a person is probably consuming food. In an example, a micro-sampling sensor can be selected from the group consisting of: microfluidic sampling system, microfluidic sensor array, and micropump.

In an example, a sensor to detect food consumption and/or identify consumption of a selected type of food, ingredient, or nutrient can incorporate microscale or nanoscale technology. In various examples, a sensor to detect food consumption or identify a specific food, ingredient, or nutrient can be selected from the group consisting of: micro-cantilever sensor, microchip sensor, microfluidic sensor, nano-cantilever sensor, nanotechnology sensor, Micro Electrical Mechanical System (MEMS) sensor, laboratory-on-a-chip, and medichip.

5. Smart Watch or Other Wearable Component

In an example, a food-consumption monitor or food-identifying sensor can be incorporated into a smart watch or other device that is worn on a person's wrist. In an example, a food-consumption monitor or food-identifying sensor can be worn on, or attached to, other members of a person's body or to a person's clothing. In an example, a device for measuring a person's consumption of at least one selected type of food, ingredient, or nutrient can be worn on, or attached to, a person's body or clothing. In an example, a device can be worn on, or attached to, a part of a person's body that is selected from the group consisting of: wrist (one or both), hand (one or both), or finger; neck or throat; eyes (directly such as via contact lens or indirectly such as via eyewear); mouth, jaw, lips, tongue, teeth, or upper palate; arm (one or both); waist, abdomen, or torso; nose; ear; head or hair; and ankle or leg.

In an example, a device for measuring a person's consumption of at least one selected type of food, ingredient, or nutrient can be worn in a manner similar to a piece of jewelry or accessory. In various examples, a food consumption measuring device can be worn in a manner similar to a piece of jewelry or accessory selected from the group consisting of: smart watch, wrist band, wrist phone, wrist watch, fitness watch, or other wrist-worn device; finger ring or artificial finger nail; arm band, arm bracelet, charm bracelet, or smart bracelet; smart necklace, neck chain, neck band, or neck-worn pendant; smart eyewear, smart glasses, electronically-functional eyewear, virtual reality eyewear, or electronically-functional contact lens; cap, hat, visor, helmet, or goggles; smart button, brooch, ornamental pin, clip, smart beads; pin-type, clip-on, or magnetic button; shirt, blouse, jacket, coat, or dress button; head phones, ear phones, hearing aid, ear plug, or ear-worn bluetooth device; dental appliance, dental insert, upper palate attachment or implant; tongue ring, ear ring, or nose ring; electronically-functional skin patch and/or adhesive patch; undergarment with electronic sensors; head band, hair band, or hair clip; ankle strap or bracelet; belt or belt buckle; and key chain or key ring.

In an example, a device for measuring a person's consumption of at least one selected type of food, ingredient, or nutrient can be incorporated or integrated into an article of clothing or a clothing-related accessory. In various examples, a device for measuring food consumption can be incorporated or integrated into one of the following articles of clothing or clothing-related accessories: belt or belt buckle; neck tie; shirt or blouse; shoes or boots; underwear, underpants, briefs, undershirt, or bra; cap, hat, or hood; coat, jacket, or suit; dress or skirt; pants, jeans, or shorts; purse; socks; and sweat suit.

In an example, a device for measuring a person's consumption of at least one selected type of food, ingredient, or nutrient can be attached to a person's body or clothing. In an example, a device to measure food consumption can be attached to a person's body or clothing using an attachment means selected from the group consisting of: band, strap, chain, hook and eye fabric, ring, adhesive, bracelet, buckle, button, clamp, clip, elastic band, eyewear, magnet, necklace, piercing, pin, string, suture, tensile member, wrist band, and zipper. In an example, a device can be incorporated into the creation of a specific article of clothing. In an example, a device to measure food consumption can be integrated into a specific article of clothing by a means selected from the group consisting of: adhesive, band, buckle, button, clip, elastic band, hook and eye fabric, magnet, pin, pocket, pouch, sewing, strap, tensile member, and zipper.

In an example, a wearable device for measuring a person's consumption of at least one selected type of food, ingredient, or nutrient can comprise one or more sensors selected from the group consisting of: motion sensor, accelerometer (single multiple axis), electrogoniometer, or strain gauge; optical sensor, miniature still picture camera, miniature video camera, miniature spectroscopy sensor; sound sensor, miniature microphone, speech recognition software, pulse sensor, ultrasound sensor; electromagnetic sensor, skin galvanic response (Galvanic Skin Response) sensor, EMG sensor, chewing sensor, swallowing sensor; temperature sensor, thermometer, infrared sensor; and chemical sensor, chemical sensor array, miniature spectroscopy sensor, glucose sensor, cholesterol sensor, or sodium sensor.

In an example, a device and system for measuring a person's consumption of at least one selected type of food, ingredient, or nutrient can be entirely wearable or include a wearable component. In an example, a wearable device or component can be worn directly on a person's body, can be worn on a person's clothing, or can be integrated into a specific article of clothing. In an example, a wearable device for measuring food consumption can be in wireless communication with an external device. In various examples, a wearable device for measuring food consumption can be in wireless communication with an external device selected from the group consisting of: a cell phone, an electronic tablet, electronically-functional eyewear, a home electronics portal, an internet portal, a laptop computer, a mobile phone, a remote computer, a remote control unit, a smart phone, a smart utensil, a television set, and a virtual menu system.

In an example, a wearable device for measuring a person's consumption of at least one selected type of food, ingredient, or nutrient can comprise multiple components selected from the group consisting of: Central Processing Unit (CPU) or microprocessor; food-consumption monitoring component (motion sensor, electromagnetic sensor, optical sensor, and/or chemical sensor); graphic display component (display screen and/or coherent light projection); human-to-computer communication component (speech recognition, touch screen, keypad or buttons, and/or gesture recognition); memory component (flash, RAM, or ROM); power source and/or power-transducing component; time keeping and display component; wireless data transmission and reception component; and strap or band.

6. Smart Utensil, Mobile Phone, or Other Hand-Held Component

In an example, a device, method, and system for measuring consumption of selected types of foods, ingredients, or nutrients can include a hand-held component in addition to a wearable component. In an example, a hand-held component can be linked or combined with a wearable component to form an integrated system for measuring a person's consumption of at least one selected type of food, ingredient, or nutrient. In an example, the combination and integration of a wearable member and a hand-held member can provide advantages that are not possible with either a wearable member alone or a hand-held member alone. In an example, a wearable member of such a system can be a food-consumption monitor. In an example, a hand-held member of such a system can be a food-identifying sensor.

In an example, a wearable member can continually monitor to detect when the person is consuming food, wherein this continual monitoring does not significantly intrude on the person's privacy. In an example, a hand-held member may be potentially more intrusive with respect to privacy when it operates, but is only activated to operate when food consumption is detected by the wearable member. In an example, wearable and hand-held components of such a system can be linked by wireless communication. In an example, wearable and held-held components of such a system can be physically linked by a flexible wire. In an example, a hand-held component can be removably attached to the wearable member and detached for use in identifying at least one selected type of food, ingredient, or nutrient.

In an example, a hand-held component of a device or system for measuring a person's consumption of at least one selected type of food, ingredient, or nutrient can be a hand-held smart food utensil or food probe. In an example, a hand-held component of a device or system for measuring a person's consumption of at least one selected type of food, ingredient, or nutrient can be a hand-held mobile phone or other general consumer electronics device that performs multiple functions. In an example, a mobile phone application can link or integrate the operation of the mobile phone with the operation of a wearable component of a system for measuring a person's consumption of at least one selected type of food, ingredient, or nutrient.

In various examples, a hand-held component can be selected from the group consisting of: smart utensil, smart spoon, smart fork, smart food probe, smart bowl, smart chop stick, smart dish, smart glass, smart plate, electronically-functional utensil, electronically-functional spoon, electronically-functional fork, electronically-functional food probe, electronically-functional bowl, electronically-functional chop stick, electronically-functional dish, electronically-functional glass, electronically-functional plate, smart phone, mobile phone, cell phone, electronic tablet, and digital camera.

In various examples, a food-consumption monitoring and nutrient identifying system can comprise a combination of a wearable component and a hand-held component that is selected from the group consisting of: smart watch and smart food utensil; smart watch and food probe; smart watch and mobile phone; smart watch and electronic tablet; smart watch and digital camera; smart bracelet and smart food utensil; smart bracelet and food probe; smart bracelet and mobile phone; smart bracelet and electronic tablet; smart bracelet and digital camera; smart necklace and smart food utensil; smart necklace and food probe; smart necklace and mobile phone; smart necklace and electronic tablet; and smart necklace and digital camera.

In an example, a wearable food-consumption monitor (such as may be embodied in a smart watch, smart bracelet, or smart necklace) and a hand-held food-identifying sensor (such as may be embodied in a smart utensil, food probe, or smart phone) can be linked or combined together into an integrated system for measuring a person's consumption of at least one selected type of food, ingredient, or nutrient. In an example, wearable and held-held components such a system can be separate components that are linked by wireless communication. In an example, wearable and held-held components of such a system can be physically connected by a flexible element. In an example, wearable and hand-held components can be physically attached or detached for use. In an example, a hand-held component can be a removable part of a wearable component for easier portability and increased user compliance for all eating events. In an example, a smart utensil or food probe can be removed from a wearable component to identify food prior to, or during consumption. This can increase ease of use and user compliance with food identification for all eating events.

A smart food utensil can be a food utensil that is specifically designed to help measure a person's consumption of at least one selected type of food, ingredient, or nutrient. In an example, a smart utensil can be a food utensil that is equipped with electronic and/or sensory functionality. In an example, a smart food utensil can be designed to function like a regular food utensil, but is also enhanced with sensors in order to detect food consumption and/or identify consumption of selected types of foods, ingredients, or nutrients.

A regular food utensil can be narrowly defined as a tool that is commonly used to convey a single mouthful of food up to a person's mouth. In this narrow definition, a food utensil can be selected from the group consisting of: fork, spoon, spork, and chopstick. In an example, a food utensil can be more broadly defined as a tool that is used to apportion food into mouthfuls during food consumption or to convey a single mouthful of food up to a person's mouth during food consumption. This broader definition includes cutlery and knives used at the time of food consumption in addition to forks, spoons, sporks, and chopsticks.

In an example, a food utensil may be more broadly defined to also include tools and members that are used to convey amounts of food that are larger than a single mouthful and to apportion food into servings prior to food consumption by an individual. Broadly defined in such a manner, a food utensil can be selected from the group consisting of: fork, spoon, spork, knife, chopstick, glass, cup, mug, straw, can, tablespoon, teaspoon, ladle, scoop, spatula, tongs, dish, bowl, and plate. In an example, a smart utensil is an electronically-functional utensil. In an example, a smart utensil can be a utensil with one or built-in functions selected from the group consisting of: detecting use to convey food; detecting food consumption; measuring the speed, rate, or pace of food consumption; measuring the amount of food consumed; identifying the type of food consumed; and communicating information concerning food consumption to other devices or system components.

In an example, a food-consumption monitor or food-identifying sensor can be incorporated into, or attached to, a food utensil. In an example, such a sensor can be an integral part of a specialized smart utensil that is specifically designed to measure food consumption or detect consumption of at least one selected type of food, ingredient, or nutrient. In an example, such a sensor can be designed to be removably attached to a generic food utensil so that any generic utensil can be used. In an example, a sensor can be attached to a generic utensil by tension, a clip, an elastic band, magnetism, or adhesive.

In an example, such a sensor, or a smart utensil of which this sensor is a part, can be in wireless communication with a smart watch or other member that is worn on a person's wrist, hand, or arm. In this manner, a system or device can tell if a person is using the smart utensil when they eat based on the relative movements and/or proximity of a smart utensil to a smart watch. In an example, a smart utensil can be a component of a multi-component system to measure of person's consumption of at least one selected type of food, ingredient, or nutrient.

In an example, a smart food utensil or food probe can identify the types and amounts of consumed foods, ingredients, or nutrients by being in optical communication with food. In an example, a smart food utensil can identify the types and amounts of food consumed by taking pictures of food. In an example, a smart food utensil can take pictures of food that is within a reachable distance of a person. In an example, a smart food utensil can take pictures of food on a plate. In an example, a smart food utensil can take pictures of a portion of food as that food is conveyed to a person's mouth via the utensil.

In an example, a smart food utensil can identify the type of food by optically analyzing food being consumed. In an example, a smart food utensil can identify the types and amounts of food consumed by recording the effects light that is interacted with food. In an example, a smart food utensil can identify the types and amounts of food consumed via spectroscopy. In an example, a smart food utensil can perform spectroscopic analysis of a portion of food as that food is conveyed to a person's mouth via the utensil. In an example, a smart food utensil can measure the amount of food consumed using a photo-detector.

In an example, a smart food utensil or food probe can identify the types and amounts of consumed foods, ingredients, or nutrients by performing chemical analysis of food. In an example, a smart food utensil can identify the types and amounts of food consumed by performing chemical analysis of the chemical composition of food. In an example, a smart food utensil can collect data that is used to analyze the chemical composition of food by direct contact with food. In an example, a smart food utensil can identify the type of food, ingredient, or nutrient being consumed by being in fluid or gaseous communication with food. In an example, a smart food utensil can include an array of chemical sensors with which a sample of food interacts.

In an example, a smart food utensil can collect data that is used to analyze the chemical composition of food by measuring the absorption of light, sound, or electromagnetic energy by food that is in proximity to the person whose consumption is being monitored. In an example, a smart food utensil can collect data that is used to analyze the chemical composition of food by measuring the reflection of light, sound, or electromagnetic energy by food that is in proximity to the person whose consumption is being monitored. In an example, a smart food utensil can collect data that is used to analyze the chemical composition of food by measuring the reflection of different wavelengths of light, sound, or electromagnetic energy by food that is in proximity to the person whose consumption is being monitored.

In an example, a smart food utensil can identify the types and amounts of food consumed by measuring the effects of interacting food with electromagnetic energy. In an example, a smart food utensil can estimate the amount of food that a person consumes by tracking utensil motions with an accelerometer. In various examples, one or more sensors that are part of, or attached to, a smart food utensil can be selected from the group consisting of: motion sensor, accelerometer, strain gauge, inertial sensor, scale, weight sensor, or pressure sensor; miniature camera, video camera, optical sensor, optoelectronic sensor, spectrometer, spectroscopy sensor, or infrared sensor; chemical sensor, chemical receptor array, or spectroscopy sensor; microphone, sound sensor, or ultrasonic sensor; and electromagnetic sensor, capacitive sensor, inductance sensor, or piezoelectric sensor.

In an example, a wearable member (such as a smart watch) can continually monitor for possible food consumption, but a smart utensil is only used when the person is eating. In an example, a device or system for measuring food consumption can compare the motion of a smart utensil with the motion of a wearable member (such as a smart watch) in order to detect whether the smart utensil is being properly used whenever the person is eating food. In an example, a device or system for measuring food consumption can track the movement of a smart utensil that a person should use consistently to eat food, track the movement of a wearable motion sensor (such as a smart watch) that a person wears continuously, and compare the movements to determine whether the person always uses the smart utensil to eat. In an example, this device or system can prompt the person to use the smart utensil when comparison of the motion of the smart utensil with the motion of a wearable motion sensor (such as a smart watch) indicates that the person is not using the smart utensil when they are eating.

In an example, a device or system for measuring food consumption can monitor the proximity of a smart utensil to a wearable member (such as a smart watch) in order to detect whether the smart utensil is being properly used whenever the person is eating food. In an example, this device or system can prompt the person to use the smart utensil when lack of proximity between the smart utensil and a wearable member (such as a smart watch) indicates that the person is not using the smart utensil when they are eating. In an example, a device or system for measuring food consumption can detect if a smart utensil is attached to, or near to, a smart watch. In an example, a device or system for measuring food consumption can prompt a person to use a smart utensil if the smart utensil is not attached to, or near to, a smart watch when the person is eating.

In an example, a food-consumption monitoring and nutrient identifying system can include a hand-held component that is selected from the group consisting of: smart phone, mobile phone, cell phone, holophone, or application of such a phone; electronic tablet, other flat-surface mobile electronic device, Personal Digital Assistant (PDA), or laptop; digital camera; and smart eyewear, electronically-functional eyewear, or augmented reality eyewear. In an example, such a hand-held component can be in wireless communication with a wearable component of such a system. In an example, a device, method, or system for detecting food consumption or measuring consumption of a selected type of food, ingredient, or nutrient can include integration with a general-purpose mobile device that is used to collects data concerning food consumption. In an example, the hand-held component of such a system can be a general purpose device, of which collecting data for food identification is only one among many functions that it performs. In an example, a system for measuring a person's consumption of at least one selected type of food, ingredient, or nutrient can comprise: a wearable member that continually monitors for possible food consumption; a hand-held smart phone that is used to take pictures of food that will be consumed; wireless communication between the wearable member and the smart phone; and software that integrates the operation of the wearable member and the smart phone.

In an example, the hand-held component of a food-consumption monitoring and nutrient identifying system can be a general purpose smart phone which collects information concerning food by taking pictures of food. In an example, this smart phone can be in wireless communication with a wearable component of the system, such as a smart watch. In an example, the hand-held component of such a system must be brought into physical proximity with food that will be consumed in order to measure the results of interaction between food and light, sound, or electromagnetic energy.

In an example, a hand-held component of such a system requires voluntary action by a person in order to collect data for food identification in association with each eating event apart from the actual act of eating. In an example, a mobile phone must be pointed toward food by a person and triggered to take pictures of that food. In an example, a hand-held component of such a system must be brought into fluid or gaseous communication with food in order to chemically analyze the composition of food. In an example, a wearable member (such as a smart watch) can continually monitor for possible food consumption, but a smart phone is only used for food identification when the person is eating. In an example, this device or system can prompt the person to use a smart phone for food identification when the person is eating.

In an example, a smart phone can identify the types and amounts of consumed foods, ingredients, or nutrients by being in optical communication with food. In an example, a smart phone can collect information for identifying the types and amounts of food consumed by taking pictures of food. In an example, a smart phone can take pictures of food that is within a reachable distance of a person. In an example, a smart phone can take pictures of food on a plate.

In an example, a smart phone can collect data that is used to analyze the chemical composition of food by measuring the absorption of light, sound, or electromagnetic energy by food that is in proximity to the person whose consumption is being monitored. In an example, a smart phone can collect data that is used to analyze the chemical composition of food by measuring the reflection of different wavelengths of light, sound, or electromagnetic energy by food that is in proximity to the person whose consumption is being monitored. In various examples, one or more sensors that are part of, or attached to, a smart phone can be selected from the group consisting of: miniature camera, video camera, optical sensor, optoelectronic sensor, spectrometer, spectroscopy sensor, and infrared sensor.

7. User Interface

In an example, a device for measuring a person's consumption of at least one selected type of food, ingredient, or nutrient can include a human-to-computer interface for communication from a human to a computer. In various examples, a device for measuring a person's consumption of at least one selected type of food, ingredient, or nutrient can include a human-to-computer interface selected from the group consisting of: speech recognition or voice recognition interface; touch screen or touch pad; physical keypad/keyboard, virtual keypad or keyboard, control buttons, or knobs; gesture recognition interface or holographic interface; motion recognition clothing; eye movement detector, smart eyewear, and/or electronically-functional eyewear; head movement tracker; conventional flat-surface mouse, 3D blob mouse, track ball, or electronic stylus; graphical user interface, drop down menu, pop-up menu, or search box; and neural interface or EMG sensor.

In an example, such a human-to-computer interface can enable a user to directly enter information concerning food consumption. In an example, such direct communication of information can occur prior to food consumption, during food consumption, and/or after food consumption. In an example, such a human-to-computer interface can enable a user to indirectly collect information concerning food consumption. In an example, such indirect collection of information can occur prior to food consumption, during food consumption, and/or after food consumption.

In an example, a device for measuring a person's consumption of at least one selected type of food, ingredient, or nutrient can include a computer-to-human interface for communication from a computer to a human. In an example, a device and method for monitoring and measuring a person's food consumption can provide feedback to the person. In an example, a computer-to-human interface can communicate information about the types and amounts of food that a person has consumed, should consume, or should not consume. In an example, a computer-to-human interface can provide feedback to a person concerning their eating habits and the effects of those eating habits. In an example, this feedback can prompt the person to collect more information concerning the types and amounts of food that the person is consuming. In an example, a computer-to-human interface can be used to not just provide information concerning eating behavior, but also to change eating behavior.

In various examples, a device for measuring a person's consumption of at least one selected type of food, ingredient, or nutrient can provide feedback to the person that is selected from the group consisting of: auditory feedback (such as a voice message, alarm, buzzer, ring tone, or song); feedback via computer-generated speech; mild external electric charge or neural stimulation; periodic feedback at a selected time of the day or week; phantom taste or smell; phone call; pre-recorded audio or video message by the person from an earlier time; television-based messages; and tactile, vibratory, or pressure-based feedback.

In various examples, a device for measuring a person's consumption of at least one selected type of food, ingredient, or nutrient can provide feedback to the person that is selected from the group consisting of: feedback concerning food consumption (such as types and amounts of foods, ingredients, and nutrients consumed, calories consumed, calories expended, and net energy balance during a period of time); information about good or bad ingredients in nearby food; information concerning financial incentives or penalties associated with acts of food consumption and achievement of health-related goals; information concerning progress toward meeting a weight, energy-balance, and/or other health-related goal; information concerning the calories or nutritional components of specific food items; and number of calories consumed per eating event or time period.

In various examples, a device for measuring a person's consumption of at least one selected type of food, ingredient, or nutrient can provide feedback to the person that is selected from the group consisting of: augmented reality feedback (such as virtual visual elements superimposed on foods within a person's field of vision); changes in a picture or image of a person reflecting the likely effects of a continued pattern of food consumption; display of a person's progress toward achieving energy balance, weight management, dietary, or other health-related goals; graphical display of foods, ingredients, or nutrients consumed relative to standard amounts (such as embodied in pie charts, bar charts, percentages, color spectrums, icons, emoticons, animations, and morphed images); graphical representations of food items; graphical representations of the effects of eating particular foods; holographic display; information on a computer display screen (such as a graphical user interface); lights, pictures, images, or other optical feedback; touch screen display; and visual feedback through electronically-functional eyewear.

In various examples, a device for measuring a person's consumption of at least one selected type of food, ingredient, or nutrient can provide feedback to the person that is selected from the group consisting of: advice concerning consumption of specific foods or suggested food alternatives (such as advice from a dietician, nutritionist, nurse, physician, health coach, other health care professional, virtual agent, or health plan); electronic verbal or written feedback (such as phone calls, electronic verbal messages, or electronic text messages); live communication from a health care professional; questions to the person that are directed toward better measurement or modification of food consumption; real-time advice concerning whether to eat specific foods and suggestions for alternatives if foods are not healthy; social feedback (such as encouragement or admonitions from friends and/or a social network); suggestions for meal planning and food consumption for an upcoming day; and suggestions for physical activity and caloric expenditure to achieve desired energy balance outcomes.

8. Power Source and Wireless Communication

In an example, a wearable and/or hand-held member of a device for measuring a person's consumption of at least one selected type of food, ingredient, or nutrient can comprise multiple components selected from the group consisting of: a food-consumption monitor or food-identifying sensor; a central processing unit (CPU) such as a microprocessor; a database of different types of food and food attributes; a memory to store, record, and retrieve data such as the cumulative amount consumed for at least one selected type of food, ingredient, or nutrient; a communications member to transmit data to from external sources and to receive data from external sources; a power source such as a battery or power transducer; a human-to-computer interface such as a touch screen, keypad, or voice recognition interface; and a computer-to-human interface such as a display screen or voice-producing interface.

In an example, the power source for a wearable and/or hand-held member of a device for measuring a person's consumption of at least one selected type of food, ingredient, or nutrient can be selected from the group consisting of:

power from a power source that is internal to the device during regular operation (such as an internal battery, capacitor, energy-storing microchip, or wound coil or spring); power that is obtained, harvested, or transduced from a power source other than the person's body that is external to the device (such as a rechargeable battery, electromagnetic inductance from external source, solar energy, indoor lighting energy, wired connection to an external power source, ambient or localized radiofrequency energy, or ambient thermal energy); and power that is obtained, harvested, or transduced from the person's body (such as kinetic or mechanical energy from body motion, electromagnetic energy from the person's body, blood flow or other internal fluid flow, glucose metabolism, or thermal energy from the person's body.

In an example, a device or system for measuring a person's consumption of at least one selected type of food, ingredient, or nutrient can include one or more communications components for wireless transmission and reception of data. In an example, multiple communications components can enable wireless communication (including data exchange) between separate components of such a device and system. In an example, a communications component can enable wireless communication with an external device or system. In various examples, the means of this wireless communication can be selected from the group consisting of: radio transmission, Bluetooth transmission, Wi-Fi, and infrared energy.

In various examples, a device and system for measuring food consumption can be in wireless communication with an external device or system selected from the group consisting of: internet portal; smart phone, mobile phone, cell phone, holophone, or application of such a phone; electronic tablet, other flat-surface mobile electronic device, Personal Digital Assistant (PDA), remote control unit, or laptop; smart eyewear, electronically-functional eyewear, or augmented reality eyewear; electronic store display, electronic restaurant menu, or vending machine; and desktop computer, television, or mainframe computer. In various examples, a device can receive food-identifying information from a source selected from the group consisting of: electromagnetic transmissions from a food display or RFID food tag in a grocery store, electromagnetic transmissions from a physical menu or virtual user interface at a restaurant, and electromagnetic transmissions from a vending machine.

In an example, data concerning food consumption that is collected by a wearable or hand-held device can be analyzed by a data processing unit within the device in order to identify the types and amounts of foods, ingredients, or nutrients that a person consumes. In an example, data concerning food consumption that is collected by a smart watch can be analyzed within the housing of the watch. In an example, data concerning food consumption that is collected by a smart food utensil can be analyzed within the housing of the utensil.

In another example, data concerning food consumption that is collected by a wearable or hand-held device can be transmitted to an external device or system for analysis at a remote location. In an example, pictures of food can be transmitted to an external device or system for food identification at a remote location. In an example, chemical analysis results can be transmitted to an external device or system for food identification at a remote location. In an example, the results of analysis at a remote location can be transmitted back to a wearable or hand-held device.

9. Automatic Food Identification

In an example, a device for measuring a person's consumption of at least one selected type of food, ingredient, or nutrient can identify and track the selected types and amounts of foods, ingredients, or nutrients that the person consumes in an entirely automatic manner. In an example, such identification can occur in a partially automatic manner in which there is interaction between automated and human identification methods.

In an example, a device for measuring a person's consumption of at least one selected type of food, ingredient, or nutrient can identify and track food consumption at the point of selection or point of sale. In an example, a device for monitoring food consumption or consumption of selected types of foods, ingredients, or nutrients can approximate such measurements by tracking a person's food selections and purchases at a grocery store, at a restaurant, or via a vending machine. Tracking purchases can be relatively easy to do, since financial transactions are already well-supported by existing information technology. In an example, such tracking can be done with specific methods of payment, such as a credit card or bank account. In an example, such tracking can be done with electronically-functional food identification means such as bar codes, RFID tags, or electronically-functional restaurant menus. Electronic communication for food identification can also occur between a food-consumption monitoring device and a vending machine.

In an example, a device for measuring a person's consumption of at least one selected type of food, ingredient, or nutrient can identify food using information from a food's packaging or container. In an example, this information can be detected optically by means of a picture or optical scanner. In an example, food can be identified directly by automated optical recognition of information on food packaging, such as a logo, label, or barcode. In various examples, optical information on a food's packaging or container that is used to identify the type and/or amount of food can be selected from the group consisting of: bar code, food logo, food trademark design, nutritional label, optical text recognition, and UPC code. With respect to meals ordered at restaurants, some restaurants (especially fast-food restaurants) have standardized menu items with standardized food ingredients. In such cases, identification of types and amounts of food, ingredients, or nutrients can be conveyed at the point of ordering (via an electronically-functional menu) or purchase (via purchase transaction). In an example, food can be identified directly by wireless information received from a food display, RFID tag, electronically-functional restaurant menu, or vending machine. In an example, food or its nutritional composition can be identified directly by wireless transmission of information from a food display, menu, food vending machine, food dispenser, or other point of food selection or sale and a device that is worn, held, or otherwise transported with a person.

However, there are limitations to estimating food consumption based on food selections or purchases in a store or restaurant. First, a person might not eat everything that they purchase through venues that are tracked by the system. The person might purchase food that is eaten by their family or other people and might throw out some of the food that they purchase. Second, a person might eat food that they do not purchase through venues that are tracked by the system. The person might purchase some food with cash or in venues that are otherwise not tracked. The person might eat food that someone else bought, as when eating as a guest or family member. Third, timing differences between when a person buys food and when they eat it, especially for non-perishable foods, can confound efforts to associate caloric intake with caloric expenditure to manage energy balance during a defined period of time. For these reasons, a robust device for measuring food consumption should (also) be able to identify food at the point of consumption.

In an example, a device, method, or system for measuring a person's consumption of at least one selected type of food, ingredient, or nutrient can identify and track a person's food consumption at the point of consumption. In an example, such a device, method, or system can include a database of different types of food. In an example, such a device, method, or system can be in wireless communication with an externally-located database of different types of food. In an example, such a database of different types of food and their associated attributes can be used to help identify selected types of foods, ingredients, or nutrients. In an example, a database of attributes for different types of food can be used to associate types and amounts of specific ingredients, nutrients, and/or calories with selected types and amounts of food.

In an example, such a database of different types of foods can include one or more elements selected from the group consisting of: food color, food name, food packaging bar code or nutritional label, food packaging or logo pattern, food picture (individually or in combinations with other foods), food shape, food texture, food type, common geographic or intra-building locations for serving or consumption, common or standardized ingredients (per serving, per volume, or per weight), common or standardized nutrients (per serving, per volume, or per weight), common or standardized size (per serving), common or standardized number of calories (per serving, per volume, or per weight), common times or special events for serving or consumption, and commonly associated or jointly-served foods.

In an example, a picture of a meal as a whole can be automatically segmented into portions of different types of food for comparison with different types of food in a food database. In an example, the boundaries between different types of food in a picture of a meal can be automatically determined to segment the meal into different food types before comparison with pictures in a food database. In an example, a picture of a meal with multiple types of food can be compared as a whole with pictures of meals with multiple types of food in a food database. In an example, a picture of a food or a meal comprising multiple types of food can be compared directly with pictures of food in a food database.

In an example, a picture of food or a meal comprising multiple types of food can be adjusted, normalized, or standardized before it is compared with pictures of food in a food database. In an example, food color can be adjusted, normalized, or standardized before comparison with pictures in a food database. In an example, food size or scale can be adjusted, normalized, or standardized before comparison with pictures in a food database. In an example, food texture can be adjusted, normalized, or standardized before comparison with pictures in a food database. In an example, food lighting or shading can be adjusted, normalized, or standardized before comparison with pictures in a food database.

In an example, a food database can be used to identify the amount of calories that are associated with an identified type and amount of food. In an example, a food database can be used to identify the type and amount of at least one selected type of food that a person consumes. In an example, a food database can be used to identify the type and amount of at least one selected type of ingredient that is associated with an identified type and amount of food. In an example, a food database can be used to identify the type and amount of at least one selected type of nutrient that is associated with an identified type and amount of food. In an example, an ingredient or nutrient can be associated with a type of food on a per-portion, per-volume, or per-weight basis.

In an example, a vector of food characteristics can be extracted from a picture of food and compared with a database of such vectors for common foods. In an example, analysis of data concerning food consumption can include comparison of food consumption parameters between a specific person and a reference population. In an example, data analysis can include analysis of a person's food consumption patterns over time. In an example, such analysis can track the cumulative amount of at least one selected type of food, ingredient, or nutrient that a person consumes during a selected period of time.

In various examples, data concerning food consumption can be analyzed to identify and track consumption of selected types and amounts of foods, ingredients, or nutrient consumed using one or more methods selected from the group consisting of: linear regression and/or multivariate linear regression, logistic regression and/or probit analysis, Fourier transformation and/or fast Fourier transform (FFT), linear discriminant analysis, non-linear programming, analysis of variance, chi-squared analysis, cluster analysis, energy balance tracking, factor analysis, principal components analysis, survival analysis, time series analysis, volumetric modeling, neural network and machine learning.

In an example, a device for measuring a person's consumption of at least one selected type of food, ingredient, or nutrient can identify the types and amounts of food consumed in an automated manner based on images of that food. In various examples, food pictures can be analyzed for automated food identification using methods selected from the group consisting of: image attribute adjustment or normalization; inter-food boundary determination and food portion segmentation; image pattern recognition and comparison with images in a food database to identify food type; comparison of a vector of food characteristics with a database of such characteristics for different types of food; scale determination based on a fiduciary marker and/or three-dimensional modeling to estimate food quantity; and association of selected types and amounts of ingredients or nutrients with selected types and amounts of food portions based on a food database that links common types and amounts of foods with common types and amounts of ingredients or nutrients. In an example, automated identification of selected types of food based on images and/or automated association of selected types of ingredients or nutrients with that food can occur within a wearable or hand-held device. In an example, data collected by a wearable or hand-held device can be transmitted to an external device where automated identification occurs and the results can then be transmitted back to the wearable or hand-held device.

In an example, a device and system for measuring a person's consumption of at least one selected type of food, ingredient, or nutrient can take pictures of food using a digital camera. In an example, a device and system for measuring a person's consumption of at least one selected type of food, ingredient, or nutrient can take pictures of food using an imaging device selected from the group consisting of: smart watch, smart bracelet, fitness watch, fitness bracelet, watch phone, bracelet phone, wrist band, or other wrist-worn device; arm bracelet; and smart ring or finger ring. In an example, a device and system for measuring a person's consumption of at least one selected type of food, ingredient, or nutrient can take pictures of food using an imaging device selected from the group consisting of: smart phone, mobile phone, cell phone, holophone, and electronic tablet.

In an example, a device and system for measuring a person's consumption of at least one selected type of food, ingredient, or nutrient can take pictures of food using an imaging device selected from the group consisting of: smart glasses, visor, or other eyewear; electronically-functional glasses, visor, or other eyewear; augmented reality glasses, visor, or other eyewear; virtual reality glasses, visor, or other eyewear; and electronically-functional contact lens. In an example, a device and system for measuring a person's consumption of at least one selected type of food, ingredient, or nutrient can take pictures of food using an imaging device selected from the group consisting of: smart utensil, fork, spoon, food probe, plate, dish, or glass; and electronically-functional utensil, fork, spoon, food probe, plate, dish, or glass. In an example, a device and system for measuring a person's consumption of at least one selected type of food, ingredient, or nutrient can take pictures of food using an imaging device selected from the group consisting of: smart necklace, smart beads, smart button, neck chain, and neck pendant.

In an example, an imaging device can take multiple still pictures or moving video pictures of food. In an example, an imaging device can take multiple pictures of food from different angles in order to perform three-dimensional analysis or modeling of the food to better determine the volume of food. In an example, an imaging device can take multiple pictures of food from different angles in order to better control for differences in lighting and portions of food that are obscured from some perspectives. In an example, an imaging device can take multiple pictures of food from different angles in order to perform three-dimensional modeling or volumetric analysis to determine the three-dimensional volume of food in the picture. In an example, an imaging device can take multiple pictures of food at different times, such as before and after an eating event, in order to better determine how much food the person actually ate (as compared to the amount of food served). In an example, changes in the volume of food in sequential pictures before and after consumption can be compared to the cumulative volume of food conveyed to a person's mouth by a smart utensil to determine a more accurate estimate of food volume consumed. In various examples, a person can be prompted by a device to take pictures of food from different angles or at different times.

In an example, a device that identifies a person's food consumption based on images of food can receive food images from an imaging component or other imaging device that the person holds in their hand to operate. In an example, a device that identifies a person's food consumption based on images of food can receive food images from an imaging component or other imaging device that the person wears on their body or clothing. In an example, a wearable imaging device can be worn in a relatively fixed position on a person's neck or torso so that it always views the space in front of a person. In an example, a wearable imaging device can be worn on a person's wrist, arm, or finger so that the field of vision of the device moves as the person moves their arm, wrist, and/or fingers. In an example, a device with a moving field of vision can monitor both hand-to-food interaction and hand-to-mouth interaction as the person moves their arm, wrist, and/or hand. In an example, a wearable imaging device can comprise a smart watch with a miniature camera that monitors the space near a person's hands for possible hand-to-food interaction and monitors the near a person's mouth for hand-to-mouth interaction.

In an example, selected attributes or parameters of a food image can be adjusted, standardized, or normalized before the food image is compared to images in a database of food images or otherwise analyzed for identifying the type of food. In various examples, these image attributes or parameters can be selected from the group consisting of: food color, food texture, scale, image resolution, image brightness, and light angle.

In an example, a device and system for identifying types and amounts of food consumed based on food images can include the step of automatically segmenting regions of a food image into different types or portions of food. In an example, a device and system for identifying types and amounts of food consumed based on food images can include the step of automatically identifying boundaries between different types of food in an image that contains multiple types or portions of food. In an example, the creation of boundaries between different types of food and/or segmentation of a meal into different food types can include edge detection, shading analysis, texture analysis, and three-dimensional modeling. In an example, this process can also be informed by common patterns of jointly-served foods and common boundary characteristics of such jointly-served foods.

In an example, estimation of specific ingredients or nutrients consumed from information concerning food consumed can be done using a database that links specific foods (and quantities thereof) with specific ingredients or nutrients (and quantities thereof). In an example, food in a picture can be classified and identified based on comparison with pictures of known foods in a food image database. In an example, such food identification can be assisted by pattern recognition software. In an example, types and quantities of specific ingredients or nutrients can be estimated from the types and quantities of food consumed.

In an example, attributes of food in an image can be represented by a multi-dimensional food attribute vector. In an example, this food attribute vector can be statistically compared to the attribute vector of known foods in order to automate food identification. In an example, multivariate analysis can be done to identify the most likely identification category for a particular portion of food in an image. In various examples, a multi-dimensional food attribute vector can include attributes selected from the group consisting of: food color; food texture; food shape; food size or scale; geographic location of selection, purchase, or consumption; timing of day, week, or special event; common food combinations or pairings; image brightness, resolution, or lighting direction; infrared light reflection; spectroscopic analysis; and person-specific historical eating patterns.

10. Primary and Secondary Data Collection

In an example, a method for measuring a person's consumption of at least one selected type of food, ingredient, or nutrient can comprise collecting primary data concerning food consumption and collecting secondary data concerning food consumption. In an example, a device and system for measuring a person's consumption of at least one selected type of food, ingredient, or nutrient can comprise a primary data collection component and a secondary data collection component. In an example, primary data and secondary data can be jointly analyzed to identify the types and amounts of foods, ingredients, or nutrients that a person consumes.

In an example, primary data collection can occur automatically, without the need for any specific action by a person in association with a specific eating event, apart from the actual act of eating. In an example, a primary data component can operate automatically, without the need for any specific action by the person in association with a specific eating event apart from the actual act of eating. In an example, primary data is collected continuously, but secondary data is only collected when primary data indicates that a person is probably eating food. In an example, a primary data collection component operates continuously, but a secondary data collection component only operates when primary data indicates that a person is probably eating food.

In an example, primary data is collected automatically, but secondary data is only collected when triggered, activated, or operated by a person via a specific action in association with a specific eating event other than the act of eating. In an example, a primary data collection component operates automatically, but a secondary data collection component only operates when it is triggered, activated, or operated by a person via a specific action in association with a specific eating event other than the act of eating.

In an example, collection of secondary data can require a specific triggering or activating action by a person, apart from the act of eating, for each specific eating event. In an example, a device to measure food consumption can prompt a person to trigger, activate, or operate secondary data collection in association with a specific eating event when analysis of primary data indicates that this person is probably eating. In an example, a device to measure food consumption can prompt a person to trigger, activate, or operate a secondary data collection component in association with a specific eating event when analysis of primary data indicates that this person is probably eating. In an example, a component of this device that automatically collects primary data to detect when a person is probably eating can prompt the person to collect secondary data to identify food consumed when the person is probably eating. In an example, a device can prompt a person to collect secondary data in association with a specific eating event when analysis of primary data indicates that the person is probably eating and the person has not yet collected secondary data.

In an example, primary data can be collected by a wearable member and secondary data can be collected by a hand-held member. In an example, a person can be prompted to use a hand-held member to collect secondary data when primary data indicates that this person is probably eating. In an example, the wearable member can detect when a person is eating something, but is not very good at identifying what selected types of food the person is eating. In an example, the hand-held member is better at identifying what selected types of food the person is eating, but only when the hand-held member is used, which requires specific action by the person for each eating event.

In an example, a device and system can prompt a person to use a hand-held member (such as a mobile phone or smart utensil) to take pictures of food when a wearable member (such as a smart watch or smart bracelet) indicates that the person is probably eating. In an example, a person can be prompted to use a digital camera to take pictures of food when a wearable food-consumption monitor detects that the person is consuming food.

In an example, a person can be prompted to use a smart utensil to take pictures of food when a wearable food-consumption monitor detects that the person is consuming food. In an example, a device and system can prompt a person to use a hand-held member (such as a smart utensil or food probe) to analyze the chemical composition of food when a wearable member (such as a smart watch or smart bracelet) indicates that the person is probably eating. In an example, a person can be prompted to use a smart utensil for chemical analysis of food when a wearable food-consumption monitor detects that the person is consuming food.

In an example, a device for measuring food consumption can prompt a person to collect secondary data in real time, while a person is eating, when food consumption is indicated by primary data. In an example, a device for measuring food consumption can prompt a person to collect secondary data after food consumption, after food consumption has been indicated by primary data. In various examples, a device can prompt a person to take one or more actions to collect secondary data that are selected from the group consisting of: use a specific smart utensil for food consumption; use a specific set of smart place setting components (dish, plate, utensils, glass, etc) to record information about types and quantities of food; use a special food scale; touch food with a food probe or smart utensil; take a still picture or multiple still pictures of food from different angles; record a video of food from different angles; and expose food to light, electromagnetic, microwave, sonic, or other energy and record the results of interaction between food and this energy.

In an example, the process of collecting primary data can be less intrusive than the process of collecting secondary data with respect to a person's privacy. In an example, secondary data can enable more accurate food identification than primary data with respect to measuring a person's consumption of at least one selected type of food, ingredient, or nutrient. In an example, a coordinated system of primary and secondary data collection can achieve a greater level of measurement accuracy for a selected level of privacy intrusion than either primary data collection or secondary data collection alone. In an example, a coordinated system of primary and secondary data collection can achieve a lower level of privacy intrusion for a selected level of measurement accuracy than either primary data collection or secondary data collection alone.

In an example, primary data can be collected by a device or device component that a person wears on their body or clothing. In an example, primary data can be collected by a smart watch, smart bracelet, or other wrist-worn member. In an example, primary data can be collected by a smart necklace or other neck-worn member. In an example, primary data can be collected by smart glasses or other electronically-functional eyewear. In an example, primary data can be data concerning a person's movements that is collected using a motion detector. In an example, a primary data collection component can monitor a person's movements for movements that indicate that the person is probably eating food. In an example, primary data can be data concerning electromagnetic signals from a person's body. In an example, a primary data collection component can monitor electromagnetic signals from the person's body for signals that indicate that the person is probably eating food.

In an example, secondary data can be collected by a device or device component that a person holds in their hand. In an example, secondary data can be collected by a smart phone, mobile phone, smart utensil, or smart food probe. In an example, secondary data can be images of food. In an example, collection of secondary data can require that the person aim a camera at food and take one or more pictures of food. In an example, a camera-based food-identifying sensor automatically starts taking pictures when data collected by the monitor indicates that a person is probably consuming food, but the person is prompted to manually aim the camera toward food being consumed when data collected by the monitor indicates that a person is probably consuming food.

In an example, secondary data can be the results of chemical analysis of food. In an example, collection of secondary data can require that the person bring a nutrient-identifying utensil or sensor into physical contact with food. In an example, collection of secondary data can require that the person speak into a voice-recognizing device and verbally identify the food that they are eating. In an example, collection of secondary data can require that the person use a computerized menu-interface to identify the food that they are eating.

In an example, a device for measuring a person's consumption of at least one selected type of food, ingredient, or nutrient can collect primary data concerning food consumption without the need for a specific action by the person in association with an eating event apart from the act of eating. In an example, a device for measuring a person's consumption of at least one selected type of food, ingredient, or nutrient can collect primary data automatically. In an example, a device for measuring a person's consumption of at least one selected type of food, ingredient, or nutrient can collect primary data continually.

In an example, a device for measuring a person's consumption of at least one selected type of food, ingredient, or nutrient automatically collects secondary data concerning food consumption during a specific eating event, but only when analysis of primary data indicates that the person is eating. In an example, a device for measuring a person's consumption of at least one selected type of food, ingredient, or nutrient only collects secondary data concerning food consumption during a specific eating when it is triggered, activated, or operated by the person for that eating event by an action apart from the act of eating. In an example, a device can prompt the person to trigger, activate, or operate secondary data collection when primary data indicates that the person is eating.

In an example, a device for measuring a person's food consumption can automatically start collecting secondary data when primary data detects: reachable food sources; hand-to-food interaction; physical location in a restaurant, kitchen, dining room, or other location associated with probable food consumption; hand or arm motions associated with bringing food up to the person's mouth; physiologic responses by the person's body that are associated with probable food consumption; smells or sounds that are associated with probable food consumption; and/or speech patterns that are associated with probable food consumption.

In an example, a device for measuring a person's food consumption can prompt a person to collect secondary data when primary data detects: reachable food sources; hand-to-food interaction; physical location in a restaurant, kitchen, dining room, or other location associated with probable food consumption; hand or arm motions associated with bringing food up to the person's mouth; physiologic responses by the person's body that are associated with probable food consumption; smells or sounds that are associated with probable food consumption; and/or speech patterns that are associated with probable food consumption.

In an example, a device for measuring a person's consumption of at least one selected type of food, ingredient, or nutrient can include a combination of food identification methods or steps that are performed automatically by a computer and food identification methods or steps that are performed by a human. In an example, a device and method for detecting food consumption and identifying consumption of specific ingredients or nutrients can comprise multiple types of data collection and analysis involving interaction between automated analysis and human entry of information. In an example, a person can play a role in segmenting an image of a multi-food meal into different types of food by creating a virtual boundary between foods, such as by moving their finger across a touch-screen image of the meal. In an example, the person may review images of food consumed after an eating event and manually enter food identification information. In an example, a person can select one or more food types and/or quantities from a menu provided in response to a picture or other recorded evidence of an eating event.

In an example, redundant food identification can be performed by both a computer and a human during a calibration period, after which food identification is performed only by a computer. In an example, a device and system can automatically calibrate sensors and responses based on known quantities and outcomes. In an example, a person can eat food with known amounts of specific ingredients or nutrients. In an example, measured amounts can be compared to known amounts in order to calibrate device or system sensors. In an example, a device and system can track actual changes in a person's weight or Body Mass Index (BMI) and use these actual changes to calibrate device or system sensors. In an example, a device or system for measuring a person's consumption of at least one specific food, ingredient, or nutrient can be capable of adaptive machine learning. In an example, such a device or system can include a neural network. In an example, such a device and system can iteratively adjust the weights given to human responses based on feedback and health outcomes In an example, initial estimates of the types and amounts of food consumed can be made by a computer in an automated manner and then refined by human review as needed. In an example, if automated methods for identification of the types and amounts of food consumed do not produce results with a required level of certainty, then a device and system can prompt a person to collect and/or otherwise provide supplemental information concerning the types of food that the person is consuming. In an example, a device and system can track the accuracy of food consumption information provided by an automated process vs. that provided by a human by comparing predicted to actual changes in a person's weight. In an example, the relative weight which a device and system places on information from automated processes vs. information from human input can be adjusted based on their relatively accuracy in predicting weight changes. Greater weight can be given to the information source which is more accurate based on empirical validation.

In an example, a device can ask a person clarifying questions concerning food consumed. In an example, a device can prompt the person with queries to refine initial automatically-generated estimates of the types and quantities of food consumed. In an example, these questions can be asked in real time, as a person is eating, or in a delayed manner, after a person has finished eating or at a particular time of the day. In an example, the results of preliminary automated food identification can be presented to a human via a graphical user interface and the human can then refine the results using a touch screen. In an example, the results of automated food identification can be presented to a human via verbal message and the human can refine the results using a speech recognition interface. In an example, data can be transmitted (such as by the internet) to a review center where food is identified by a dietician or other specialist. In various examples, a human-to-computer interface for entering information concerning food consumption can comprise one or more interface elements selected the group consisting of: microphone, speech recognition, and/or voice recognition interface; touch screen, touch pad, keypad, keyboard, buttons, or other touch-based interface; camera, motion recognition, gesture recognition, eye motion tracking, or other motion detection interface; interactive food-identification menu with food pictures and names; and interactive food-identification search box.

In an example, a device and method for measuring consumption of a selected type of food, ingredient, or nutrient can comprise: a wearable motion sensor that is worn by a person that automatically collects data concerning the person's body motion, wherein this body motion data is used to determine when this person is consuming food; and a user interface that prompts the person to provide additional information concerning the selected types of foods, ingredients, or nutrients that the person is eating when the body motion data indicates that the person is consuming food.

In an example, a device and method for measuring consumption of a selected type of food, ingredient, or nutrient can comprise: a wearable sound sensor that is worn by a person that automatically collects data concerning sounds from the person's body or the environment, wherein this sound data is used to determine when this person is consuming food; and a user interface that prompts the person to provide additional information concerning the selected types of foods, ingredients, or nutrients that the person is eating when the sound data indicates that the person is consuming food.

In an example, a device and method for measuring consumption of a selected type of food, ingredient, or nutrient can comprise: a wearable imaging sensor that is worn by a person that automatically collects image data, wherein this image data is used to determine when this person is consuming food; and a user interface that prompts the person to provide additional information concerning the selected types of foods, ingredients, or nutrients that the person is eating when the imaging data indicates that the person is consuming food.

In an example, a device for measuring a person's consumption of at least one selected type of food, ingredient, or nutrient can comprise a wearable camera that continually takes pictures of the space surrounding a person. In an example, a camera can continually track the locations of a person's hands and only focus on the space near those hands to detect possible hand-and-food interaction. In an example, a device for monitoring a person's food consumption can optically monitor the space around a person for reachable food sources that may result in food consumption. In an example, a device for monitoring a person's food consumption can monitor the person's movements for hand-to-mouth gestures that may indicate food consumption.

In an example, a device can automatically recognize people within its range of vision and restrict picture focal range or content to not record pictures of people. In an example, this camera can automatically defocus images of other people for the sake of privacy. As an alternative way to address privacy issues, this camera can only be triggered to take record pictures when there are visual, sonic, olfactory, or locational indicators that the person is eating food or likely to eat food. As another way to address privacy issues, this camera can have a manual shut-off that the person can use to shut off the camera.

In an example, a wearable device and system for measuring a person's consumption of at least one selected type of food, ingredient, or nutrient can be tamper resistant. In an example, a wearable device can detect when it has been removed from the person's body by monitoring signals from the body such as pulse, motion, heat, skin electromagnetism, or proximity to an implanted device. In an example, a wearable device for measuring food consumption can detect if it has been removed from the person's body by detecting a lack of motion, lack of a pulse, and/or lack of electromagnetic response from skin. In various examples, a wearable device for measuring food consumption can continually monitor optical, electromagnetic, temperature, pressure, or motion signals that indicate that the device is properly worn by a person. In an example, a wearable device can trigger feedback if the device is removed from the person and the signals stop.

In an example, a wearable device for measuring food consumption can detect if its mode of operation becomes impaired. In an example, a wearable device for measuring food consumption that relies on taking pictures of food can detect if its line-of-sight to a person's hands or mouth is blocked. In an example, a wearable device can automatically track the location of a person's hands or mouth and can trigger feedback if this tracking is impaired. In an example, wrist-worn devices can be worn on both wrists to make monitoring food consumption more inclusive and to make it more difficult for a person to circumvent detection of food consumption by the combined devices or system. In an example, a wearable device for measuring food consumption that relies on a smart food utensil can detect if a person is consuming food without using the smart utensil. In an example, a device or system can detect when a utensil or food probe is not in functional linkage with wearable member. In an example, functional linkage can be monitored by common movement, common sound patterns, or physical proximity. In an example, a device or system can trigger feedback or behavioral modification if its function is impaired.

In an example, a person can be prompted to use a hand-held food-identifying sensor to identify the type of food being consumed when a smart watch detects that the person is consuming food and the hand-held food-identifying sensor is not already being used. In an example, a device and system for monitoring, sensing, detecting, and/or tracking a person's consumption of one or more selected types of foods, ingredients, or nutrients can comprise a wearable food-consumption monitor (such as a smart watch or smart necklace) and a hand-held food-identifying sensor (such as a smart utensil or smart phone), wherein data collected by the monitor and sensor are jointly analyzed to measure the types and amounts of specific foods, ingredients, and/or nutrients that the person consumes.

In an example, a person can be prompted to use a hand-held food-identifying sensor for chemical analysis of food when a smart watch detects that the person is consuming food. In an example, a person can be prompted to use a smart utensil for chemical analysis of food when a smart watch detects that the person is consuming food. In an example, a person can be prompted to use a food probe for chemical analysis of food when a smart watch detects that the person is consuming food.

In an example, a person can be prompted to use a hand-held food-identifying sensor to take pictures of food when a smart watch detects that the person is consuming food. In an example, a person can be prompted to use a mobile phone to take pictures of food when a smart watch detects that the person is consuming food. In an example, a person can be prompted to use a smart utensil to take pictures of food when a smart watch detects that the person is consuming food. In an example, a person can be prompted to use a digital camera to take pictures of food when a smart watch detects that the person is consuming food.

In an example, a device and method for monitoring, sensing, detecting, and/or tracking a person's consumption of one or more selected types of foods, ingredients, or nutrients can comprise a wearable device with primary and second modes, mechanisms, or levels of data collection concerning a person's food consumption. The primary mode of data collection can be continuous, not requiring action by the person in association with an eating event apart from the act of eating, and be more useful for general detection of food consumption than it is for identification of consumption of selected types of foods, ingredients, and/or nutrients by the person. The secondary mode of data collection can be non-continuous, requiring action by the person in association with an eating event apart from the act of eating, and can be very useful for identification of consumption of selected types of foods, ingredients, and/or nutrients by the person.

In an example, both primary and secondary data collection can be performed by a device that a person wears on their wrist (such as a smart watch or watch phone). In example, both primary and secondary data collection can be performed by a device that a person wears around their neck (such as a smart necklace or necklace phone). In an example, primary and secondary data can be jointly analyzed to measure the types and amounts of specific foods, ingredients, and/or nutrients that the person consumes. In an example, a person can be prompted to collect secondary data when primary data indicates that the person is probably consuming food.

In an example, data collection by a hand-held food-identifying sensor (such as a smart utensil, food probe, or smart phone) concerning a particular eating event requires action by a person in association with this eating event apart from the actual act of eating. In an example, the person can be prompted to collect data using the hand-held food-identifying sensor when: data that is automatically collected by a wearable food-consumption monitor indicates that the person is probably consuming food; and the person has not already collected data concerning this particular eating event.

In an example, data collection by a hand-held food-identifying sensor can require that a person bring a food-identifying sensor into contact with food, wherein the person is prompted to bring the food-identifying sensor into contact with food when: data that is automatically collected by a wearable food-consumption monitor indicates that the person is probably consuming food; and the person has not already brought the food-identifying sensor into contact with this food. In an example, data collection by a hand-held food-identifying sensor can require that the person aim a camera and take a picture of food, wherein the person is prompted to aim a camera and take a picture of food when: data that is automatically collected by a wearable food-consumption monitor indicates that the person is probably consuming food; and the person has not already taken a picture of this food.

In an example, data collection by a hand-held food-identifying sensor can require that a person enter information concerning food consumed into a hand-held member by touch, keyboard, speech, or gesture. The person can be prompted to enter information concerning food consumed into a hand-held member by touch, keyboard, speech, or gesture when: data that is automatically collected by a wearable food-consumption monitor indicates that the person is probably consuming food; and the person has not already entered information concerning this food.

11. Some Devices and Methods for Measuring Food Consumption

In an example, a device for measuring a person's consumption of at least one selected type of food, ingredient, or nutrient can comprise: a wearable food-consumption monitor that detects when the person is probably consuming food; and a hand-held food-identifying sensor that detects the person's consumption of at least one selected type of food, ingredient, or nutrient. In an example, the person can be prompted to use the hand-held food-identifying sensor when the wearable consumption monitor indicates that the person is consuming food. In an example, the hand-held food-identifying sensor can be automatically activated or triggered when the food-consumption monitor indicates that the person is consuming food.

In an example, a device for measuring, monitoring, sensing, detecting, and/or tracking a person's consumption of at least one selected type of food, ingredient, or nutrient can comprise: a wearable food-consumption monitor that automatically monitors and detects when the person consumes food, wherein operation of this monitor to detect food consumption does not require any action associated with a particular eating event by the person apart from the actual act of eating; and a hand-held food-identifying sensor that identifies the selected types of foods, ingredients, and/or nutrients that the person consumes, wherein operation of this sensor to identify foods, ingredients, and/or nutrients during a particular eating event requires action by the person apart associated with that eating event apart from the actual act of eating, and wherein the person is prompted to use the hand-held food-identifying sensor when the wearable consumption monitor indicates that the person is consuming food.

In an example, a method for measuring a person's consumption of at least one selected type of food, ingredient, or nutrient can comprise: collecting primary data concerning food consumption using a wearable food-consumption monitor to detect when a person is consuming food; and collecting secondary data concerning food consumption using a hand-held food-identifying sensor when analysis of primary data indicates that the person is consuming food. In an example, collection of secondary data can be automatic when primary data indicates that the person is consuming food. In an example, collection of secondary data can require a triggering action by the person in association with a particular eating event apart from the actual act of eating. In an example, the person can be prompted to take the triggering action necessary to collect secondary data when primary data indicates that the person is consuming food.

In an example, a method for measuring, monitoring, sensing, detecting, and/or tracking a person's consumption of at least one selected type of food, ingredient, or nutrient can comprise: collecting primary data using a wearable food-consumption monitor to detect when a person is probably consuming food, wherein this detector is worn on the person, and wherein primary data collection does not require action by the person at the time of food consumption apart from the act of consuming food; and collecting secondary data using a hand-held food-identifying sensor to identify the selected types of foods, ingredients, or nutrients that the person is consuming, wherein secondary data collection by the hand-held food-identifying sensor requires action by the person at the time of food consumption apart from the act of consuming food, and wherein the person is prompted to take this action when primary data indicates that the person is consuming food and secondary data has not already been collected.

In an example, a method for measuring a person's consumption of at least one selected type of food, ingredient, or nutrient can comprise: (a) having the person wear a motion sensor that is configured to be worn on at least one body member selected from the group consisting of wrist, hand, finger, and arm; wherein this motion sensor continually monitors body motion to provide primary data that is used to detect when a person is consuming food; (b) prompting the person to collect secondary data concerning food consumption when this primary data indicates that the person is consuming food; wherein secondary data is selected from the group consisting of: data from the interaction between food and reflected, absorbed, or emitted light energy including pictures, chromatographic results, fluorescence results, absorption spectra, reflection spectra, infrared radiation, and ultraviolet radiation; data from the interaction between food and electromagnetic energy including electrical conductivity, electrical resistance, and magnetic interaction; data from the interaction between food and sonic energy including ultrasonic energy; data from the interaction between food and chemical receptors including reagents, enzymes, biological cells, and microorganisms; and data from the interaction between food and mass measuring devices including scales and inertial sensors; and (c) using both primary and secondary data to identify the types and quantities of food consumed in a manner that is at least a partially-automatic; wherein the identification of food type and quantity includes one or more methods selected from the group consisting of: motion pattern analysis and identification; image pattern analysis and identification; chromatography; electromagnetic energy pattern analysis and identification; sound pattern analysis and identification; mass, weight, and/or density; and chemical composition analysis.

In an example, a device for measuring a person's consumption of at least one selected type of food, ingredient, or nutrient can comprise: a wearable motion sensor that automatically collects data concerning body motion, wherein this body motion data is used to determine when a person is consuming food; and an imaging sensor that collects images of food, wherein these food images are used to identify the type and quantity of food, ingredients, or nutrients that a person is consuming food. In an example, an imaging sensor that requires action by the person to pictures of food during an eating event. In an example, the device can prompt the person to use the imaging sensor to take pictures of food when body motion data indicates that the person is consuming food. In an example, a device for measuring a person's consumption of at least one selected type of food, ingredient, or nutrient can comprise: a wearable motion sensor that is worn by a person, wherein this motion sensor automatically and continuously collects data concerning the person's body motion, and wherein the body motion data is used to determine when a person is consuming food; and a wearable imaging sensor that is worn by the person, wherein this imaging sensor does not continuously take pictures, but rather only collects images of eating activity when body motion data indicates that the person is consuming food.

In an example, an imaging sensor need not collect images continuously, but rather requires specific action by the person to initiate imaging at the time of food consumption apart from the actual action of eating. In an example, a person can be prompted to take pictures of food when body motion data collected by a wearable motion sensor indicates that the person is consuming food. In an example, a person can be prompted to take pictures of food when sound data collected by a wearable sound sensor indicates that the person is consuming food.

In an example, a device for measuring a person's consumption of at least one selected type of food, ingredient, or nutrient can comprise: a wearable motion sensor that automatically collects data concerning body motion, wherein this body motion data is used to determine when a person is consuming food; and a chemical composition sensor that analyzes the chemical composition of food, wherein results of this chemical analysis are used to identify the type and quantity of food, ingredients, or nutrients that a person is consuming food. In an example, a device for measuring a person's consumption of at least one selected type of food, ingredient, or nutrient can comprise: a wearable motion sensor that is worn by a person, wherein this motion sensor automatically and continuously collects data concerning the person's body motion, and wherein the body motion data is used to determine when a person is consuming food; and a chemical composition sensor, wherein this chemical composition sensor does not continuously monitor the chemical composition of material within the person's mouth or gastrointestinal tract, but rather only collects information concerning the chemical composition of material within the person's mouth or gastrointestinal tract when body motion data indicates that the person is consuming food.

In an example, a chemical composition sensor can identify the type of food, ingredient, or nutrient based on: physical contact between the sensor and food; or the effects of interaction between food and electromagnetic energy or light energy. In an example, a chemical composition sensor need not collect chemical information continuously, but rather requires specific action by the person to initiate chemical analysis at the time of food consumption apart from the actual action of consuming food. In an example, a person can be prompted to activate a sensor to perform chemical analysis of food when body motion data collected by a wearable motion sensor indicates that the person is consuming food. In an example, a person can be prompted to activate a sensor to perform chemical analysis of food when sound data collected by a wearable sound sensor indicates that the person is consuming food.

In an example, a device for measuring a person's consumption of at least one selected type of food, ingredient, or nutrient can comprise: a wearable sound sensor that automatically collects data concerning body or environmental sounds, wherein this sound data is used to determine when a person is consuming food; and an imaging sensor that collects images of food, wherein these food images are used to identify the type and quantity of food, ingredients, or nutrients that a person is consuming food. In an example, this imaging sensor can require action by the person to pictures of food during an eating event. In an example, the person can be prompted to use the imaging sensor to take pictures of food when sound data indicates that the person is consuming food. In an example, a device for measuring a person's consumption of at least one selected type of food, ingredient, or nutrient can comprise: a wearable sound sensor that is worn by a person, wherein this sound sensor automatically and continuously collects data concerning sounds from the person's body, and wherein this sound data is used to determine when a person is consuming food; and a wearable imaging sensor that is worn by the person, wherein this imaging sensor does not continuously take pictures, but rather only collects images of eating activity when sound data indicates that the person is consuming food.

In an example, a device for measuring a person's consumption of at least one selected type of food, ingredient, or nutrient can comprise: a wearable sound sensor that automatically collects data concerning body or environmental sound, wherein this sound data is used to determine when a person is consuming food; and a chemical composition sensor that analyzes the chemical composition of food, wherein results of this chemical analysis are used to identify the type and quantity of food, ingredients, or nutrients that a person is consuming food. In an example, a device for measuring a person's consumption of at least one selected type of food, ingredient, or nutrient can comprise: a wearable sound sensor that is worn by a person, wherein this motion sensor automatically and continuously collects data concerning sound from the person's body, and wherein this sound data is used to determine when a person is consuming food; and a chemical composition sensor, wherein this chemical composition sensor does not continuously monitor the chemical composition of material within the person's mouth or gastrointestinal tract, but rather only collects information concerning the chemical composition of material within the person's mouth or gastrointestinal tract when sound data indicates that the person is consuming food.

In an example, a method for measuring a person's consumption of at least one selected type of food, ingredient, or nutrient can comprise: collecting a first set of data to detect when a person is probably consuming food in an automatic and continuous manner that does not require action by the person at the time of food consumption apart from the act of consuming food; collecting a second set of data to identify what selected types of foods, ingredients, or nutrients a person is consuming when the first set of data indicates that the person is probably consuming food; and jointly analyzing both the first and second sets of data to estimate consumption of at least one specific food, ingredient, or nutrient by the person.

In an example, a device or system for measuring a person's consumption of at least one selected type of food, ingredient, or nutrient can comprise: (a) a wearable food-consumption monitor that is configured to be worn on a person's body or clothing, wherein this monitor automatically collects primary data that is used to detect when the person is consuming food; (b) a food-identifying sensor that collects secondary data that is used to measure the person's consumption of at least one selected type of food, ingredient, or nutrient, and wherein secondary data collection in association with a specific food consumption event requires a specific action by the person in association with that specific food consumption event apart from the act of consuming food; and (c) a computer-to-human prompting interface, wherein this interface prompts the person to take the specific action required for secondary data collection in association with a specific food consumption event when the primary data indicates that the person is consuming food and the person has not already taken this specific action. In an example, primary data can be body movement data or data concerning electromagnetic signals from the person's body. In an example, secondary data can be collected by a mobile phone, smart utensil, food probe, smart necklace, smart eyewear, or a smart watch.

In an example, a device or system for measuring a person's consumption of at least one selected type of food, ingredient, or nutrient can comprise: (a) a wearable food-consumption monitor that is configured to be worn on a person's body or clothing, wherein this monitor automatically collects primary data that is used to detect when the person is consuming food; (b) an imaging component that collects secondary data that is used to measure the person's consumption of at least one selected type of food, ingredient, or nutrient, wherein this secondary data comprises pictures of food, and wherein taking pictures of food in association with a specific food consumption event requires a specific action by the person in association with that specific food consumption event apart from the act of consuming food; and (c) a computer-to-human prompting interface, wherein this interface prompts the person to take pictures of food in association with a specific food consumption event when the primary data indicates that the person is consuming food and pictures of this food have not already been taken. In an example, primary data can be body movement data or data concerning electromagnetic signals from the person's body. In an example, secondary data can be collected by a mobile phone, smart utensil, food probe, smart necklace, smart eyewear, or a smart watch.

In an example, a device or system for measuring a person's consumption of at least one selected type of food, ingredient, or nutrient can comprise: (a) a wearable food-consumption monitor that is configured to be worn on a person's body or clothing, wherein this monitor automatically collects primary data that is used to detect when the person is consuming food; (b) an chemical-analyzing component that collects secondary data that is used to measure the person's consumption of at least one selected type of food, ingredient, or nutrient, wherein this secondary data comprises chemical analysis of food, and wherein performing chemical analysis of food in association with a specific food consumption event requires a specific action by the person in association with that specific food consumption event apart from the act of consuming food; and (c) a computer-to-human prompting interface, wherein this interface prompts the person to take the action required to perform chemical analysis of food in association with a specific food consumption event when the primary data indicates that the person is consuming food and chemical analysis of this food has not already been performed. In an example, primary data can be body movement data or data concerning electromagnetic signals from the person's body. In an example, secondary data can be collected by a mobile phone, smart utensil, food probe, smart necklace, smart eyewear, or a smart watch.

In an example, a device or system for measuring a person's consumption of at least one selected type of food, ingredient, or nutrient can comprise: (a) a wearable food-consumption monitor that is configured to be worn on a person's body or clothing, wherein this monitor automatically collects primary data that is used to detect when the person is consuming food; (b) a computer-to-human prompting interface which a person uses to enter secondary data concerning the person's consumption of at least one selected type of food, ingredient, or nutrient, wherein this interface selected from the group consisting of: speech or voice recognition, touch or gesture recognition, motion recognition or eye tracking, and buttons or keys, and wherein this interface prompts the person to enter secondary data in association with a specific food consumption event when the primary data indicates that the person is consuming food and the person has not already entered this data. In an example, primary data can be body movement data or data concerning electromagnetic signals from the person's body. In an example, secondary data can be collected by a mobile phone, smart utensil, food probe, smart necklace, smart eyewear, or a smart watch.

In an example, a device or system for measuring a person's consumption of at least one selected type of food, ingredient, or nutrient can comprise: (a) a wearable food-consumption monitor that is configured to be worn on a person's body or clothing, wherein this monitor automatically collects primary data that is used to detect when the person is consuming food; (b) a food-identifying sensor that automatically collects secondary data that is used to measure the person's consumption of at least one selected type of food, ingredient, or nutrient in association with a specific food consumption event when the primary data indicates that the person is consuming food. In an example, primary data can be body movement data or data concerning electromagnetic signals from the person's body. In an example, secondary data can be collected by a mobile phone, smart utensil, food probe, smart necklace, smart eyewear, or a smart watch.

In an example, a device or system for measuring a person's consumption of at least one selected type of food, ingredient, or nutrient can comprise: (a) a smart watch that is configured to be worn on a person's wrist, hand, or arm, wherein this smart watch automatically collects primary data that is used to detect when the person is consuming food; (b) a food-identifying sensor that collects secondary data that is used to measure the person's consumption of at least one selected type of food, ingredient, or nutrient, and wherein secondary data collection in association with a specific food consumption event requires a specific action by the person in association with that specific food consumption event apart from the act of consuming food; and (c) a computer-to-human prompting interface, wherein this interface prompts the person to take the specific action required for secondary data collection in association with a specific food consumption event when the primary data indicates that the person is consuming food and the person has not already taken this specific action. In an example, primary data can be body movement data or data concerning electromagnetic signals from the person's body. In an example, secondary data can be collected by a mobile phone, smart utensil, food probe, smart necklace, smart eyewear, or the smart watch.

In an example, a device or system for measuring a person's consumption of at least one selected type of food, ingredient, or nutrient can comprise: (a) a smart watch that is configured to be worn on a person's wrist, hand, or arm, wherein this smart watch automatically collects primary data that is used to detect when the person is consuming food; (b) an imaging component that collects secondary data that is used to measure the person's consumption of at least one selected type of food, ingredient, or nutrient, wherein this secondary data comprises pictures of food, and wherein taking pictures of food in association with a specific food consumption event requires a specific action by the person in association with that specific food consumption event apart from the act of consuming food; and (c) a computer-to-human prompting interface, wherein this interface prompts the person to take pictures of food in association with a specific food consumption event when the primary data indicates that the person is consuming food and pictures of this food have not already been taken. In an example, primary data can be body movement data or data concerning electromagnetic signals from the person's body. In an example, secondary data can be collected by a mobile phone, smart utensil, food probe, smart necklace, smart eyewear, or the smart watch.

In an example, a device or system for measuring a person's consumption of at least one selected type of food, ingredient, or nutrient can comprise: (a) a smart watch that is configured to be worn on a person's wrist, hand, or arm, wherein this smart watch automatically collects primary data that is used to detect when the person is consuming food; (b) an chemical-analyzing component that collects secondary data that is used to measure the person's consumption of at least one selected type of food, ingredient, or nutrient, wherein this secondary data comprises chemical analysis of food, and wherein performing chemical analysis of food in association with a specific food consumption event requires a specific action by the person in association with that specific food consumption event apart from the act of consuming food; and (c) a computer-to-human prompting interface, wherein this interface prompts the person to take the action required to perform chemical analysis of food in association with a specific food consumption event when the primary data indicates that the person is consuming food and chemical analysis of this food has not already been performed. In an example, primary data can be body movement data or data concerning electromagnetic signals from the person's body. In an example, secondary data can be collected by a mobile phone, smart utensil, food probe, smart necklace, smart eyewear, or the smart watch.

In an example, a device or system for measuring a person's consumption of at least one selected type of food, ingredient, or nutrient can comprise: (a) a smart watch that is configured to be worn on a person's wrist, hand, or arm, wherein this smart watch automatically collects primary data that is used to detect when the person is consuming food; (b) a computer-to-human prompting interface which a person uses to enter secondary data concerning the person's consumption of at least one selected type of food, ingredient, or nutrient, wherein this interface selected from the group consisting of: speech or voice recognition, touch or gesture recognition, motion recognition or eye tracking, and buttons or keys, and wherein this interface prompts the person to enter secondary data in association with a specific food consumption event when the primary data indicates that the person is consuming food and the person has not already entered this data. In an example, primary data can be body movement data or data concerning electromagnetic signals from the person's body. In an example, the interface can comprise a mobile phone, smart utensil, food probe, smart necklace, smart eyewear, or the smart watch.

In an example, a device or system for measuring a person's consumption of at least one selected type of food, ingredient, or nutrient can comprise: (a) a smart watch that is configured to be worn on a person's wrist, hand, or arm, wherein this smart watch automatically collects primary data that is used to detect when the person is consuming food; (b) a food-identifying sensor that automatically collects secondary data that is used to measure the person's consumption of at least one selected type of food, ingredient, or nutrient in association with a specific food consumption event when the primary data indicates that the person is consuming food. In an example, primary data can be body movement data or data concerning electromagnetic signals from the person's body. In an example, secondary data can be collected by a mobile phone, smart utensil, food probe, smart necklace, smart eyewear, or the smart watch.

12. Narrative to Accompany FIGS. 1 Through 4

First we will provide an introductory overview to FIGS. 1 through 4. FIGS. 1 through 4 show an example of how this invention can be embodied in a device and system for measuring a person's consumption of at least one specific type of food, ingredient, or nutrient, wherein this device and system has two components. The first component is a wearable food-consumption monitor that is worn on a person's body or clothing. In this example, the wearable food-consumption monitor is a smart watch that is worn on a person's wrist. The smart watch automatically collects primary data that is used to detect when a person is consuming food. The second component is a hand-held food-identifying sensor. In this example, the hand-held food-identifying sensor is a smart spoon. The smart spoon collects secondary data that is used to identify the person's consumption of at least one specific type of food, ingredient, or nutrient.

In the example shown in FIGS. 1 through 4, the smart watch collects primary data automatically, without requiring any specific action by the person in association with a specific eating event apart from the actual act of eating. As long as the person continues to wear the smart watch, the smart watch collects the primary data that is used to detect food consumption. In an example, primary data can be motion data concerning the person's wrist movements. In an example, primary data can be up-and-down and tilting movements of the wrist that are generally associated with eating food. In contrast to primary data collection by the smart watch, which is automatic and relatively-continuous, secondary data collection by the smart spoon depends on the person using that particular spoon to eat. In other words, secondary data collection by the smart spoon requires specific action by the person in association with a specific eating event apart from the actual act of eating.

This device and system includes both a smart watch and a smart spoon that work together as an integrated system. Having the smart watch and smart spoon work together provides advantages over use of either a smart watch or a smart spoon by itself. The smart watch provides superior capability for food consumption monitoring (as compared to a smart spoon) because the person wears the smart watch all the time and the smart watch monitors for food consumption continually. The smart spoon provides superior capability for food identification (as compared to a smart watch) because the spoon has direct contact with the food and can directly analyze the chemical composition of food in a manner that is difficult to do with a wrist-worn member. Having both the smart watch and smart spoon work together as an integrated system can provide better monitoring compliance and more-accurate food identification than either working alone.

As FIGS. 1 through 4 collectively show, an integrated device and system that comprises both a smart watch and a smart spoon, working together, can measure a person's consumption of at least one selected type of food, ingredient, or nutrient in a more consistent and accurate manner than either a smart watch or a smart spoon operating alone. One way in which the smart watch and smart spoon can work together is for the smart watch to track whether or not the smart spoon is being used when the smart watch detects that the person is eating food. If the smart spoon is not being used when the person eats, then the smart watch can prompt the person to use the smart spoon. This prompt can range from a relatively-innocuous tone or vibration (which the person can easily ignore) to a more-substantive aversive stimulus, depending on the strength of the person's desire for measurement accuracy and self-control.

Having provided an introductory overview for FIGS. 1 through 4 collectively, we now discuss them individually. FIG. 1 introduces the hand-held food-identifying sensor of this device, which is a smart spoon in this example. In this example, a smart spoon is a specialized electronic spoon that includes food sensors as well as wireless data communication capability. In this example, the smart spoon includes a chemical sensor which analyzes the chemical composition of food with which the spoon comes into contact. FIG. 2 introduces the wearable food-consumption monitor of this device, which is a smart watch in this example. In this example, a smart watch is a wrist-worn electronic device that includes body sensors, a data processing unit, and wireless data communication capability. In this example, the body sensor is a motion sensor. FIGS. 3 and 4 show how the smart spoon and smart watch work together as an integrated system to monitor and measure a person's consumption of at least one selected type of food, ingredient, or nutrient. We now discuss FIGS. 1 through 4 individually in more detail.

FIG. 1 shows that the hand-held food-identifying sensor in this device is a smart spoon 101 that comprises at least four operational components: a chemical composition sensor 102; a data processing unit 103; a communication unit 104; and a power supply and/or transducer 105. In other examples, the hand-held food-identifying sensor component of this device can be a different kind of smart utensil, such as a smart fork, or can be a hand-held food probe. In an example, smart spoon 101 can include other components, such as a motion sensor or camera. The four operational components 102-105 of smart spoon 101 in this example are in electronic communication with each other. In an example, this electronic communication can be wireless. In another example, this electronic communication can be through wires. Connecting electronic components with wires is well-known in the prior art and the precise configuration of possible wires is not central to this invention, so connecting wires are not shown.

In an example, power supply and/or transducer 105 can be selected from the group consisting of: power from a power source that is internal to the device during regular operation (such as an internal battery, capacitor, energy-storing microchip, or wound coil or spring); power that is obtained, harvested, or transduced from a power source other than the person's body that is external to the device (such as a rechargeable battery, electromagnetic inductance from external source, solar energy, indoor lighting energy, wired connection to an external power source, ambient or localized radiofrequency energy, or ambient thermal energy); and power that is obtained, harvested, or transduced from the person's body (such as kinetic or mechanical energy from body motion.

In the example shown in FIG. 1, chemical composition sensor 102 on the food-carrying scoop end of smart spoon 101 can identify at least one selected type of food, ingredient, or nutrient by analyzing the chemical composition of food that is carried by smart spoon 101. In this example, chemical composition sensor 102 analyzes the chemical composition of food by being in direct fluid communication with food that is carried in the scoop end of smart spoon 101. In this example, chemical composition sensor 102 includes at least one chemical receptor to which chemicals in a selected type of food, ingredient, or nutrient bind. This binding action creates a signal that is detected by the chemical composition sensor 102, received by the data processing unit 103, and then transmitted to a smart watch or other location via communication unit 104.

In another example, chemical composition sensor 102 can analyze the chemical composition of food by measuring the effects of the interaction between food and light energy. In an example, this interaction can comprise the degree of reflection or absorption of light by food at different light wavelengths. In an example, this interaction can include spectroscopic analysis.

In an example, chemical composition sensor 102 can directly identify at least one selected type of food by chemical analysis of food contacted by the spoon. In an example, chemical composition sensor 102 can directly identify at least one selected type of ingredient or nutrient by chemical analysis of food. In an example, at least one selected type of ingredient or nutrient can be identified indirectly by: first identifying a type and amount of food; and then linking that identified food to common types and amounts of ingredients or nutrients, using a database that links specific foods to specific ingredients or nutrients. In various examples, such a food database can be located in the data processing unit 103 of smart spoon 101, in the data processing unit 204 of a smart watch 201, or in an external device with which smart spoon 101 and/or a smart watch 201 are in wireless communication.

In various examples, a selected type of food, ingredient, or nutrient that is identified by chemical composition sensor 102 can be selected from the group consisting of: a specific type of carbohydrate, a class of carbohydrates, or all carbohydrates; a specific type of sugar, a class of sugars, or all sugars; a specific type of fat, a class of fats, or all fats; a specific type of cholesterol, a class of cholesterols, or all cholesterols; a specific type of protein, a class of proteins, or all proteins; a specific type of fiber, a class of fiber, or all fiber; a specific sodium compound, a class of sodium compounds, and all sodium compounds; high-carbohydrate food, high-sugar food, high-fat food, fried food, high-cholesterol food, high-protein food, high-fiber food, and high-sodium food.

In various examples, chemical composition sensor 102 can analyze food composition to identify one or more potential food allergens, toxins, or other substances selected from the group consisting of: ground nuts, tree nuts, dairy products, shell fish, eggs, gluten, pesticides, animal hormones, and antibiotics. In an example, a device can analyze food composition to identify one or more types of food (such as pork) whose consumption is prohibited or discouraged for religious, moral, and/or cultural reasons.

In various examples, chemical composition sensor 102 can be selected from the group of sensors consisting of: receptor-based sensor, enzyme-based sensor, reagent based sensor, antibody-based receptor, biochemical sensor, membrane sensor, pH level sensor, osmolality sensor, nucleic acid-based sensor, or DNA/RNA-based sensor; biomimetic sensor (such as an artificial taste bud or an artificial olfactory sensor), chemiresistor, chemoreceptor sensor, electrochemical sensor, electroosmotic sensor, electrophoresis sensor, or electroporation sensor; specific nutrient sensor (such as a glucose sensor, a cholesterol sensor, a fat sensor, a protein-based sensor, or an amino acid sensor); color sensor, colorimetric sensor, photochemical sensor, chemiluminescence sensor, fluorescence sensor, chromatography sensor (such as an analytical chromatography sensor, a liquid chromatography sensor, or a gas chromatography sensor), spectrometry sensor (such as a mass spectrometry sensor), spectrophotometer sensor, spectral analysis sensor, or spectroscopy sensor (such as a near-infrared spectroscopy sensor); and laboratory-on-a-chip or microcantilever sensor.

In an example, smart spoon 101 can measure the quantities of foods, ingredients, or nutrients consumed as well as the specific types of foods, ingredients, or nutrients consumed. In an example, smart spoon 101 can include a scale which tracks the individual weights (and cumulative weight) of mouthfuls of food carried and/or consumed during an eating event. In an example, smart spoon 101 can approximate the weights of mouthfuls of food carried by the spoon by measuring the effect of those mouthfuls on the motion of the spoon as a whole or the relative motion of one part of the spoon relative to another. In an example, smart spoon 101 can include a motion sensor and/or inertial sensor. In an example, smart spoon 101 can include one or more accelerometers in different, motion-variable locations along the length of the spoon. In an example, smart spoon 101 can include a spring and/or strain gauge between the food-carrying scoop of the spoon and the handle of the spoon. In an example, food weight can estimated by measuring distension of the spring and/or strain gauge as food is brought up to a person's mouth.

In an example, smart spoon 101 can use a motion sensor or an inertial sensor to estimate the weight of the food-carrying scoop of the spoon at a first point in time (such as during an upswing motion as the spoon carries a mouthful of food up to the person's mouth) and also at a second point in time (such as during a downswing motion as the person lowers the spoon from their mouth). In an example, smart spoon 101 can estimate the weight of food actually consumed by calculating the difference in food weights between the first and second points in time. In an example, a device can track cumulative food consumption by tracking the cumulative weights of multiple mouthfuls of (different types of) food during an eating event or during a defined period of time (such as a day or week).

FIG. 2 shows that, in this embodiment of the invention, the wearable food-consumption monitor component of the device is a smart watch 201. Smart watch 201 is configured to be worn around the person's wrist, adjoining the person's hand 206. In other examples, the wearable food-consumption monitor component of this device can be embodied in a smart bracelet, smart arm band, or smart finger ring. In this example, smart watch 201 includes four operational components: a communication unit 202; a motion sensor 203; a data processing unit 204; and a power supply and/or transducer 205. In other examples, a wearable food-consumption monitor component of this device can be embodied in a smart necklace. In the case of a smart necklace, monitoring for food consumption would more likely be done with a sound sensor rather than a motion sensor. In the case of a smart necklace, food consumption can be monitored and detected by detecting swallowing and/or chewing sounds, rather than monitoring and detecting hand-to-mouth motions.

The four components 202-205 of smart watch 201 are in electronic communication with each other. In an example, this electronic communication can be wireless. In another example, this electronic communication can be through wires. Connecting electronic components with wires is well-known in the prior art and the precise configuration of possible wires is not central to this invention, so a configuration of connecting wires is not shown.

In an example, power supply and/or transducer 205 can be selected from the group consisting of: power from a power source that is internal to the device during regular operation (such as an internal battery, capacitor, energy-storing microchip, or wound coil or spring); power that is obtained, harvested, or transduced from a power source other than the person's body that is external to the device (such as a rechargeable battery, electromagnetic inductance from external source, solar energy, indoor lighting energy, wired connection to an external power source, ambient or localized radiofrequency energy, or ambient thermal energy); and power that is obtained, harvested, or transduced from the person's body (such as kinetic or mechanical energy from body motion.

In an example, motion sensor 203 of smart watch 201 can be selected from the group consisting of: bubble accelerometer, dual-axial accelerometer, electrogoniometer, gyroscope, inclinometer, inertial sensor, multi-axis accelerometer, piezoelectric sensor, piezo-mechanical sensor, pressure sensor, proximity detector, single-axis accelerometer, strain gauge, stretch sensor, and tri-axial accelerometer. In an example, motion sensor 203 can collect primary data concerning movements of a person's wrist, hand, or arm.

In an example, there can be an identifiable pattern of movement that is highly-associated with food consumption. Motion sensor 203 can continuously monitor a person's wrist movements to identify times when this pattern occurs to detect when the person is probably eating. In an example, this movement can include repeated movement of the person's hand 206 up to their mouth. In an example, this movement can include a combination of three-dimensional roll, pitch, and yaw by a person's wrist. In an example, motion sensor 203 can also be used to estimate the quantity of food consumed based on the number of motion cycles. In an example, motion sensor 203 can be also used to estimate the speed of food consumption based on the speed or frequency of motion cycles.

In various examples, movements of a person's body that can be monitored and analyzed can be selected from the group consisting of: hand movements, wrist movements, arm movements, tilting movements, lifting movements, hand-to-mouth movements, angles of rotation in three dimensions around the center of mass known as roll, pitch and yaw, and Fourier Transformation analysis of repeated body member movements.

In various examples, smart watch 201 can include a sensor to monitor for possible food consumption other than a motion sensor. In various examples, smart watch 201 can monitor for possible food consumption using one or more sensors selected from the group consisting of: electrogoniometer or strain gauge; optical sensor, miniature still picture camera, miniature video camera, miniature spectroscopy sensor; sound sensor, miniature microphone, speech recognition software, pulse sensor, ultrasound sensor; electromagnetic sensor, skin galvanic response (Galvanic Skin Response) sensor, EMG sensor, chewing sensor, swallowing sensor; and temperature sensor, thermometer, or infrared sensor.

In addition to smart watch 201 that is worn around the person's wrist, FIG. 2 also shows that the person's hand 206 holding a regular spoon 207 that is carrying a mouthful of food 208. It is important to note that this is a regular spoon 207 (with no sensor or data transmission capability), not the smart spoon 101 that was introduced in FIG. 1. There are multiple possible reasons for use of a regular spoon 207 rather than smart spoon 101. In various examples, the person may simply have forgotten to use the smart spoon, may be intentionally trying to "cheat" on dietary monitoring by not using the smart spoon, or may be in dining setting where they are embarrassed to use the smart spoon.

In any event, if the person continues to use the regular spoon 207 instead of the smart spoon 101, then the device and system will not be able to accurately identify the amounts and types of food that they are eating. If the person were not wearing smart watch 201, then the person could continue eating with regular spoon 207 and the device would be completely blind to the eating event. This would lead to low accuracy and low consistency in measuring food consumption. This highlights the accuracy, consistency, and compliance problems that occur if a device relies only on a hand-held food-identifying sensor (without integration with a wearable food-consumption monitor). FIGS. 3 and 4 show how the embodiment disclosed here, comprising both a wearable food-consumption monitor (smart watch 201) and a hand-held food-identification sensor (smart spoon 101) that work together, can correct these problems.

In FIG. 3, motion sensor 203 of smart watch 201 detects the distinctive pattern of wrist and/or arm movement (represented symbolically by the rotational dotted line arrow around hand 206) that indicates that the person is probably consuming food. In an example, a three-dimensional accelerometer on smart watch 201 can detect a distinctive pattern of upward (hand-up-to-mouth) arm movement, followed by a distinctive pattern of tilting or rolling motion (food-into-mouth) wrist movement, followed by a distinctive pattern of downward (hand-down-from-mouth) movement.

If smart watch 201 detects a distinctive pattern of body movements that indicates that the person is probably eating and smart watch 201 has not yet received food identifying secondary data from the use of smart spoon 101, then smart watch 201 can prompt the person to start using smart spoon 101. In an example, this prompt can be relatively-innocuous and easy for the person to ignore if they wish to ignore it. In an example, this prompt can be a quiet tone, gentle vibration, or modest text message to a mobile phone. In another example, this prompt can be a relatively strong and aversive negative stimulus. In an example, this prompt can be a loud sound, graphic warning, mild electric shock, and/or financial penalty.

In the example shown in FIG. 3, the person is not using smart spoon 101 (as they should). This is detected by smart watch 201, which prompts the person to start using smart spoon 101. In FIG. 3, this prompt 301 is represented by a "lightning bolt symbol". In this example, the prompt 301 represented by the lightning bolt symbol is a mild vibration. In an example, a prompt 301 can be more substantive and/or adverse. In an example, the prompt 301 can involve a wireless signal that to a mobile phone or other intermediary device. In an example, the prompt to the person be communicated through an intermediary device and result in an automated text message or phone call (through a mobile phone, for example) to the person to prompt them to use the smart spoon.

In an example, communication unit 202 of smart watch 201 comprises a computer-to-human interface. In an example, part of this computer-to-human interface 202 can include having the computer prompt the person to collect secondary data concerning food consumption when primary data indicates that the person is probably consuming food. In various examples, communication unit 202 can use visual, auditory, tactile, electromagnetic, gustatory, and/or olfactory signals to prompt the person to use the hand-held food-identifying sensor (smart spoon 101 in this example) to collect secondary data (food chemical composition data in this example) when primary data (motion data in this example) collected by the smart watch indicates that the person is probably eating and the person has not already collected secondary data in association with a specific eating event.

In this example, the person's response to the prompt 301 from smart watch 201 is entirely voluntary; the person can ignore the prompt and continue eating with a regular spoon 207 if they wish. However, if the person wishes to have a stronger mechanism for self-control and measurement compliance, then the person can select (or adjust) a device to make the prompt stronger and less voluntary. In an example, a stronger prompt can be a graphic display showing the likely impact of excessive food consumption, a mild electric shock, an automatic message to a health care provider, and an automatic message to a supportive friend or accountability partner. In an example, the prompt can comprise playing the latest inane viral video song that is sweeping the internet—which the person finds so annoying that they comply and switch from using regular spoon 207 to using smart spoon 101. The strength of the prompt can depend on how strongly the person feels about self-constraint and self-control in the context of monitoring and modifying their patterns of food consumption.

In an example, even if a person's response to prompt 301 is entirely voluntary and the person ignores prompt 301 to use the smart spoon to collect detailed secondary data concerning the meal or snack that the person is eating, the device can still be aware that a meal or snack has occurred. In this respect, even if the person's response to prompt 301 is voluntary, the overall device and system disclosed herein can still track all eating events. This disclosed device provides greater compliance and measurement information than is likely with a hand-held device only. With a hand-held device only, if the person does not use the hand-held member for a particular eating event, then the device is completely oblivious to that eating event. For example, if a device relies on taking pictures from a smart phone to measure food consumption and a person just keeps the phone in their pocket or purse when they eat a snack or meal, then the device is oblivious to that snack or meal. The device disclosed herein corrects this problem. Even if the person does not respond to the prompt, the device still knows that an eating event has occurred.

In an example, there are other ways by which smart watch 201 can detect if smart spoon 101 is being properly used or not. In an example, both smart watch 201 and smart spoon 101 can have integrated motion sensors (such as paired accelerometers) and their relative motions can be compared. If the movements of smart watch 201 and smart spoon 101 are similar during a time when smart watch 201 detects that the person is probably consuming food, then smart spoon 101 is probably being properly used to consume food. However, if smart spoon is not moving when smart watch 201 detects food consumption, then smart spoon 101 is probably just lying somewhere unused and smart watch 201 can prompt the person to use smart spoon 101.

In a similar manner, there can be a wireless (or non-wireless physical linkage) means of detecting physical proximity between smart watch 201 and smart spoon 101. When the person is eating and the smart spoon 101 is not close to smart watch 201, then smart watch 201 can prompt the person to use smart spoon 101. In an example, physical proximity between smart watch 201 and smart spoon 101 can be detected by electromagnetic signals. In an example, physical proximity between smart watch 201 and smart spoon 101 can be detected by optical signals.

If a person feels very strongly about the need for self-constraint and self-control in the measurement and modification of their food consumption, then a device for measuring consumption of at least one selected type of food, ingredient, or nutrient can be made tamper-resistant. In the example shown in FIGS. 1 through 4, smart watch 201 can include a mechanism for detecting when it is removed from the person's body. This can help make it tamper-resistant. In an example, smart watch 201 can monitor signals related to the person's body selected from the group consisting of: pulse, motion, heat, electromagnetic signals, and proximity to an implanted device. In an example, smart watch 201 can detect when it is been removed from the person's wrist by detecting a lack of motion, lack of a pulse, and/or lack of electromagnetic response from skin. In various examples, smart watch 201 can continually monitor optical, electromagnetic, temperature, pressure, or motion signals that indicate that smart watch 201 is properly worn by a person. In an example, smart watch 201 can trigger feedback if it is removed from the person.

In the final figure of this sequence, FIG. 4 shows that the person has responded positively to prompting signal 301 and has switched from using regular spoon 207 (without food sensing and identification capability) to using smart spoon 101 (with food sensing and identification capability). In FIG. 4, the mouthful of food 208 that is being carried by smart spoon 101 is now in fluid or optical communication with chemical composition sensor 102. This enables identification of at least one selected type of food, ingredient, or nutrient by chemical composition sensor 102 as part of smart spoon 101.

In an example, secondary data concerning the type of food, ingredient, or nutrient carried by smart spoon 101 can be wirelessly transmitted from communication unit 104 on smart spoon 101 to communication unit 202 on smart watch 201. In an example, the data processing unit 204 on smart watch 201 can track the cumulative amount consumed of at least one selected type of food, ingredient, or nutrient. In an example, smart watch 201 can convey this data to an external device, such as through the internet, for cumulative tracking and analysis.

In some respects there can be a tradeoff between the accuracy and consistency of food consumption measurement and a person's privacy. The device disclosed herein offers good accuracy and consistency of food consumption measurement, with relatively-low privacy intrusion. In contrast, consider a first method of measuring food consumption that is based only on voluntary use of a hand-held smart phone or smart utensil, apart from any wearable food consumption monitor. This first method can offer relatively-low privacy intrusion, but the accuracy and consistency of measurement depends completely on the person's remembering to use it each time that the person eats a meal or snack—which can be problematic. Alternatively, consider a second method of measuring food consumption that is based only on a wearable device that continually records video pictures of views (or continually records sounds) around the person. This second method can offer relatively high accuracy and consistency of food consumption measurement, but can be highly intrusive with respect to the person's privacy.

The device disclosed herein provides a good solution to this problem of accuracy vs. privacy and is superior to either the first or second methods discussed above. This embodiment of this device that is shown in FIGS. 1 through 4 comprises a motion-sensing smart watch 201 and a chemical-detecting smart spoon 101 that work together to offer relatively-high food measurement accuracy with relatively-low privacy intrusion. Consistent use of the smart watch 201 does not require that a person remember to carry, pack, or otherwise bring a particular piece of portable electronic equipment like methods that rely exclusively on use of mobile phone or utensil. As long as the person does not remove the smart watch, the smart watch goes with them where ever they go and continually monitors for possible food consumption activity. Also, continually monitoring wrist motion is far less-intrusive with respect to a person's privacy than continually monitoring what the person sees (video monitoring) or hears (sound monitoring).

In this example, a smart watch 201 collects primary data concerning probable food consumption and prompts the person to collect secondary for food identification when primary data indicates that the person is probably eating food and the person has not yet collected secondary data. In this example, primary data is body motion data and secondary data comprises chemical analysis of food. In this example, smart watch 201 is the mechanism for collection of primary data and smart spoon 101 is the mechanism for collection of secondary data. In this example, collection of primary data is automatic, not requiring any action by the person in association with a particular eating event apart from the actual act of eating, but collection of secondary data requires a specific action (using the smart spoon to carry food) in association with a particular eating event apart from the actual act of eating. In this example, this combination of automatic primary data collection and non-automatic secondary data collection combine to provide relatively high-accuracy and high-compliance food consumption measurement with relatively low privacy intrusion. This is an advantage over food consumption devices and methods in the prior art.

In an example, information concerning a person's consumption of at least one selected type of food, ingredient, and/or nutrient can be combined with information from a separate caloric expenditure monitoring device that measures a person's caloric expenditure to comprise an overall system for energy balance, fitness, weight management, and health improvement. In an example, a food-consumption monitoring device (such as this smart watch) can be in wireless communication with a separate fitness monitoring device. In an example, capability for monitoring food consumption can be combined with capability for monitoring caloric expenditure within a single smart watch device. In an example, a smart watch device can be used to measure the types and amounts of food, ingredients, and/or nutrients that a person consumes as well as the types and durations of the calorie-expending activities in which the person engages.

13. Narrative to Accompany FIGS. 5 Through 8

The embodiment of this invention that is shown in FIGS. 5 through 8 is similar to the one that was just shown in FIGS. 1 through 4, except that now food is identified by taking pictures of food rather than by chemical analysis of food. In FIGS. 5 through 8, smart spoon 501 of this device and system has a built-in camera 502. In an example, camera 502 can be used to take pictures of a mouthful of food 208 in the scoop portion of smart spoon 501. In another example, camera 502 can be used to take pictures of food before it is apportioned by the spoon, such as when food is still on a plate, in a bowl, or in original packaging. In an example, the types and amounts of food consumed can be identified, in a manner that is at least partially automated, by analysis of food pictures.

Like the example that was just shown in FIGS. 1 through 4, the example that is now shown in FIGS. 5 through 8 shows how this invention can be embodied in a device and system for measuring a person's consumption that includes both a wearable food-consumption monitor (a smart watch in this example) and a hand-held food-identifying sensor (a smart spoon in this example). However, in this present example, instead of smart spoon 101 having a chemical composition sensor 102 that analyzes the chemical composition of food, smart spoon 501 has a camera 502 to take plain-light pictures of food. These pictures are then analyzed, in a manner that is at least partially automated, in order to identify the amounts and types of foods, ingredients, and/or nutrients that the person consumes. In an example, these pictures of food can be still-frame pictures. In an example, these pictures can be motion (video) pictures.

We now discuss the components of the example shown in FIGS. 5 through 8 in more detail. In FIG. 5, smart spoon 501 includes camera 502 in addition to a data processing unit 503, a communication unit 504, and a power supply and/or transducer 50. The latter three components are like those in the prior example, but the food-identifying sensor (camera 502 vs. chemical composition sensor 102) is different. In this example, camera 502 is built into smart spoon 501 and is located on the portion of smart spoon 501 between the spoon's scoop and the portion of the handle that is held by the person's hand 206.

In this example, camera 502 can be focuses in different directions as the person moves smart spoon 501. In an example, camera 502 can take a picture of a mouthful of food 208 in the scoop of spoon 501. In an example, camera 502 can be directed to take a picture of food on a plate, in a bowl, or in packaging. In this example, camera 502 is activated by touch. In an example, camera 502 can be activated by voice command or by motion of smart spoon 501.

Figure 6:
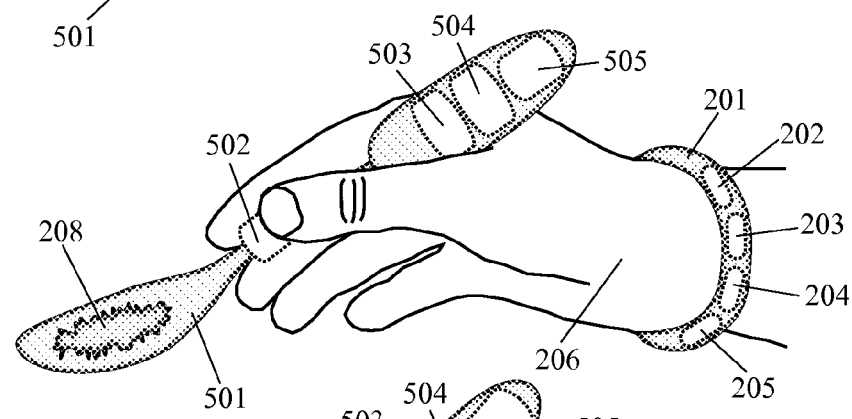
Figure 7:
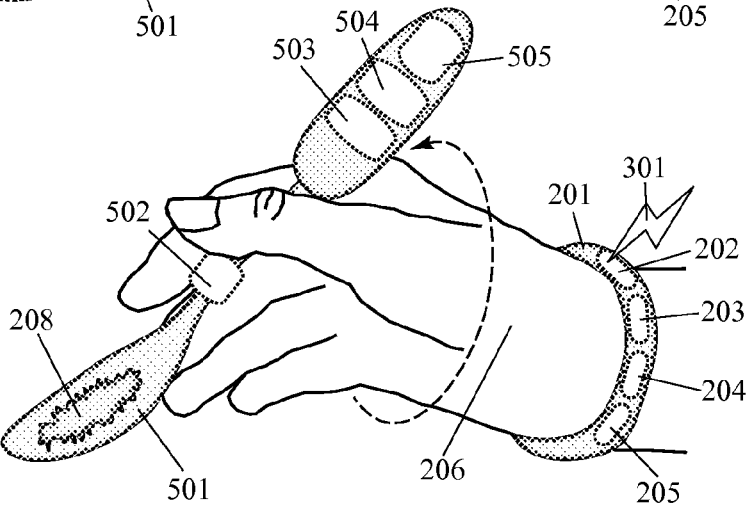
Figure 8:
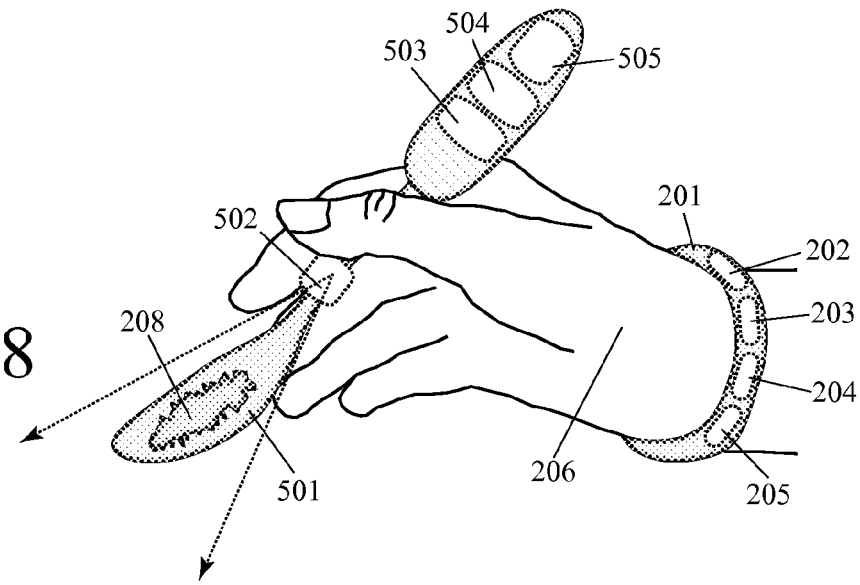

FIG. 6 shows smart spoon 501 in use for food consumption, along with smart watch 201. Smart watch 201 in this example is like smart watch 201 shown in the previous example in FIGS. 1 through 4. As in the last example, smart watch 201 in FIG. 6 includes communication unit 202, motion sensor 203, data processing unit 204, and power supply and/or transducer 205. As in the last example, when the person starts moving their wrist and arm in the distinctive movements that are associated with food consumption, then these movements are recognized by motion sensor 203 on smart watch 201. This is shown in FIG. 7.

If the person has not already used camera 502 on smart spoon 501 to take pictures of food during a particular eating event detected by smart watch 201, then smart watch 201 prompts the person to take a picture of food using camera 502 on smart spoon 501. In this example, this prompt 301 is represented by a "lightning bolt" symbol in FIG. 7. In this example, the person complies with prompt 301 and activates camera 502 by touch in FIG. 8. In this example, a picture is taken of a mouthful of food 208 in the scoop of smart spoon 501. In another example, the person could aim camera 502 on smart spoon 501 toward food on a plate, food in a bowl, or food packaging to take a picture of food before it is apportioned by spoon 501.

In this example, smart watch 201 collects primary data concerning probable food consumption and prompts the person to collect secondary for food identification when primary data indicates that the person is probably eating food and the person has not yet collected secondary data. In this example, primary data is body motion data and secondary data comprises pictures of food. In this example, smart watch 201 is the mechanism for collecting primary data and smart spoon 101 is the mechanism for collecting secondary data. In this example, collection of primary data is automatic, not requiring any action by the person in association with a particular eating event apart from the actual act of eating, but collection of secondary data requires a specific action (triggering and possibly aiming the camera) in association with a particular eating event apart from the actual act of eating. In this example, automatic primary data collection and non-automatic secondary data collection combine to provide relatively high-accuracy and high-compliance food consumption measurement with relatively low privacy intrusion. This is an advantage over food consumption devices and methods in the prior art.

In an example, this device and system can prompt a person to use smart spoon 501 for eating and once the person is using smart spoon 501 for eating this spoon can automatically take pictures of mouthfuls of food that are in the spoon's scoop. In an example, such automatic picture taking can be triggered by infrared reflection, other optical sensor, pressure sensor, electromagnetic sensor, or other contact sensor in the spoon scoop. In another example, this device can prompt a person to manually trigger camera 502 to take a picture of food in the spoon's scoop. In another example, this device can prompt a person to aim camera 502 toward food on a plate, in a bowl, or in original packaging to take pictures of food before it is apportioned into mouthfuls by the spoon. In an example, food on a plate, in a bowl, or in original packaging can be easier to identify by analysis of its shape, texture, scale, and colors than food apportioned into mouthfuls.

In an example, use of camera 502 in smart spoon 501 can rely on having the person manually aim and trigger the camera for each eating event. In an example, the taking of food pictures in this manner requires at least one specific voluntary human action associated with each food consumption event, apart from the actual act of eating, in order to take pictures of food during that food consumption event. In an example, such specific voluntary human actions can be selected from the group consisting of: bringing smart spoon 501 to a meal or snack; using smart spoon 501 to eat food; aiming camera 502 of smart spoon 501 at food on a plate, in a bowl, or in original packaging; triggering camera 502 by touching a button, screen, or other activation surface; and triggering camera 502 by voice command or gesture command.

In an example, camera 502 of smart spoon 501 can be used to take multiple still-frame pictures of food. In an example, camera 502 of smart spoon 501 can be used to take motion (video) pictures of food from multiple angles. In an example, camera 502 can take pictures of food from at least two different angles in order to better segment a picture of a multi-food meal into different types of foods, better estimate the three-dimensional volume of each type of food, and better control for differences in lighting and shading. In an example, camera 502 can take pictures of food from multiple perspectives to create a virtual three-dimensional model of food in order to determine food volume. In an example, quantities of specific foods can be estimated from pictures of those foods by volumetric analysis of food from multiple perspectives and/or by three-dimensional modeling of food from multiple perspectives.

In an example, pictures of food on a plate, in a bowl, or in packaging can be taken before and after consumption. In an example, the amount of food that a person actually consumes (not just the amount ordered by the person or served to the person) can be estimated by measuring the difference in food volume from pictures before and after consumption. In an example, camera 502 can image or virtually create a fiduciary market to better estimate the size or scale of food. In an example, camera 502 can be used to take pictures of food which include an object of known size. This object can serve as a fiduciary marker in order to estimate the size and/or scale of food. In an example, camera 502, or another component on smart spoon 501, can project light beams within the field of vision to create a virtual fiduciary marker. In an example, pictures can be taken of multiple sequential mouthfuls of food being transported by the scoop of smart spoon 501 and used to estimate the cumulative amount of food consumed.

In an example, there can be a preliminary stage of processing or analysis of food pictures wherein image elements and/or attributes are adjusted, normalized, or standardized. In an example, a food picture can be adjusted, normalized, or standardized before it is compared with food pictures in a food database. This can improve segmentation of a meal into different types of food, identification of foods, and estimation of food volume or mass. In an example, food size or scale can be adjusted, normalized, or standardized before comparison with pictures in a food database. In an example, food texture can be adjusted, normalized, or standardized before comparison with pictures in a food database. In an example, food lighting or shading can be adjusted, normalized, or standardized before comparison with pictures in a food database. In various examples, a preliminary stage of food picture processing and/or analysis can include adjustment, normalization, or standardization of food color, texture, shape, size, context, geographic location, adjacent foods, place setting context, and temperature.

In an example, a food database can be used as part of a device and system for identifying types and amounts of food, ingredients, or nutrients. In an example, a food database can include one or more elements selected from the group consisting of: food name, food picture (individually or in combinations with other foods), food color, food packaging bar code or nutritional label, food packaging or logo pattern, food shape, food texture, food type, common geographic or intra-building locations for serving or consumption, common or standardized ingredients (per serving, per volume, or per weight), common or standardized nutrients (per serving, per volume, or per weight), common or standardized size (per serving), common or standardized number of calories (per serving, per volume, or per weight), common times or special events for serving or consumption, and commonly associated or jointly-served foods.

In an example, the boundaries between different types of food in a picture of a meal can be automatically determined to segment the meal into different food types before comparison with pictures in a food database. In an example, individual portions of different types of food within a multi-food meal can be compared individually with images of portions of different types of food in a food database. In an example, a picture of a meal including multiple types of food can be automatically segmented into portions of different types of food for comparison with different types of food in a food database. In an example, a picture of a meal with multiple types of food can be compared as a whole with pictures of meals with multiple types of food in a food database.

In an example, a food database can also include average amounts of specific ingredients and/or nutrients associated with specific types and amounts of foods for measurement of at least one selected type of ingredient or nutrient. In an example, a food database can be used to identify the type and amount of at least one selected type of ingredient that is associated with an identified type and amount of food. In an example, a food database can be used to identify the type and amount of at least one selected type of nutrient that is associated with an identified type and amount of food. In an example, an ingredient or nutrient can be associated with a type of food on a per-portion, per-volume, or per-weight basis.

In an example, automatic identification of food amounts and types can include extracting a vector of food parameters (such as color, texture, shape, and size) from a food picture and comparing this vector with vectors of these parameters in a food database. In various examples, methods for automatic identification of food types and amounts from food pictures can include: color analysis, image pattern recognition, image segmentation, texture analysis, three-dimensional modeling based on pictures from multiple perspectives, and volumetric analysis based on a fiduciary marker or other object of known size.

In various examples, food pictures can be analyzed in a manner which is at least partially automated in order to identify food types and amounts using one or more methods selected from the group consisting of: analysis of variance; chi-squared analysis; cluster analysis; comparison of a vector of food parameters with a food database containing such parameters; energy balance tracking; factor analysis; Fourier transformation and/or fast Fourier transform (FFT); image attribute adjustment or normalization; pattern recognition; comparison with food images with food images in a food database; inter-food boundary determination and food portion segmentation; linear discriminant analysis; linear regression and/or multivariate linear regression; logistic regression and/or probit analysis; neural network and machine learning; non-linear programming; principal components analysis; scale determination using a physical or virtual fiduciary marker; three-dimensional modeling to estimate food quantity; time series analysis; and volumetric modeling.

In an example, attributes of food in an image can be represented by a multi-dimensional food attribute vector. In an example, this food attribute vector can be statistically compared to the attribute vector of known foods in order to automate food identification. In an example, multivariate analysis can be done to identify the most likely identification category for a particular portion of food in an image. In various examples, a multi-dimensional food attribute vector can include attributes selected from the group consisting of: food color; food texture; food shape; food size or scale; geographic location of selection, purchase, or consumption; timing of day, week, or special event; common food combinations or pairings; image brightness, resolution, or lighting direction; infrared light reflection; spectroscopic analysis; and person-specific historical eating patterns. In an example, in some situations the types and amounts of food can be identified by analysis of bar codes, brand logos, nutritional labels, or other optical patterns on food packaging.

In an example, analysis of data concerning food consumption can include comparison of food consumption parameters between a specific person and a reference population. In an example, data analysis can include analysis of a person's food consumption patterns over time. In an example, such analysis can track the cumulative amount of at least one selected type of food, ingredient, or nutrient that a person consumes during a selected period of time.

In an example, pictures of food can be analyzed within the data processing unit of a hand-held device (such as a smart spoon) or a wearable device (such as a smart watch). In an example, pictures of food can be wirelessly transmitted from a hand-held or wearable device to an external device, wherein these food pictures are automatically analyzed and food identification occurs. In an example, the results of food identification can then be wirelessly transmitted back to the wearable or hand-held device. In an example, identification of the types and quantities of foods, ingredients, or nutrients that a person consumes can be a combination of, or interaction between, automated identification food methods and human-based food identification methods.

In the example shown in FIGS. 5 through 8, food-imaging camera 502 is built into smart spoon 501. In various alternative examples, a device and system for measuring a person's consumption of at least one selected type of food, ingredient, or nutrient can take pictures of food with an imaging device or component that is selected from the group consisting of: smart food utensil and/or electronically-functional utensil, smart spoon, smart fork, food probe, smart chop stick, smart plate, smart dish, or smart glass; smart phone, mobile phone, or cell phone; smart watch, watch cam, smart bracelet, fitness watch, fitness bracelet, watch phone, or bracelet phone; smart necklace, necklace cam, smart beads, smart button, neck chain, or neck pendant; smart finger ring or ring cam; electronically-functional or smart eyewear, smart glasses, visor, augmented or virtual reality glasses, or electronically-functional contact lens; digital camera; and electronic tablet.

14. Narrative to Accompany FIGS. 9 Through 12

The embodiment of this invention that is shown in FIGS. 9 through 12 is similar to the one that was just shown in FIGS. 5 through 8, except that now food pictures are taken by a general-purpose mobile electronic device (such as a smart phone) rather than by a specialized food utensil (such as a smart spoon). In this example, the general-purpose mobile electronic device is a smart phone. In other examples, a general-purpose mobile electronic device can be an electronic tablet or a digital camera.

The wearable food-monitoring component of the example shown in FIGS. 9 through 12 is again a smart watch with a motion sensor, like the one in previous examples. The smart watch and smart phone components of this example work together in FIGS. 9 through 12 in a similar manner to the way in which the smart watch and smart spoon components worked together in the example shown in FIGS. 5 through 8. We do not repeat the methodological detail of possible ways to identify food based on food pictures here because this was already discussed in the narrative accompanying the previous example.

FIG. 9 shows a rectangular general-purpose smart phone 901 that includes a camera (or other imaging component) 902. FIG. 10 shows a person grasping food item 1001 in their hand 206. FIG. 10 also shows that this person is wearing a smart watch 201 that includes communication unit 202, motion sensor 203, data processing unit 204, and power supply and/or transducer 205. In an example, food item 1001 can be a deep-fried pork rind. In another example, food item 1001 can be a blob of plain tofu; however, it is unlikely that any person who eats a blob of plain tofu would even need a device like this.

FIG. 11 shows this person bringing food item 1001 up to their mouth with a distinctive rotation of their wrist that is represented by the dotted-line arrow around hand 206. This indicates that the person is probably eating food. Using motion sensor 203, smart watch 201 detects this pattern of movement and detects that the person is probably eating something. Since the person has not yet taken a picture of food in association with this eating event, smart watch 201 prompts the person to take a picture of food using smart phone 901. This prompt 301 is represented in FIG. 11 by a "lightning bolt" symbol coming out from communication unit 202. We discussed a variety of possible prompts in earlier examples and do not repeat them here.

FIG. 12 shows that this person responds positively to prompt 301. This person responds by taking a picture of food items 1001 in bowl 1201 using camera 902 in smart phone 901. The field of vision of camera 902 is represented by dotted-line rays 1202 that radiate from camera 902 toward bowl 1201. In an example, the person manually aims camera 902 of smart phone 901 toward the food source (bowl 1201 in this example) and then triggers camera 902 to take a picture by touching the screen of smart phone 901. In another example, the person could trigger camera 902 with a voice command or a gesture command.

In this example, smart watch 201 and smart phone 901 share wireless communication. In an example, communication with smart watch 201 can be part of a smart phone application that runs on smart phone 901. In an example, smart watch 201 and smart phone 901 can comprise part of an integrated system for monitoring and modifying caloric intake and caloric expenditure to achieve energy balance, weight management, and improved health.

In an example, smart watch 201 and/or smart phone 901 can also be in communication with an external computer. An external computer can provide advanced data analysis, data storage and memory, communication with health care professionals, and/or communication with a support network of friends. In an example, a general purpose smart phone can comprise the computer-to-human interface of a device and system for measuring a person's consumption of at least one selected type of food, ingredient, or nutrient. In an example, such a device and system can communicate with a person by making calls or sending text messages through a smart phone. In an alternative example, an electronic tablet can serve the role of a hand-held imaging and interface device instead of smart phone 901.

FIGS. 9 through 12 show an embodiment of a device for measuring a person's consumption of at least one selected type of food, ingredient, or nutrient comprising a wearable food-consumption monitor (a smart watch in this example) that is configured to be worn on the person's wrist, arm, hand or finger and a hand-held food-identifying sensor (a smart phone in this example). The person is prompted to use the smart phone to take pictures of food when the smart watch indicates that the person is consuming food. In this example, primary data concerning food consumption that is collected by a smart watch includes data concerning movement of the person's body and secondary data for food identification that is collected by a smart phone includes pictures of food. In this example, the person is prompted to take pictures of food when they are moving in a manner that indicates that they are probably eating and secondary data has not already been collected.

The system for measuring food consumption that is shown in FIGS. 9 through 12 combines continual motion monitoring by a smart watch and food imaging by a smart phone. It is superior to prior art that relies only on a smart phone. A system for measuring food consumption that depends only on the person using a smart phone to take a picture of every meal and every snack they eat will probably have much lower compliance and accuracy than the system disclosed herein. With the system disclosed herein, as long as the person wears the smart watch (which can be encouraged by making it comfortable and tamper resistant), the system disclosed herein continually monitors for food consumption. A system based on a stand-alone smart phone offers no such functionality.

Ideally, if the smart watch 201 herein is designed to be sufficiently comfortable and unobtrusive, it can be worn all the time. Accordingly, it can even monitor for night-time snacking. It can monitor food consumption at times when a person would be unlikely to bring out their smart phone to take pictures (at least not without prompting). The food-imaging device and system that is shown here in FIGS. 9 through 12, including the coordinated operation of a motion-sensing smart watch and a wirelessly-linked smart phone, can provide highly-accurate food consumption measurement with relatively-low privacy intrusion.

15. Narrative to Accompany FIGS. 13 Through 22

Figure 13:
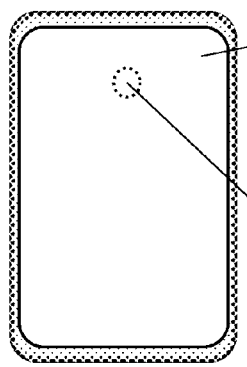
Figure 14:
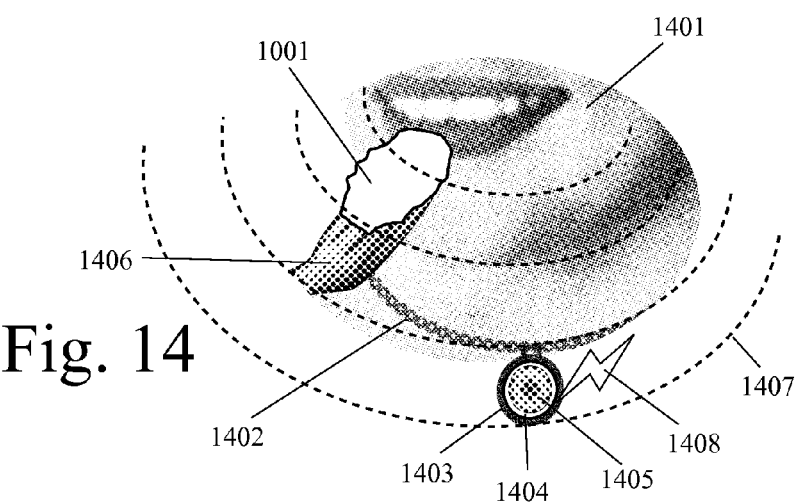
Figure 15:
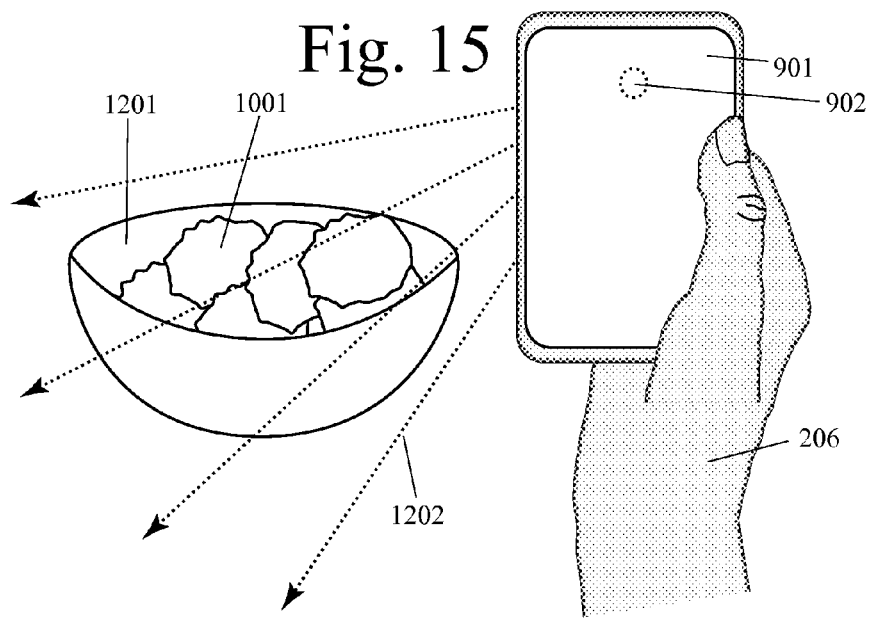

The embodiment of this invention that is shown in FIGS. 13 through 15 is similar to the one that was just shown in FIGS. 9 through 12, except that the wearable food-monitoring component is now a smart necklace instead of a smart watch. The smart necklace in this example monitors for food consumption by monitoring sounds instead of motion. In this example, the smart necklace detects food consumption by detecting chewing or swallowing sounds.

FIG. 13 shows the smart phone 901 with camera 902 that was introduced in the previous example. FIG. 14 shows that the person 1401 is wearing smart necklace 1402 including communication unit 1403, data processing unit and power supply 1404, and microphone 1405. FIG. 14 also shows that the person is eating food item 1001 using fork 1406.

In FIG. 14, microphone 1405 of smart necklace 1402 detects that the person is consuming food based on chewing or swallowing sounds. In FIG. 14, chewing or swallowing sounds are represented by dotted-line curves 1407 expanding outwardly from the person's mouth. Smart necklace 1402 then prompts the person to take a picture of food using camera 902 on smart phone 901. In FIG. 14, this prompt 1408 is represented by a "lightning bolt" symbol coming out from communication unit 1403.

FIG. 15 shows that the person responds to prompt 1408 by aiming camera 902 of smart phone 901 toward bowl 1201 containing food items 1001. The field of vision of camera 902 is represented by dotted-line rays 1202 that radiate outwards from camera 902 toward bowl 1201.

Figure 16:
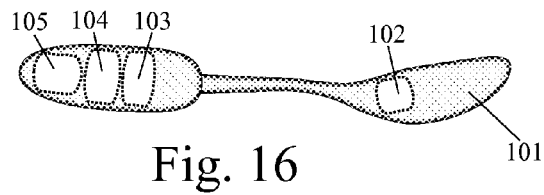
Figure 17:
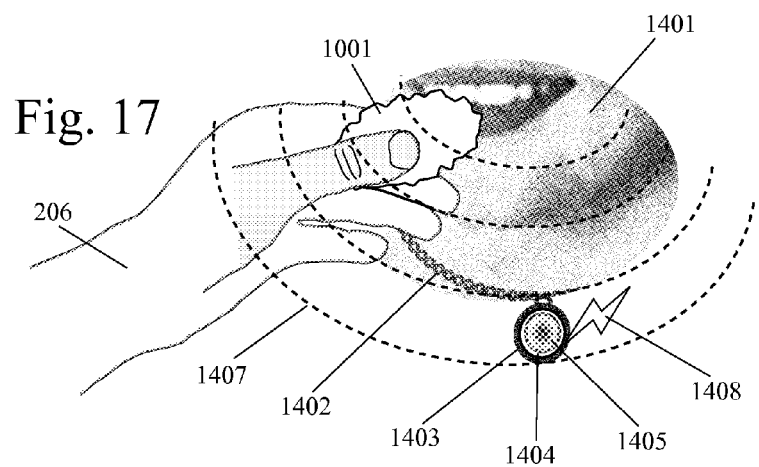
Figure 18:
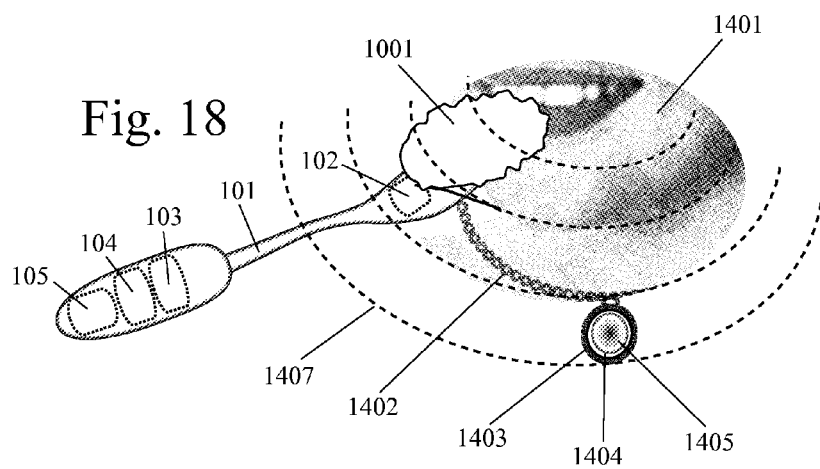

The embodiment of this invention that is shown in FIGS. 16 through 18 is similar to the one that was just shown in FIGS. 13 through 15, except that hand-held food-identifying component is the smart spoon that was introduced earlier instead of a smart phone. FIG. 16 shows smart spoon 101 with chemical composition sensor 102, data processing unit 103, communication unit 104, and power supply and/or transducer 105.

FIG. 17 shows that the person is eating food item 1001 without using smart spoon 101. In FIG. 17, microphone 1405 of smart necklace 1402 detects that the person is consuming food based on chewing or swallowing sounds 1407. In FIG. 14, chewing or swallowing sounds are represented by dotted-line curves 1407 expanding outwardly from the person's mouth. Smart necklace 1402 then prompts the person to use smart spoon 101 to eat food item 1001. In FIG. 14, this prompt 1408 is represented by a "lightning bolt" symbol coming out from communication unit 1403.

FIG. 18 shows that the person responds to prompt 1408 by using smart spoon 101. Use of smart spoon 101 brings food item 1001 into contact with chemical composition sensor 102 on smart spoon 101. This contact enables identification of food item 1001

The embodiment of this invention that is shown in FIGS. 19 through 22 is similar to the one that was shown in FIGS. 9 through 12 in that it also includes the integrated operation of a smart watch that monitors movement of a person's hand to detect eating events and a smart phone that the person uses to collect detailed information concerning the types and amounts of food consumed when an eating event occurs. However, in this example, data about the types and amounts of food consumed is received directly from the person through a human-to-computer interface on the smart phone, rather than by having the person use the smart phone to take pictures of food which are then analyzed to determine the types and amounts of food consumed.

In the example that is shown in FIGS. 19 through 22, the person uses the touch screen of smart phone 901 to directly enter data concerning the types and amounts of food that they consume during a particular eating event. If the person has not already entered such food consumption data in timely manner when the smart watch detects hand movement that indicates a probable eating event, then the smart watch prompts the person to enter such food consumption data via the smart phone. In an example, entry of food consumption data into the smart phone can be made easier through the use of a smart phone application that offers a convenient menu-driven food-identification interface. In an example, this application can proved access to a database of common types and amounts of food along with the nutritional information (e.g. ingredients, nutrients, and/or calories) for each such type and amount of food in the database.

In this example, a wearable food-monitoring component of this invention is a smart watch with a motion sensor. In this example, a secondary data collection component of this invention is a smart phone and/or a smart phone application. The smart watch and smart phone components work together in an integrated manner to collect accurate food consumption information with minimal privacy intrusion. The integration of data collection by both a smart watch and a smart phone can offer better food measurement accuracy, with a lower level of privacy intrusion, than is possible with data collection by a smart watch alone or by a smart phone alone.

Figure 19:
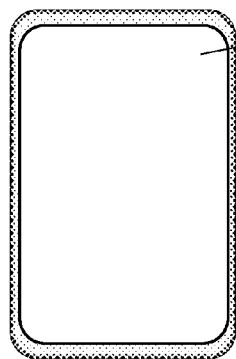
Figure 20:
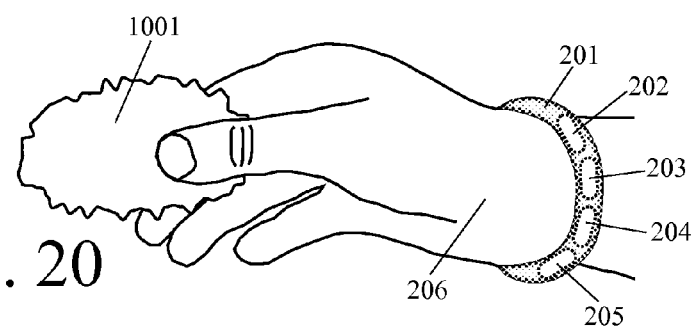
Figure 21:
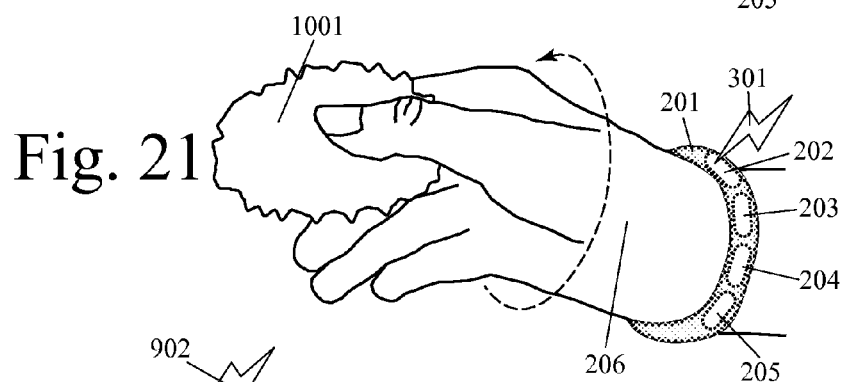

FIG. 19 shows the general-purpose smart phone 901 that was introduced in FIG. 9. FIG. 20 shows a person grasping food item 1001 in their hand 206, as first shown in FIG. 10. FIG. 20 also shows that this person is wearing a smart watch 201 that includes communication unit 202, motion sensor 203, data processing unit 204, and power supply and/or transducer 205, as first shown in FIG. 10. FIG. 21 shows this person bringing food item 1001 up to their mouth with a distinctive rotation of their wrist that is represented by the dotted-line arrow around hand 206, as first shown in FIG. 11. In this example, this distinctive hand motion indicates a probable eating event.

Using motion sensor 203, smart watch 201 detects a distinctive pattern of hand movement that indicates a probable eating event. However, as of FIG. 21 the person has not yet entered food consumption data into smart phone 901 for this eating event, so smart watch 201 prompts the person to use smart phone 901 to enter such food consumption data. This prompt 301 is represented in FIG. 21 by a "lightning bolt" symbol coming out from communication unit 202. In various examples, this prompt can be a vibration, sound, light, text message, or any of the other types of prompts which we discussed earlier. In an example, the prompt can comprise a calm voice coming that comes from the smart watch and says—"Dave . . . Are you eating something, Dave?"

Figure 22:
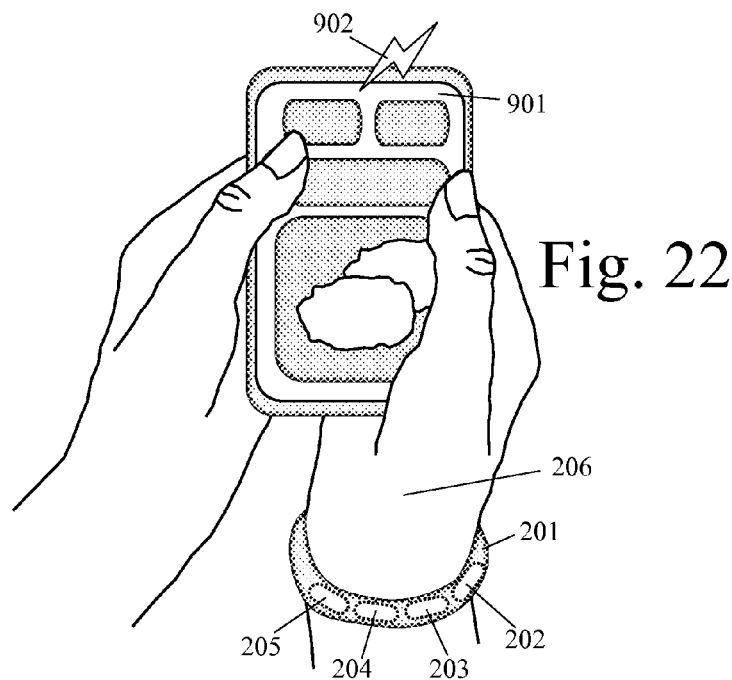

FIG. 22 shows that this person responds positively to prompt 301 by using the touch screen of smart phone 901 to enter data concerning the types and amounts of food that they are eating during this eating event. In this example, an image of food 1001 is shown on the screen of smart phone 901 as part of a phone application with a food database including food images. In another example, a person can enter food consumption data into a smart phone or other mobile electronic device using a keypad. In an example, a person can enter food consumption data into a smart phone or other mobile electronic device via a speech recognition interface. In an example, a person can enter food consumption data into a smart phone or other mobile electronic device via a gesture recognition interface.

In this example, smart watch 201 and smart phone 901 are separate, but they share wireless communication. In an example, wireless communication between smart watch 201 and smart phone 901 can be represented by electronic signals 301 and 902, respectively. In an example, wireless communication with smart watch 201 can be part of a smart phone application that runs on smart phone 901. In an example, smart watch 201 and smart phone 901 can be part of an integrated system for monitoring and modifying caloric intake and caloric expenditure to achieve energy balance, weight management, and improved health.

In an example, smart watch 201 and/or smart phone 901 can be in communication with an external computer via wireless signals 301 or 902, respectively. An external computer can provide advanced data analysis, data storage and memory, communication with health care professionals, and/or communication with a support network of friends. In an example, a general purpose smart phone can also comprise a computer-to-human interface of such a device and system for measuring a person's consumption of at least one selected type of food, ingredient, or nutrient. In an example, such a device and system can communicate with a person by making calls or sending text messages through a smart phone. In an alternative example, an electronic tablet can serve the role of an interface device instead of smart phone 901.

The example of this invention that is shown in FIGS. 19 through 22 can comprise a device for measuring a person's consumption of at least one selected type of food, ingredient, or nutrient comprising a wearable food-consumption monitor (a smart watch in this example) that is configured to be worn on the person's wrist, arm, hand or finger and a hand-held data collection device (a smart phone in this example). The person is prompted to use the smart phone to enter food consumption data when the smart watch indicates that the person is consuming food. In this example, primary data concerning food consumption that is collected by a smart watch includes data concerning movement of the person's body and secondary data for food identification that is collected by a smart phone includes food consumption data entered by the person via touch screen. In this example, the person is prompted to enter food consumption data when their hand movements suggest that they are probably eating and secondary data has not already been entered.

The system for measuring food consumption that is shown in FIGS. 19 through 22 combines substantially-continuous motion monitoring by a smart watch and data entry via a smart phone. This integrated device, method, and system can offer greater compliance and accuracy than a method that relies on someone entering food consumption data via a smart phone without any motion monitoring and/or prompting capability. Although some people may be sufficiently compulsive to enter food data for every meal or snack that they consume (even midnight snacks), having a wearable sensor with prompting capability provides a way of increasing compliance and detecting lack of compliance that a stand-alone smart phone does not provide. With the system disclosed herein, as long as the person wears the smart watch (which can be encouraged by making it comfortable and tamper resistant), the system disclosed herein continually monitors for food consumption. A system based on a stand-alone smart phone offers no such functionality.

Ideally, if the smart watch 201 is designed to be sufficiently comfortable and unobtrusive, it can be worn all the time. Accordingly, it can even monitor and detect night-time snacking. It can monitor food consumption at times when a person would be unlikely to bring out their smart phone to enter data without being prompted to do so. The device, method, and system that is shown in FIGS. 19 through 22, including the coordinated operation of a motion-sensing smart watch and a wirelessly-linked smart phone, can provide highly-accurate food consumption measurement with relatively-low privacy intrusion.

FIGS. 19 through 22 also show an example of how this invention can be embodied in a device for monitoring food consumption comprising: (a) a wearable sensor that is configured to be worn on a person's body or clothing, wherein this wearable sensor automatically collects data that is used to detect probable eating events without requiring action by the person in association with a probable eating event apart from the act of eating, and wherein a probable eating event is a period of time during which the person is probably eating; (b) a voluntary human-to-computer interface, wherein this interface receives data from the person concerning the food that the person eats, wherein receipt of this data requires voluntary action by the person apart from the act of eating, and wherein the person is prompted to enter data using this interface when data collected by the wearable sensor indicates a probable eating event; and (c) a data analysis component, wherein this component analyzes data received from the human-to-computer interface to estimate the types and amounts of foods, ingredients, nutrients, and/or calories that are consumed by the person. In this example, the wearable sensor is motion sensor 203. In this example, the voluntary human-to-computer interface is smart phone 901 and/or a software application of this phone. In this example, the data analysis component is data processing unit 204.

In the example that is shown in FIGS. 19 through 22, motion sensor 203 automatically collects data that is used to detect probable eating events. In this example, this data comprises data concerning hand motion. When one or more distinctive hand motions monitored by motion sensor 203 indicate a probable eating event, then communication unit 202 sends a signal that prompts the person to use smart phone 901 to enter data concerning food 1001 which the person is eating. When prompted, the person uses smart phone 901 to enter data concerning food 1001. Then, data analysis component 204 uses a food database to associate food 1001 with the types and amounts of ingredients, nutrients, and/or calories that are commonly associated with this food.

In this example, data analysis (including linking foods to a food database) occurs in wrist-based data analysis component 204. In other examples, data analysis (including linking foods to a food database) can occur in other locations. In an example, data analysis (including linking foods to a food database) can occur in a data analysis component that is located in phone 901. In another example, data analysis (including linking foods to a food database) can occur in a remote computer with which phone 901 and/or communication unit 202 is in wireless communication.

In the example that is shown in FIGS. 19 through 22, a wearable sensor is worn on the person's wrist. In other examples, a wearable sensor can be worn on a person's hand, finger, or arm. In this example, a wearable sensor is part of an electronically-functional wrist band or smart watch. In another example, a wearable sensor can be an electronically-functional adhesive patch that is worn on a person's skin. In another example, a sensor can be worn on a person's clothing.

In the example that is shown in FIGS. 19 through 22, a voluntary human-to-computer interface is part of a mobile phone or mobile phone application. In another example, a voluntary human-to-computer interface can be an electronic tablet or other mobile electronic device. In another example, a voluntary human-to-computer interface can be an electronically-functional necklace or other electronically-functional jewelry. In another example, a voluntary human-to-computer interface can be electronically-functional eyewear.

In the example that is shown in FIGS. 19 through 22, a wearable sensor automatically collects data concerning motion of the person's body. In another example, a wearable sensor can automatically collect data concerning electromagnetic energy that is emitted from the person's body or transmitted through the person's body. In another example, a wearable sensor can automatically collect data concerning thermal energy that is emitted from the person's body. In another example, a wearable sensor can automatically collect data concerning light energy that is reflected from the person's body or absorbed by the person's body. In various examples, food events can be detected by monitoring selected from the group consisting of: monitoring motion of the person's body; monitoring electromagnetic energy that is emitted from the person's body or transmitted through the person's body; monitoring thermal energy that is emitted from the person's body; and monitoring light energy that is reflected from the person's body or absorbed by the person's body.

In the example that is shown in FIGS. 19 through 22, the person is prompted to enter food consumption data using the human-to-computer interface when data collected by the wearable sensor indicates a probable eating event and the person does not enter data for this probable eating event before or at the start of the probable eating event. In another example, the person can be prompted to enter data using the human-to-computer interface when data collected by the wearable sensor indicates a probable eating event and the person does not enter data for this probable eating event before a selected length of time after the start of the probable eating event. In an example, the smart watch can prompt the person to enter food consumption data in real time, during the meal, for greater measurement accuracy than is possible with post-meal recollections.

In another example, the person can be prompted to enter data using the human-to-computer interface when data collected by the wearable sensor indicates a probable eating event and the person does not enter data for this probable eating event before a selected quantity of eating-related actions occurs during the probable eating event. In an example, the device can prompt the person to enter food consumption data if the person has not already done so after a selected number of mouthfuls of food have been consumed, as indicated by a selected number of distinctive hand-to-mouth motions detected by the smart watch.

In another example, the person can be prompted to enter data using the human-to-computer interface when data collected by the wearable sensor indicates a probable eating event and the person does not enter data for this probable eating event before the end of the probable eating event. In another example, the person can be prompted to enter data using the human-to-computer interface when data collected by the wearable sensor indicates a probable eating event and the person does not enter data for this probable eating event before a selected length of time after the end of the probable eating event.

In an example, a data analysis component can analyze data received from both the wearable sensor and the human-to-computer interface to evaluate the completeness of data received through the interface for tracking the person's total food consumption. In an example, a data analysis component can analyze data received from both the wearable sensor and the human-to-computer interface to evaluate the accuracy of data received through the interface for tracking the person's total food consumption.

In a variation on this example, this invention can be embodied in a device for monitoring food consumption comprising: (a) a wearable sensor that is configured to be worn on a person's wrist, hand, finger, or arm, wherein this wearable sensor automatically collects data that is used to detect probable eating events without requiring action by the person in association with a probable eating event apart from the act of eating, and wherein a probable eating event is a period of time during which the person is probably eating; (b) a voluntary human-to-computer interface, wherein this interface receives data from the person concerning the food that the person eats, wherein receipt of this data requires voluntary action by the person apart from the act of eating, and wherein the person is prompted to enter data using this interface when data collected by the wearable sensor indicates a probable eating event; and (c) a data analysis component, wherein this component analyzes data received from the human-to-computer interface to estimate the types and amounts of foods, ingredients, nutrients, and/or calories that are consumed by the person.

In a variation on this example, this invention can be embodied in a device for monitoring food consumption comprising: (a) a wearable sensor that is configured to be worn on a person's wrist, hand, finger, or arm, wherein this wearable sensor automatically collects data that is used to detect probable eating events without requiring action by the person in association with a probable eating event apart from the act of eating, wherein a probable eating event is a period of time during which the person is probably eating, and wherein this data is selected from the group consisting of data concerning motion of the person's body, data concerning electromagnetic energy emitted from or transmitted through the person's body, data concerning thermal energy emitted from the person's body, and light energy reflected from or absorbed by the person's body; (b) a voluntary human-to-computer interface, wherein this interface receives data from the person concerning the food that the person eats, wherein receipt of this data requires voluntary action by the person apart from the act of eating, wherein the person is prompted to enter data using this interface when data collected by the wearable sensor indicates a probable eating event; and wherein this interface receives data from the person through touch, voice, gesture, keys, and/or buttons; and (c) a data analysis component, wherein this component analyzes data received from the human-to-computer interface to estimate the types and amounts of foods, ingredients, nutrients, and/or calories that are consumed by the person, and wherein this component analyzes data received from both the sensor and the interface to evaluate the completeness of data received through the interface for tracking the person's total food consumption.

16. Conclusion of Narrative for Figures

FIGS. 1 through 22 show various examples of a device for measuring a person's consumption of at least one selected type of food, ingredient, or nutrient comprising: a wearable food-consumption monitor, wherein this food-consumption monitor is configured to be worn on a person's body or clothing, and wherein this food-consumption monitor automatically collects primary data that is used to detect when a person is consuming food, without requiring any specific action by the person in association with a specific eating event with the exception of the act of eating; and a hand-held food-identifying sensor, wherein this food-identifying sensor collects secondary data that is used to identify the person's consumption of at least one selected type of food, ingredient, or nutrient.

In FIGS. 1 through 22, the collection of secondary data by a hand-held food-identifying sensor requires a specific action by the person in association with a specific eating event apart from the act of eating. Also in FIGS. 1 through 22, the person whose food consumption is monitored is prompted to perform a specific action to collect secondary data when primary data collected by a food-consumption monitor indicates that the person is probably eating and the person has not already collected secondary data in association with a specific eating event.

FIGS. 1 through 12 show various examples of a device wherein a wearable food-consumption monitor is a smart watch or smart bracelet. FIGS. 9 through 15 and also FIGS. 19 through 22 show various examples of a device wherein a hand-held food-identifying sensor is a smart phone, cell phone, or mobile phone. FIGS. 1 through 8 and also FIGS. 16 through 18 show various examples of a device wherein a hand-held food-identifying sensor is a smart fork, smart spoon, other smart utensil, or food probe.

FIGS. 1 through 4 show an example of a device wherein a wearable food-consumption monitor is a smart watch or other electronic member that is configured to be worn on the person's wrist, arm, hand or finger; wherein a hand-held food-identifying sensor is a smart food utensil or food probe; and wherein a person is prompted to use the smart food utensil or food probe to analyze the chemical composition of food when the smart watch indicates that the person is consuming food.

FIGS. 1 through 4 show an example of a device wherein a wearable food-consumption monitor is a smart watch or other electronic member that is configured to be worn on the person's wrist, arm, hand or finger; wherein primary data collected by the smart watch or other electronic member that is configured to be worn on the person's wrist, arm, hand or finger includes data concerning movement of the person's body; wherein a hand-held food-identifying sensor is a smart food utensil or food probe; and wherein a person is prompted to use the smart food utensil or food probe to analyze the chemical composition of food when the smart watch indicates that the person is consuming food.

FIGS. 9 through 12 show an example of a device wherein a wearable food-consumption monitor is a smart watch or other electronic member that is configured to be worn on the person's wrist, arm, hand or finger; wherein a hand-held food-identifying sensor is a smart phone, cell phone, or mobile phone; and wherein a person is prompted to use the smart phone, cell phone, or mobile phone to take pictures of food or food packaging when the smart watch indicates that the person is consuming food.

FIGS. 9 through 12 show an example of a device wherein a wearable food-consumption monitor is a smart watch or other electronic member that is configured to be worn on the person's wrist, arm, hand or finger; wherein primary data collected by the smart watch or other electronic member that is configured to be worn on the person's wrist, arm, hand or finger includes data concerning movement of the person's body; wherein a hand-held food-identifying sensor is a smart phone, cell phone, or mobile phone; and wherein a person is prompted to use the smart phone, cell phone, or mobile phone to take pictures of food or food packaging when primary data indicates that the person is consuming food.

In another example: a wearable food-consumption monitor can be a smart watch or other electronic member that is configured to be worn on the person's wrist, arm, hand or finger wherein primary data collected by the smart watch or other electronic member that is configured to be worn on the person's wrist, arm, hand or finger includes data concerning electromagnetic energy received from the person's body; a hand-held food-identifying sensor can be a smart food utensil or food probe; and a person can be prompted to use the smart food utensil or food probe to analyze the chemical composition of food when the smart watch indicates that the person is consuming food.

In another example: a wearable food-consumption monitor can be a smart watch or other electronic member that is configured to be worn on the person's wrist, arm, hand or finger wherein primary data collected by the smart watch or other electronic member that is configured to be worn on the person's wrist, arm, hand or finger includes data concerning electromagnetic energy received from the person's body; a hand-held food-identifying sensor can be a smart phone, cell phone, or mobile phone; and a person can be prompted to use the smart phone, cell phone, or mobile phone to take pictures of food or food packaging when primary data indicates that the person is consuming food.

In another example: a wearable food-consumption monitor can be a smart watch or other electronic member that is configured to be worn on the person's wrist, arm, hand or finger wherein primary data collected by the smart watch or other electronic member that is configured to be worn on the person's wrist, arm, hand or finger includes images; a hand-held food-identifying sensor can be a smart food utensil or food probe; and a person can be prompted to use the smart food utensil or food probe to analyze the chemical composition of food when the smart watch indicates that the person is consuming food.

In another example: a wearable food-consumption monitor can be a smart watch or other electronic member that is configured to be worn on the person's wrist, arm, hand or finger wherein primary data collected by the smart watch or other electronic member that is configured to be worn on the person's wrist, arm, hand or finger includes images; a hand-held food-identifying sensor can be a smart phone, cell phone, or mobile phone; and a person can be prompted to use the smart phone, cell phone, or mobile phone to take pictures of food or food packaging when primary data indicates that the person is consuming food.

In another example: a wearable food-consumption monitor is a smart necklace or other electronic member that is configured to be worn on the person's neck, head, or torso wherein primary data collected by the smart watch or other electronic member that is configured to be worn on the person's wrist, arm, hand or finger includes patterns of sonic energy; a hand-held food-identifying sensor can be a smart food utensil or food probe; and a person can be prompted to use the smart food utensil or food probe to analyze the chemical composition of food when the smart watch indicates that the person is consuming food.

In another example: a wearable food-consumption monitor is a smart necklace or other electronic member that is configured to be worn on the person's neck, head, or torso wherein primary data collected by the smart watch or other electronic member that is configured to be worn on the person's wrist, arm, hand or finger includes patterns of sonic energy; a hand-held food-identifying sensor can be a smart phone, cell phone, or mobile phone; and a person can be prompted to use the smart phone, cell phone, or mobile phone to take pictures of food or food packaging when primary data indicates that the person is consuming food.

In an example, at least one selected type of food, ingredient, or nutrient for these examples can be selected from the group consisting of: a specific type of carbohydrate, a class of carbohydrates, or all carbohydrates; a specific type of sugar, a class of sugars, or all sugars; a specific type of fat, a class of fats, or all fats; a specific type of cholesterol, a class of cholesterols, or all cholesterols; a specific type of protein, a class of proteins, or all proteins; a specific type of fiber, a class of fiber, or all fiber; a specific sodium compound, a class of sodium compounds, and all sodium compounds; high-carbohydrate food, high-sugar food, high-fat food, fried food, high-cholesterol food, high-protein food, high-fiber food, and high-sodium food.

In an example, at least one selected type of food, ingredient, or nutrient can be selected from the group consisting of: a selected food, ingredient, or nutrient that has been designated as unhealthy by a health care professional organization or by a specific health care provider for a specific person; a selected substance that has been identified as an allergen for a specific person; peanuts, shellfish, or dairy products; a selected substance that has been identified as being addictive for a specific person; alcohol; a vitamin or mineral; vitamin A, vitamin B1, thiamin, vitamin B12, cyanocobalamin, vitamin B2, riboflavin, vitamin C, ascorbic acid, vitamin D, vitamin E, calcium, copper, iodine, iron, magnesium, manganese, niacin, pantothenic acid, phosphorus, potassium, riboflavin, thiamin, and zinc; a specific type of carbohydrate, class of carbohydrates, or all carbohydrates; a specific type of sugar, class of sugars, or all sugars; simple carbohydrates, complex carbohydrates; simple sugars, complex sugars, monosaccharides, glucose, fructose, oligosaccharides, polysaccharides, starch, glycogen, disaccharides, sucrose, lactose, starch, sugar, dextrose, disaccharide, fructose, galactose, glucose, lactose, maltose, monosaccharide, processed sugars, raw sugars, and sucrose; a specific type of fat, class of fats, or all fats; fatty acids, monounsaturated fat, polyunsaturated fat, saturated fat, trans fat, and unsaturated fat; a specific type of cholesterol, a class of cholesterols, or all cholesterols; Low Density Lipoprotein (LDL), High Density Lipoprotein (HDL), Very Low Density Lipoprotein (VLDL), and triglycerides; a specific type of protein, a class of proteins, or all proteins; dairy protein, egg protein, fish protein, fruit protein, grain protein, legume protein, lipoprotein, meat protein, nut protein, poultry protein, tofu protein, vegetable protein, complete protein, incomplete protein, or other amino acids; a specific type of fiber, a class of fiber, or all fiber; dietary fiber, insoluble fiber, soluble fiber, and cellulose; a specific sodium compound, a class of sodium compounds, and all sodium compounds; salt; a specific type of meat, a class of meats, and all meats; a specific type of vegetable, a class of vegetables, and all vegetables; a specific type of fruit, a class of fruits, and all fruits; a specific type of grain, a class of grains, and all grains; high-carbohydrate food, high-sugar food, high-fat food, fried food, high-cholesterol food, high-protein food, high-fiber food, and high-sodium food.

FIGS. 1 through 22 show various examples of a device for measuring a person's consumption of at least one selected type of food, ingredient, or nutrient comprising: (a) a wearable food-consumption monitor, wherein this food-consumption monitor is configured to be worn on a person's body or clothing, and wherein this food-consumption monitor automatically collects primary data that is used to detect when a person is consuming food, without requiring any specific action by the person in association with a specific eating event with the exception of the act of eating; (b) a hand-held food-identifying sensor, wherein this food-identifying sensor collects secondary data that is used to identify the person's consumption of at least one selected type of food, ingredient, or nutrient; wherein collection of secondary data by this hand-held food-identifying sensor requires a specific action by the person in association with a specific eating event apart from the act of eating; and (c) a computer-to-human interface, wherein this interface uses visual, auditory, tactile, electromagnetic, gustatory, and/or olfactory communication to prompt the person to use the hand-held food-identifying sensor to collect secondary data when primary data collected by the food-consumption monitor indicates that the person is probably eating and the person has not already collected secondary data in association with a specific eating event.

FIGS. 1 through 22 also show various examples of a method for measuring a person's consumption of at least one selected type of food, ingredient, or nutrient comprising: (a) automatically collecting primary data using a food-consumption monitor that a person wears on their body or clothing without requiring any specific action by the person in association with a specific eating event with the possible exception of the act of eating, wherein this primary data is used to detect when the person is consuming food; (b) collecting secondary data using a hand-held food-identifying sensor wherein collection of secondary data requires a specific action by the person in association with a specific eating event apart from the act of eating, and wherein this secondary data is used to identify the person's consumption of at least one selected type of food, ingredient, or nutrient; and (c) prompting the person to use a hand-held food-identifying sensor to collect secondary data when primary data collected by a food-consumption monitor indicates that the person is eating and the person has not already collected secondary data in association with a specific eating event.

Figures shown and discussed herein also disclose a device for monitoring food consumption comprising: (a) a wearable sensor that is configured to be worn on a person's body or clothing, wherein this wearable sensor automatically collects data that is used to detect probable eating events without requiring action by the person in association with a probable eating event apart from the act of eating, and wherein a probable eating event is a period of time during which the person is probably eating; (b) a voluntary human-to-computer interface, wherein this interface receives data from the person concerning the food that the person eats, wherein receipt of this data requires voluntary action by the person apart from the act of eating, and wherein the person is prompted to enter data using this interface when data collected by the wearable sensor indicates a probable eating event; and (c) a data analysis component, wherein this component analyzes data received from the human-to-computer interface to estimate the types and amounts of foods, ingredients, nutrients, and/or calories that are consumed by the person.

Figures shown and discussed herein disclose a device for monitoring food consumption wherein the wearable sensor is worn on a person's wrist, hand, finger, or arm. Figures shown and discussed herein disclose a device for monitoring food consumption wherein the wearable sensor is part of an electronically-functional wrist band. Figures shown and discussed herein disclose a device for monitoring food consumption wherein the wearable sensor is part of a smart watch. In another example, the wearable sensor can be part of an electronically-functional adhesive patch that is worn on a person's skin.

Figures shown and discussed herein disclose a device for monitoring food consumption wherein the human-to-computer interface is part of a mobile phone or mobile phone application. Figures shown and discussed herein disclose a device for monitoring food consumption wherein the wearable sensor and the human-to-computer interface are in wireless communication with each other.

Figures shown and discussed herein disclose a device for monitoring food consumption wherein the wearable sensor automatically collects data concerning motion of the person's body. In another example, the wearable sensor can automatically collect data concerning electromagnetic energy emitted from the person's body or transmitted through the person's body. In another example, the wearable sensor can automatically collect data concerning thermal energy emitted from the person's body. In another example, the wearable sensor can automatically collect data concerning light energy reflected from the person's body or absorbed by the person's body.

Figures shown and discussed herein disclose a device for monitoring food consumption wherein the person is prompted to enter data using the human-to-computer interface when data collected by the wearable sensor indicates a probable eating event and the person does not enter data for this probable eating event before or at the start of the probable eating event. In an example, the person can be prompted to enter data using the human-to-computer interface when data collected by the wearable sensor indicates a probable eating event and the person does not enter data for this probable eating event before a selected length of time after the start of the probable eating event. In an example, the person can be prompted to enter data using the human-to-computer interface when data collected by the wearable sensor indicates a probable eating event and the person does not enter data for this probable eating event before a selected quantity of eating-related actions occurs during the probable eating event.

In an example, the person can be prompted to enter data using the human-to-computer interface when data collected by the wearable sensor indicates a probable eating event and the person does not enter data for this probable eating event before the end of the probable eating event. In an example, the person can be prompted to enter data using the human-to-computer interface when data collected by the wearable sensor indicates a probable eating event and the person does not enter data for this probable eating event before a selected length of time after the end of the probable eating event.

In an example, the data analysis component can analyze data received from both the wearable sensor and the human-to-computer interface to evaluate the completeness of data received through the interface for tracking the person's total food consumption. In an example, the data analysis component can analyze data received from both the wearable sensor and the human-to-computer interface to evaluate the accuracy of data received through the interface for tracking the person's total food consumption.

Figures shown and discussed herein also disclose a device for monitoring food consumption comprising: (a) a wearable sensor that is configured to be worn on a person's wrist, hand, finger, or arm, wherein this wearable sensor automatically collects data that is used to detect probable eating events without requiring action by the person in association with a probable eating event apart from the act of eating, and wherein a probable eating event is a period of time during which the person is probably eating; (b) a voluntary human-to-computer interface, wherein this interface receives data from the person concerning the food that the person eats, wherein receipt of this data requires voluntary action by the person apart from the act of eating, and wherein the person is prompted to enter data using this interface when data collected by the wearable sensor indicates a probable eating event; and (c) a data analysis component, wherein this component analyzes data received from the human-to-computer interface to estimate the types and amounts of foods, ingredients, nutrients, and/or calories that are consumed by the person.

Figures shown and discussed herein also disclose a device for monitoring food consumption comprising: (a) a wearable sensor that is configured to be worn on a person's wrist, hand, finger, or arm, wherein this wearable sensor automatically collects data that is used to detect probable eating events without requiring action by the person in association with a probable eating event apart from the act of eating, wherein a probable eating event is a period of time during which the person is probably eating, and wherein this data is selected from the group consisting of data concerning motion of the person's body, data concerning electromagnetic energy emitted from or transmitted through the person's body, data concerning thermal energy emitted from the person's body, and light energy reflected from or absorbed by the person's body; (b) a voluntary human-to-computer interface, wherein this interface receives data from the person concerning the food that the person eats, wherein receipt of this data requires voluntary action by the person apart from the act of eating, wherein the person is prompted to enter data using this interface when data collected by the wearable sensor indicates a probable eating event; and wherein this interface receives data from the person through touch, voice, gesture, keys, and/or buttons; and (c) a data analysis component, wherein this component analyzes data received from the human-to-computer interface to estimate the types and amounts of foods, ingredients, nutrients, and/or calories that are consumed by the person, and wherein this component analyzes data received from both the sensor and the interface to evaluate the completeness of data received through the interface for tracking the person's total food consumption.

I claim:

1. A device for monitoring food consumption comprising:
   a near-infrared spectroscopic sensor that is configured to be worn on a person's ear, wherein the near-infrared spectroscopic sensor automatically collects data concerning light energy in the near-infrared portion of the light spectrum that is reflected from the person's body and/or absorbed by the person's body;
   a microphone that is configured to be worn on the person's ear, wherein the microphone receives voice data from the person concerning the food that the person eats
   a voice-producing interface that is configured to be worn on the person's ear, wherein the interface produces a voice which prompts the person to enter voice data concerning what the person is eating using the microphone when data collected by the near-infrared spectroscopic sensor indicates a probable eating event; and
   a data analysis component, wherein this component analyzes data received from the near-infrared spectroscopic sensor and the microphone to estimate the types and amounts of foods, ingredients, nutrients, and/or calories that are consumed by the person.

2. The device in claim 1 wherein the person is prompted to enter data using the microphone when data collected by the near-infrared spectroscopic sensor indicates a probable eating event and the person does not enter data for this probable eating event before or at the start of the probable eating event.

3. The device in claim 1 wherein the person is prompted to enter data using the microphone when data collected by the near-infrared spectroscopic sensor indicates a probable eating event and the person does not enter data for this probable eating event before a selected length of time after the start of the probable eating event.

4. The device in claim 1 wherein the person is prompted to enter data using the microphone when data collected by the near-infrared spectroscopic sensor indicates a probable eating event and the person does not enter data for this probable eating event before a selected quantity of eating-related actions occurs during the probable eating event.

5. The device in claim 1 wherein the person is prompted to enter data using the microphone when data collected by the near-infrared spectroscopic sensor indicates a probable eating event and the person does not enter data for this probable eating event before the end of the probable eating event.

6. The device in claim 1 wherein the person is prompted to enter data using the microphone when data collected by the near-infrared spectroscopic sensor indicates a probable eating event and the person does not enter data for this probable eating event before a selected length of time after the end of the probable eating event.

* * * * *